United States Patent
Ruiz-Opazo et al.

(10) Patent No.: US 10,849,966 B2
(45) Date of Patent: *Dec. 1, 2020

(54) METHODS FOR TREATING NETOSIS AND NEUTROPHIL ACTIVATION

(71) Applicant: TRUSTEES OF BOSTON UNIVERSITY, Boston, MA (US)

(72) Inventors: Nelson Ruiz-Opazo, Westwood, MA (US); Victoria L. M. Herrera, Westwood, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/134,070

(22) Filed: Sep. 18, 2018

(65) Prior Publication Data

US 2019/0083595 A1 Mar. 21, 2019

Related U.S. Application Data

(60) Provisional application No. 62/559,874, filed on Sep. 18, 2017, provisional application No. 62/685,377, filed on Jun. 15, 2018.

(51) Int. Cl.

| | |
|---|---|
| *A61K 39/00* | (2006.01) |
| *A61K 9/51* | (2006.01) |
| *C07K 16/28* | (2006.01) |
| *A61P 35/00* | (2006.01) |
| *C12N 9/78* | (2006.01) |
| *C12N 9/50* | (2006.01) |
| *C12N 9/08* | (2006.01) |
| *C12N 9/16* | (2006.01) |
| *A61P 11/00* | (2006.01) |
| *A61P 9/12* | (2006.01) |

(52) U.S. Cl.
CPC ........ *A61K 39/001109* (2018.08); *A61K 9/51* (2013.01); *A61P 9/12* (2018.01); *A61P 11/00* (2018.01); *A61P 35/00* (2018.01); *C07K 16/2863* (2013.01); *C12N 9/0065* (2013.01); *C12N 9/16* (2013.01); *C12N 9/50* (2013.01); *C12N 9/78* (2013.01); *A61K 2039/505* (2013.01); *C07K 2317/24* (2013.01); *C07K 2317/73* (2013.01); *C07K 2317/76* (2013.01); *C12Y 111/02002* (2013.01); *C12Y 301/21001* (2013.01); *C12Y 304/21037* (2013.01); *C12Y 304/24007* (2013.01); *C12Y 305/03001* (2013.01); *C12Y 305/04004* (2013.01)

(58) Field of Classification Search
CPC ........... A61K 39/001109; A61K 39/00; A61K 2039/505; A61K 9/51; C07K 16/2866; C07K 2317/21; C07K 2317/34; C07K 2317/53; C07K 2317/56; C07K 2317/76; C07K 2317/92
See application file for complete search history.

(56) References Cited

U.S. PATENT DOCUMENTS

| | | | |
|---|---|---|---|
| 4,867,973 A | 9/1989 | Goers | |
| 5,969,098 A | 10/1999 | Brittain | |
| 7,504,490 B1 | 3/2009 | Weinstock | |
| 8,956,609 B2 | 2/2015 | Herrera et al. | |
| 2009/0028852 A1 | 1/2009 | Herrera | |
| 2009/0215680 A1 | 8/2009 | Caboche et al. | |
| 2009/0317836 A1 | 12/2009 | Kuhn | |
| 2011/0313229 A1 | 12/2011 | Sugaya | |
| 2013/0022551 A1 | 1/2013 | Ruiz-Opazo | |
| 2013/0177500 A1 | 7/2013 | Ruiz-Opaz | |
| 2016/0108124 A1* | 4/2016 | Ruiz-Opazo | A61K 38/18 424/133.1 |
| 2017/0058036 A1 | 3/2017 | Ruiz-Opazo | |
| 2017/0253657 A1 | 9/2017 | Constantin | |

FOREIGN PATENT DOCUMENTS

| | | |
|---|---|---|
| WO | 2003/002144 A1 | 1/2003 |
| WO | 2006/055665 A2 | 5/2006 |
| WO | 2007102354 A2 | 9/2007 |
| WO | 2010/114801 A1 | 10/2010 |
| WO | 2012/012750 A1 | 1/2012 |
| WO | 2013/112467 A1 | 8/2013 |

OTHER PUBLICATIONS

Vajdos et al. Comprehensive Functional Maps of the Antigen binding Site of an Anti-ErbB2 Antibody Obtained with Shotgun Scanning Mutagenesis. J Mol Biol. Jul. 5, 2002;320(2):415-28 (Year: 2002).*
Brown et al. Tolerance to Single, but Not Multiple, Amino Acid Replacements in Antibody VH CDR2. J Immunol. May 1996;156(9): 3285-91 (Year: 1996).*
Khandpur et al. NETs Are a Source of Citrullinated Autoantigens and Stimulate Inflammatory Responses in Rheumatoid Arthritis. Science Translational Medicine, 2013; 5(178):1-10 (Year: 2013).*
Park et al. Evaluation of circulating markers of neutrophil extracellular traps formation as risk factors for diabetic retinopathy in a case-control association study. Exp Clin Endocrinol Diabetes, 2016; 124(09):557-561 (Year: 2016).*
Valles et al. Neutrophil extracellular traps are increased in patients with acute ischemic stroke: prognostic significance. Thromb Haemost, 2017; 117:1919-1929 (Year: 2017).*

(Continued)

*Primary Examiner* — Vanessa L. Ford
*Assistant Examiner* — Sandra E Dillahunt
(74) *Attorney, Agent, or Firm* — Nixon Peabody LLP; Ronald I. Eisenstein; Nicole D. Kling

(57) ABSTRACT

Described herein are methods and compositions relating to methods of inhibiting neutrophils, e.g., inhibiting NET release or NETosis, by means of a DEspR inhibitor, e.g., an anti-DEspR antibody reagent. In some embodiments, the methods can relate to the treatment of a disease, e.g., cancer or a disease wherein neutrophils; NETs; or NETosing or NETting neutrophils contribute to pathogenesis, chronicity, or worsening of disease. In some embodiments, the DEspR inhibitor can be a bi-specific reagent or an antibody-drug conjugate.

14 Claims, 40 Drawing Sheets

Specification includes a Sequence Listing.

(56) References Cited

OTHER PUBLICATIONS

Jung et al. Cancer cell-induced neutrophil extracellular traps promote both hypercoagulability and cancer progression. PLOS One, 20109; 14(4): 1-16 (Year: 2016).*

Narasaraju et al., "Neutrophils as Possible Therapeutic Targets in Severe Influenza Pneumonia." Journal of Infectious Pulmonary Diseases 2(2):1-3 (2016).

Abdollahi et al., "Evading tumor evasion: current concepts and perspectives of anti-angiogenic cancer therapy", Drug Resist Updat 13(1-2) 16-28 (2010).

Bergers et al., "Modes of resistance to anti-angiogenic therapy", Nat Rev Cancer 8(8) 592-603 (2008).

Brown et al., "Tolerance of single, but not multiple, amino acid replacements in antibody VH CDR 2: a means of minimizing B cell wastage from somatic hypermutation?", J Immunol 156(9) 3285-3291 (1996).

Carmeliet et al., "Abnormal blood vessel development and lethality in embryos lacking a single VEGF allele", Nature 380(6573) 435-439 (1996).

Carmeliet et al., "Angiogenesis in life, disease and medicine", Nature 438(7070) 932-936 (2005).

Casset et al., "A peptide mimetic of an anti-CD4 monoclonal antibody by rational design", Biochem Biophys Res Commun 307(1) 198-205 (2003).

Clouthier et al., "Cranial and cardiac neural crest defects in endothelin-A receptor-deficient mice", Development 125(5) 813-824 (1998).

Colman et al., "Effects of amino acid sequence changes on antibody-antigen interactions", Res Immunol 145(1) 33-36 (1994).

Cools-Lartigue et al., "Neutrophil extracellular traps in cancer progression." Cellular and Molecular Life Sciences 71(21):4179-4194 (2014).

Crawford et al., "Chapter 6. Mouse models to investigate anti-cancer effects of VEGF inhibitors", Methods Enzymol 445: 125-139 (2008).

Decano et al., "Dual enothelin-1/VEGFsp receptor (DEspR) roles in adult angiogenesis in despr+/− knockout micr and carotid artery disease rat model", Manuscript submitted to Circulation. (2010).

Decano et al., "Early-life sodium exposure unmasks susceptibility to stroke in hyperlipidemic, hypertensive heterozygous Tg25 rats transgenic for human cholesteryl ester transfer protein", Circulation 119(11) 1501-1509 (2009).

Decano et al., "Molecular imaging of vasa vasorum neovascularization via DEspR-targeted contrast-enhanced ultrasound microimaging in transgenic atherosclerosis rat model", Mol Imaging Biol 13(6) 1096-1106 (2011).

Ebos et al., "Accelerated metastasis after short-term treatment with a potent inhibitor of tumor angiogenesis", Cancer Cell 15(3) 232-239 (2009).

Edwards et al., "Regulation of neutrophil apoptosis by Mcl-1" Biochemical Society Transactions 32:489-492 (2004).

El Kebir et al., "Modulation of neutrophil apoptosis and the resolution of inflammation through β2 integrins." Frontiers in Immunology 4(6) (2013).

El Kebir et al., "Targeting neutrophil apoptosis for enhancing the resolution of inflammation." Cells 2(2):330-348 (2013).

Fadini et al., "A perspective on NETosis in diabetes and cardiometabolic disorders." Nutrition, Metabolism and Cardiovascular Diseases 26(1):1-8 (2016).

Ferrara et al., "Heterozygous embryonic lethality induced by targeted inactivation of the VEGF gene", Nature 380 (6573)439-442 (1996).

Ferrara et al., "Pathways mediating VEGF-independent tumor angiogenesis", Cytokine Growth Factor Rev 21(1) 21-26 (2010).

Gamicia et al., "Neutrophil extracellular traps in sepsis." Shock 42(4):286-294 (2014).

Gattinoni et al., "Ventilator-induced lung injury: the anatomical and physiological framework." Critical Care Medicine 38(10):S539-S548 (2010).

GenBank, dual endothelial-1 (VEGRsp)/angiotension II receptor [Homo sapiens], NCBI Locus ABP04239, AC 4BP04236 GI:144954326 (2008).

Gloriosso et al., "Association of ATP1A1 and dear single-nucleotide polymorphism haplotypes with essential hypertension: sex-specific and haplotype-specific effects", Circ Res 100(10) 1522-1529 (2007).

Hanahan et al., "Hallmarks of cancer: the next generation", Cell 144(5) 646-674 (2011).

Herrera et al., "Analysis of gender-specific atherosclerosis susceptibility in transgenic[hCETP]25DS rat model", Atherosclerosis 17791) 9-18 (2004).

Herrera et al., "Confirmation of translatability and functionality certifies the dual endothelin1/VEGFsp receptor (DEspR) protein." BMC Molecular Biology 17(1):15 (2016).

Herrera et al., "DEspR roles in tumor vasculo-angiogenesis, invasiveness, CSC-survival and anoikis resistance: a common receptor coordinator'paradigm." PloS One 9(1):e85821 (2014).

Herrera et al., "Embryonic lethality in Dear gene-deficient mice: new player in angiogenesis", Physiol Genomics 23 (3) 257-268 (2005).

Herrera et al., "Sex-specific hippocampus-dependent cognitive deficits and increased neuronal autophagy in DEspR haploinsufficiency in mice", Physiol Genomics 35(3) 316-329 (2008).

Lin et al., "Origins of circulating endothelial cells and endothelial outgrowth from blood", J Clin Invest 105(1) 71-77 (2000).

Loges et al., "Mechanisms of resistance to anti-angiogenic therapy and development of third-generation antiangiogenic drug candidates", Genes Cancer 1(1) 12-25 (2010).

MacCallum et al., "Antibody-antigen interactions: contact analysis and binding site topography", J Mol Biol 262(5) 732-745 (1996).

Michaud et al., "Mechanisms of ventilator-induced lung injury: the clinician's perspective." Critical Care 7(3):209-2010 (2003).

Paez-Ribes et al., "Antiangiogenic therapy elicits malignant progression of tumors to increased local invasion and distant metastasis", Cancer Cell 15(3) 220-231 (2009).

Paul, "Fundamental Immunology", Third Edition, Raven Press, New York, Chapter 8, 292-295 (1993).

Rudikoff et al., "Single amino acid substitution altering antigen-binding specificity", Proc Natl Acad Sci USA 79(6) 1979-1983 (1982).

Ruiz-Opazo et al., "Molecular characterization of a dual endothelin-1/Angiotensin II receptor", Mol Med 4(2) 96-108 (1998).

Swami et al., "Multipotent tumour endothelial cells", Nature Reviews Cancer 8(11) 2008.

Thalin et al., "NETosis promotes cancer-associated arterial microthrombosis presenting as ischemic stroke with troponin elevation." Thrombosis Research 139:56-64 (2016).

UniProt Submission B0L3A2_Human [Retrieved from Internet Feb. 7, 2017; <http://www.uniprot.org/uniprot/B0L3A2.txt?version=11>] (2008).

Vajdos et al., "Comprehensive functional maps of the antigen-binding site of an anti-ErbB2 antibody obtained with shotgun scanning mutagenesis", J Mol Biol 320(2) 415-428 (2002).

Wong et al., "Diabetes primes neutrophils to undergo NETosis, which impairs wound healing." Nature Medicine 21 (7):815-819 (2015).

Yang et al., "Identification of local and circulating cancer stem cells in human liver cancer", Hepatolofy 47(3) 919-928 (2008).

Fridlender et al. "Transcriptomic Analysis Comparing Tumor-Associated Neutrophils with Granulocytic Myeloid-Derived Suppressor Cells and Normal Neutrophils." PLoS One 7(2): e31524 (2012).

Templeton et al. "Prognostic Role of Neutrophil-to-Lymphocyte Ratio in Solid Tumors: A Systematic Review and Meta-Analysis" JNCI: Journal of the National Cancer Institute 106(6): 1-11 (2014).

McCarthy, "Antiangiogenesis drug promising for metastatic colorectal cancer." The Lancet 361(9373): 1959 (2003).

Arai et al. "Serum Neutrophil Extracellular Trap Levels Predict Thrombotic Microangiopathy after Allogenic Stem Cell Transplantation." Biol Blood Marrow Transplant 19(12): 1683-1689 (2013).

Barliya et al. "Possible involvement of NETosis in inflammatory processes in the eye: Evidence from a small cohort of patients." Molecular vision 23: 922-932 (2017).

(56) References Cited

OTHER PUBLICATIONS

Barnado et al. "At the bedside: neutrophil extracellular traps (NETs) as targets for biomarkers and therapies in autoimmune diseases." Journal of leukocyte biology 99(2): 265-278 (2016).
Berger-Achituv et al. "A proposed role for neutrophil extracellular traps in cancer immunoediting." Frontiers in Immunology 4(48): 1-5 (2013).
Borissoff et al. "Elevated levels of circulating DNA and chromatin are independently associated with severe coronary atherosclerosis and a prothrombotic state." Arteriosclerosis, thrombosis, and vascular biology 33(8): 2032-2040 (2013).
Czaikoski et al. "Neutrophil extracellular traps induce organ damage during experimental and clinical sepsis." PloS one 11(2): e0148142 pp. 1-19 (2016).
Döring et al. "Neutrophil extracellular traps in atherosclerosis and atherothrombosis." Circulation research 120(4): 736-743 (2017).
Greco et al. "Platelets and multi-organ failure in sepsis." International journal of molecular sciences 18(10): 2200 pp. 1-10 (2017).
Hakkim et al. "Impairment of neutrophil extracellular trap degradation is associated with lupus nephritis." Proceedings of the National Academy of Sciences 107(21): 9813-9818 (2010).
Hamaguchi et al. "Identification of neutrophil extracellular traps in the blood of patients with systemic inflammatory response syndrome." Journal of International Medical Research 41(1): 162-168 (2013).
He et al. "Phosphotidylserine exposure and neutrophil extracellular traps enhance procoagulant activity in patients with inflammatory bowel disease." Thrombosis and haemostasis 115(04): 738-751 (2016).
Jorch et al. "An emerging role for neutrophil extracellular traps in noninfectious disease." Nature medicine 23(3): 279-287 (2017).
Kessenbrock et al. "Netting neutrophils in autoimmune small-vessel vasculitis." Nature Medicine 15(6): 623-625 (2009).
Kim et al. "Increased neutrophil extracellular trap formation in uremia is associated with chronic inflammation and prevalent coronary artery disease." Journal of immunology research 2017: 1-10 (2017).
Korabecna et al. "NETosis provides the link between activation of neutrophils on hemodialysis membrane and comorbidities in dialyzed patients." Inflammation Research 66(5): 369-378 (2017).
Liu et al. "201: Neutrophil Extracellular Traps (Nets) Formation After Traumatic Brain Injury." Critical Care Medicine 40(12): 1-328 (2012).
Margraf et al. "Neutrophil-derived circulating free DNA (cf-DNA/NETs): a potential prognostic marker for posttraumatic development of inflammatory second hit and sepsis." Shock 30(4): 352-358 (2008).
Menegazzo et al. "NETosis is induced by high glucose and associated with type 2 diabetes." Acta diabetologica 52 (3): 497-503 (2015).
Mitsios et al. "NETopathies? Unraveling the dark side of old diseases through neutrophils." Frontiers in immunology 7(678): 1-13 (2017).
Nakazawa et al. "Histones and neutrophil extracellular traps enhance tubular necrosis and remote organ injury in Ischemic AKI." Journal of the American Society of Nephrology 28(6): 1753-1768 (2017).
Papayannopoulos. "Neutrophil extracellular traps in immunity and disease." Nature Reviews Immunology 18(2): 134-147 (2018).
Porto et al. "Neutrophil extracellular traps in pulmonary diseases: too much of a good thing?" Frontiers in Immunology 7(311): 1-13 (2016).
Quillard et al. "TLR2 and neutrophils potentiate endothelial stress, apoptosis and detachment: implications for superficial erosion." European heart journal 36(22): 1394-1404 (2015).
Tillack et al. "Gender differences in circulating levels of neutrophil extracellular traps in serum of multiple sclerosis patients." Journal of neuroimmunology 261(1-2): 108-119 (2013).
Yuen et al. "NETosing neutrophils activate complement both on their own NETs and bacteria via alternative and non-alternative pathways." Frontiers in immunology 7(137): 1-14 (2016).

\* cited by examiner

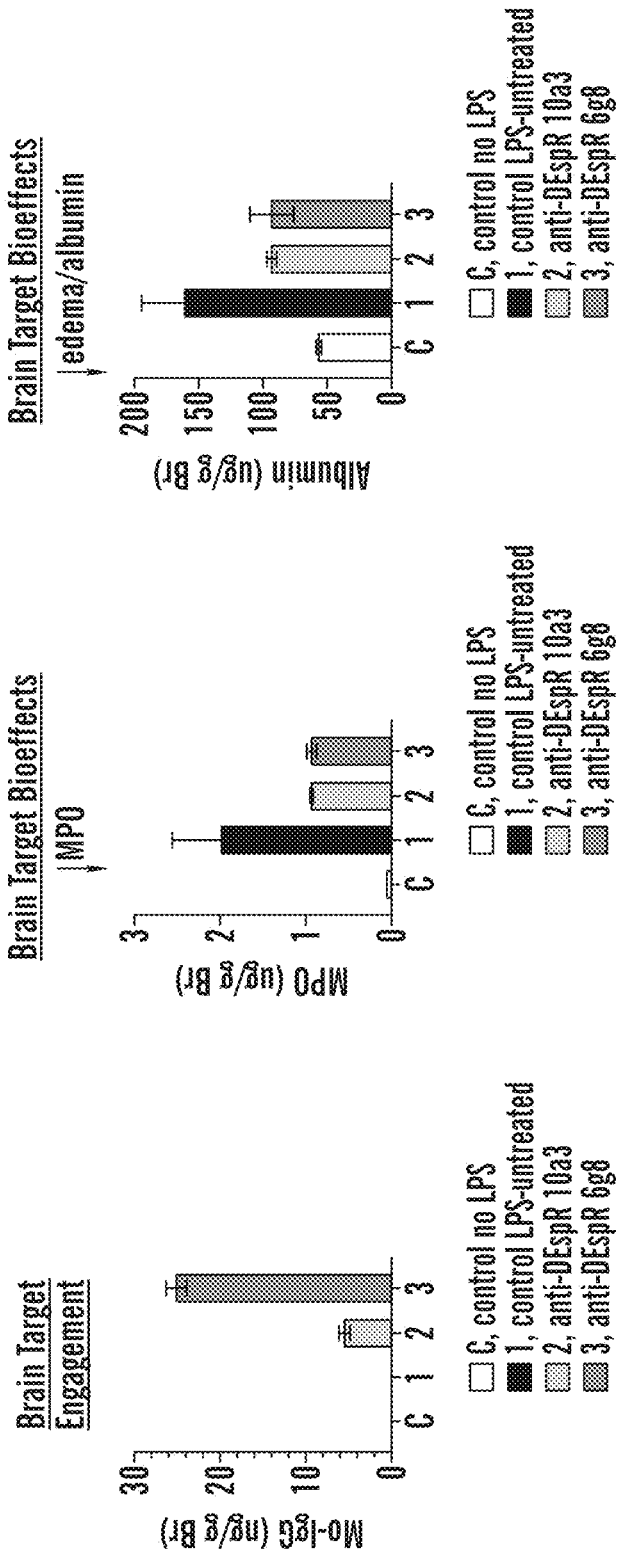

Tumor associated neutrophils or activated neutrophils in tumors contribute to immune evasion in 3 main ways:
1) Induction of T-cell apoptosis via neutrophil expression of PD-L1 (programmed death receptor ligand) that engages PD-1 (programmed death receptor-1) on T-cells
2) Inhibition of T-cell proliferation and TCR expression by neutrophil release of arginase-1 (ARG), and inhibition of immune synapse maturation and survival by oxidation of cofilin by neutrophil-release of reactive oxygen species (ROS), and
3) Inhibition of T-cell activation via release of proteases (cathepsin G, elastase) that break down T-cell stimulating cytokines (interleukin-2 or IL-2, interleukin-6 or IL-6). Proteases (neutrophil elastase) also lead to receptor shedding on T-cells.

FIG. 8 (cont.)

Spontaneous mammary tumors in immune-competent 12-14 m post-menopausal rats.

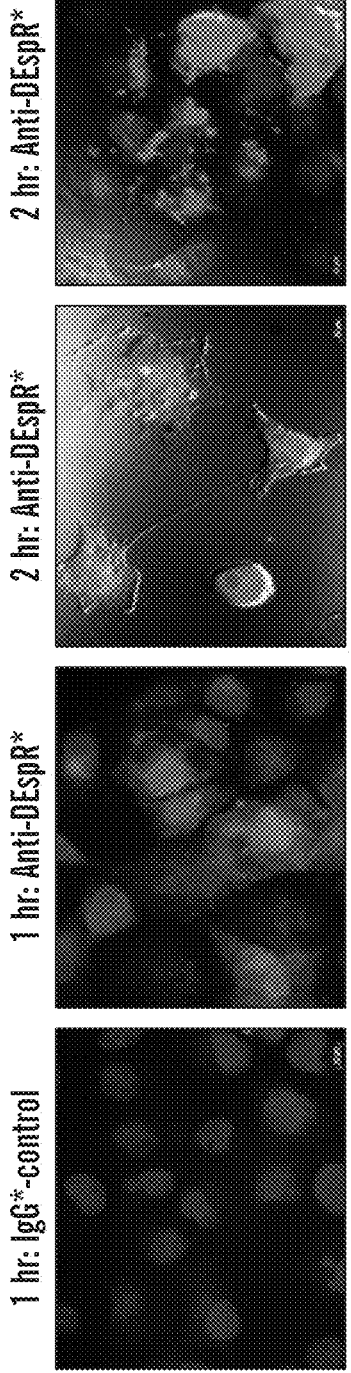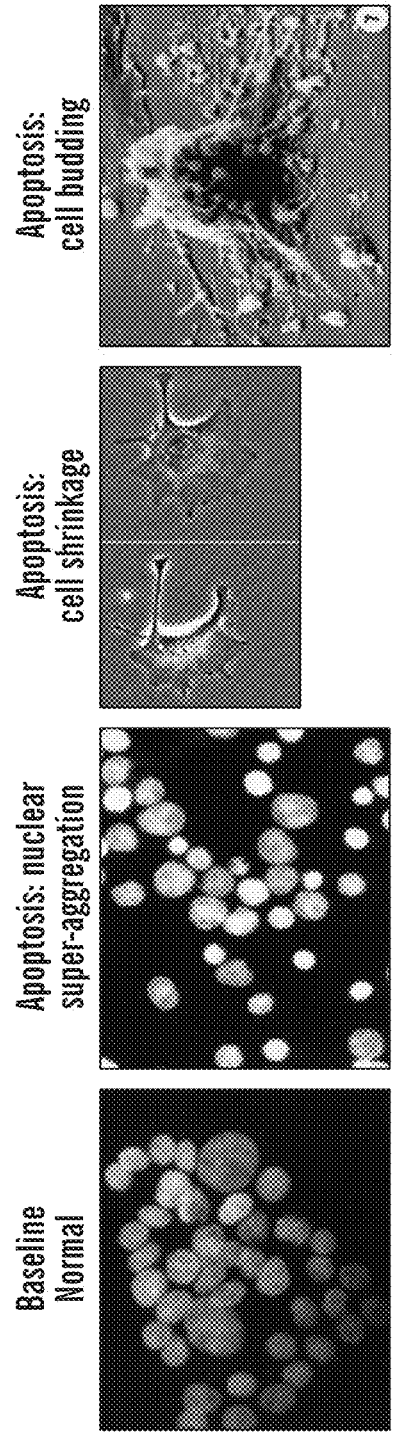
FIG. 15

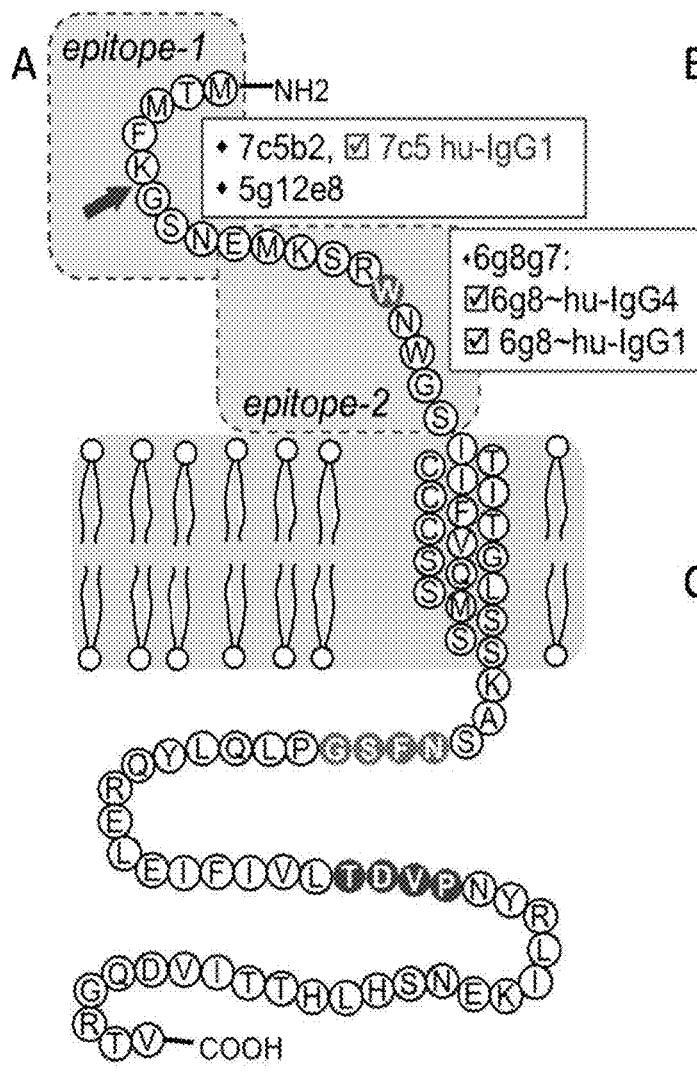
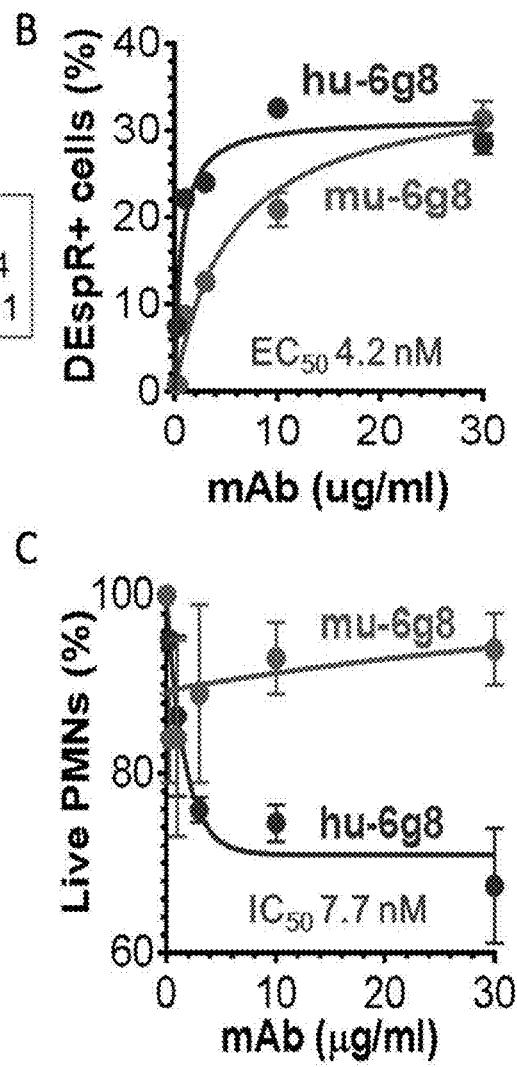
Figs. 17A-17C

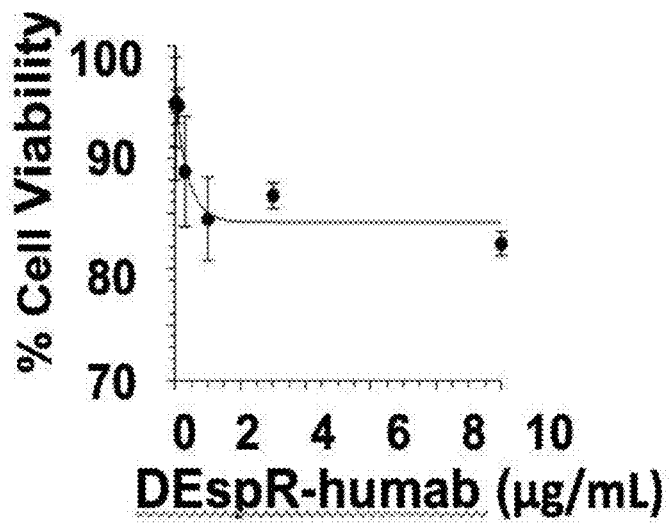
Fig 20A
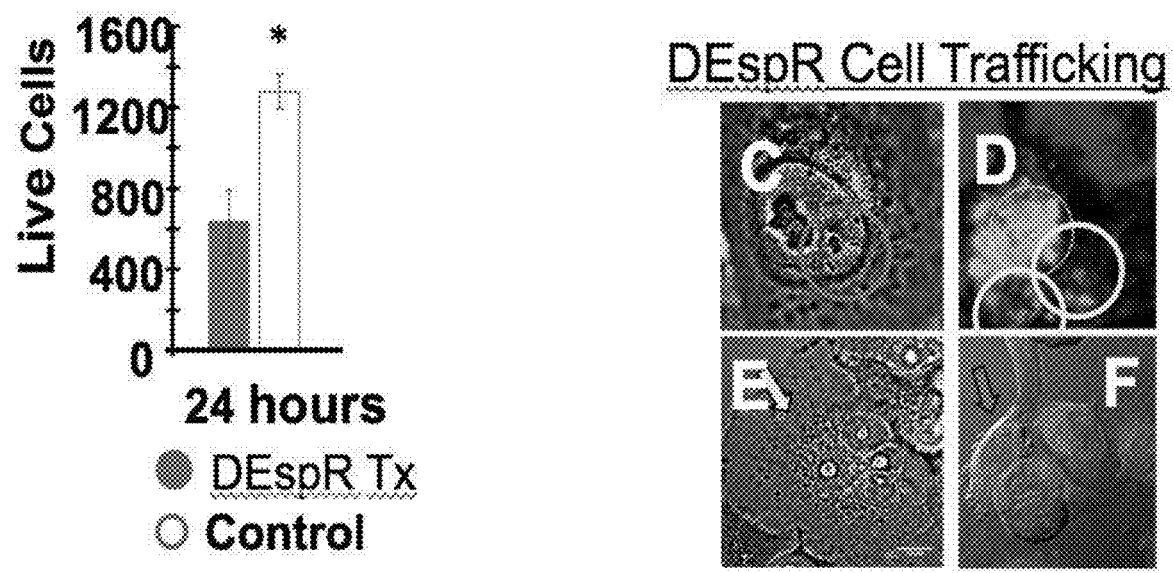
Fig 20B
Figs. 20C-20F

NetOGlyc 4.0 Server - prediction results

Technical University of Denmark

SITCIICFTCVGSQLSMSSS

```
##gff-version 2
##source-version NetOGlyc 4.0.0.13
##date 18-7-31
##Type Protein
#seqname       source          feature  start   end    score  strand  frame  comment
SEQUENCE       netOGlyc-4.0.0.13   CARBOHYD   1      1                            1.52422e-06
SEQUENCE       netOGlyc-4.0.0.13   CARBOHYD   3      3                            5.11498e-07
SEQUENCE       netOGlyc-4.0.0.13   CARBOHYD   9      9                            5.05571e-07
SEQUENCE       netOGlyc-4.0.0.13   CARBOHYD   13     13                           6.7628e-06
SEQUENCE       netOGlyc-4.0.0.13   CARBOHYD   16     16                           1.67677e-05
SEQUENCE       netOGlyc-4.0.0.13   CARBOHYD   18     18                           0.00524215
SEQUENCE       netOGlyc-4.0.0.13   CARBOHYD   19     19                           0.00811892
SEQUENCE       netOGlyc-4.0.0.13   CARBOHYD   20     20                           0.00583901
```

Fig. 27

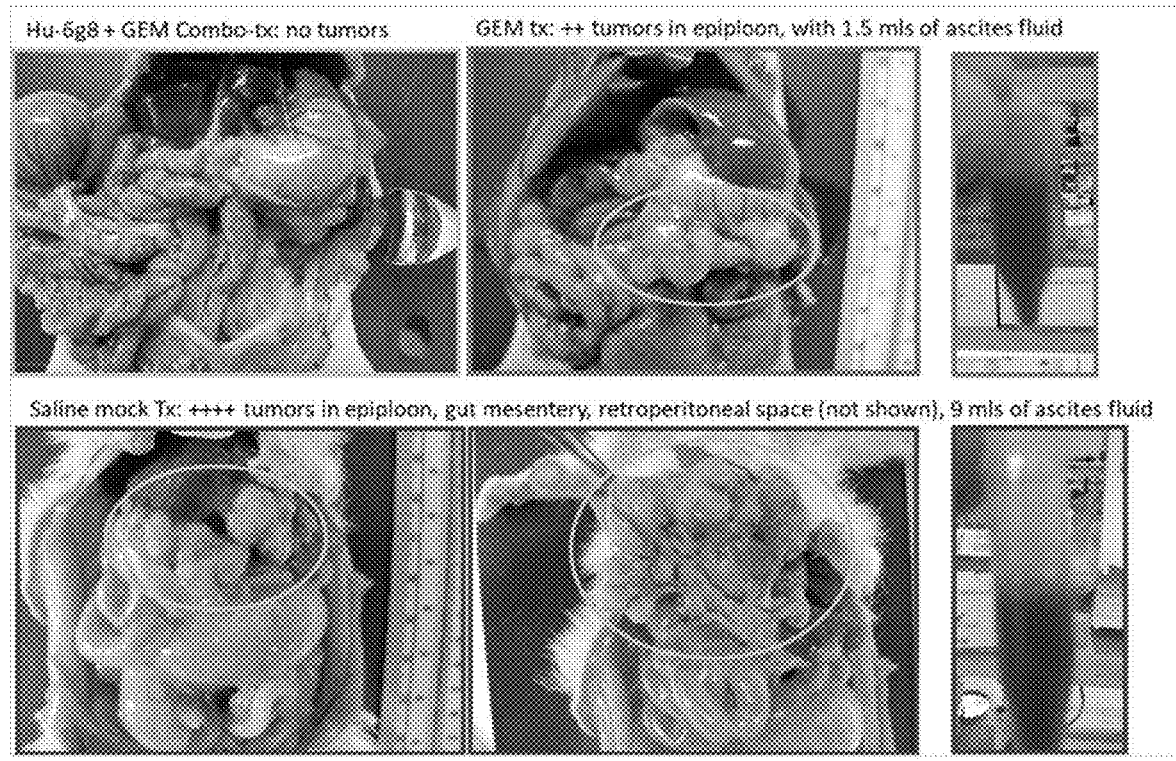
Fig. 36
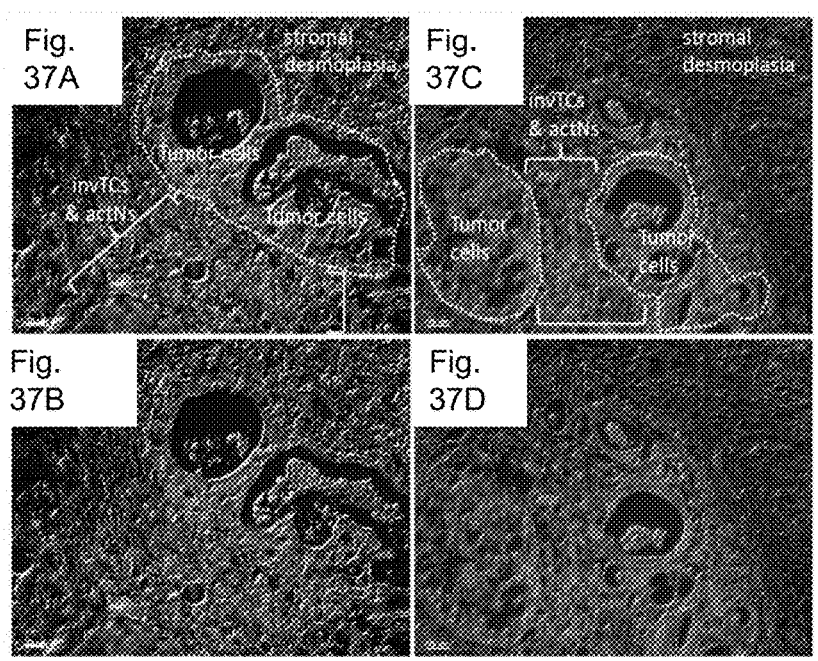

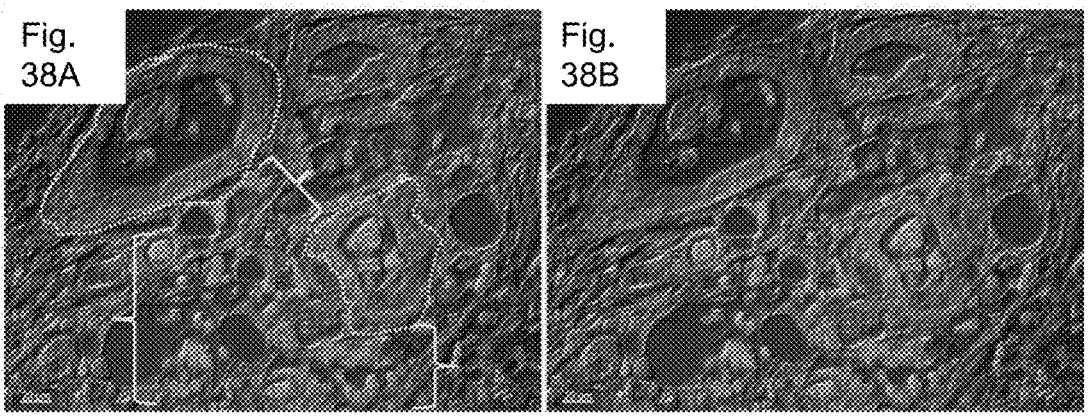
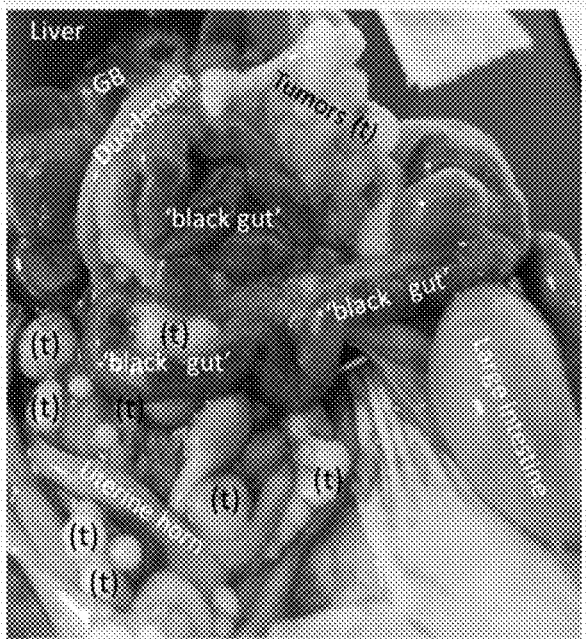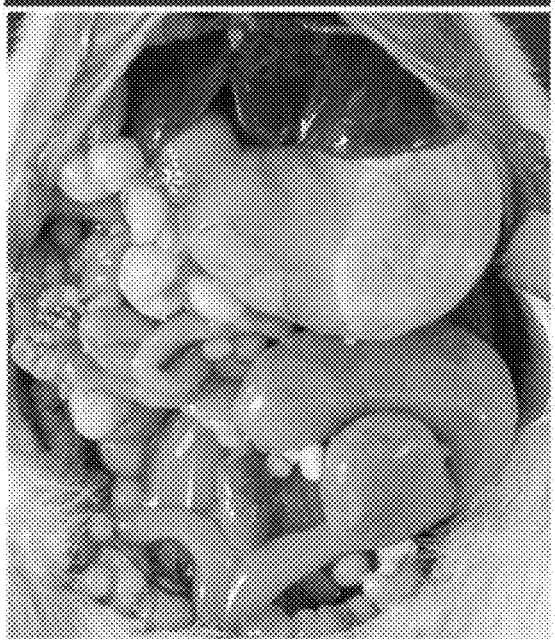
Fig. 39

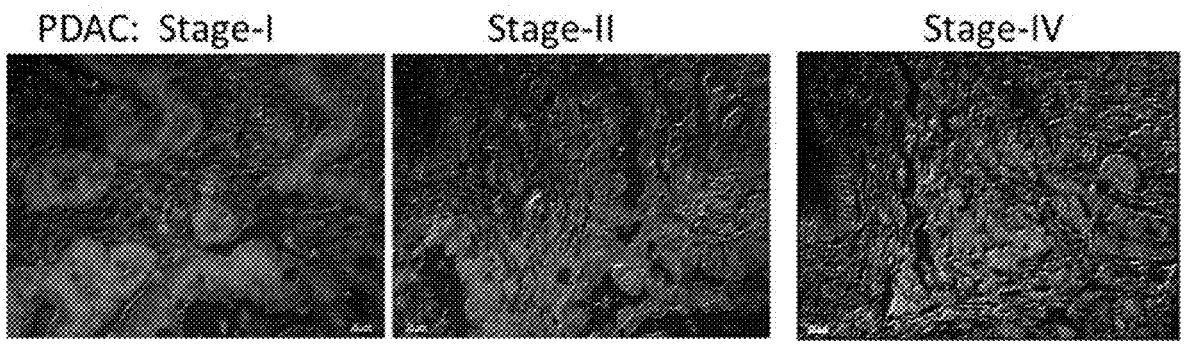
Fig. 40
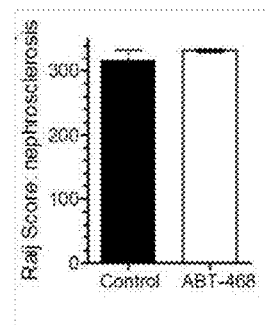
Fig. 41A
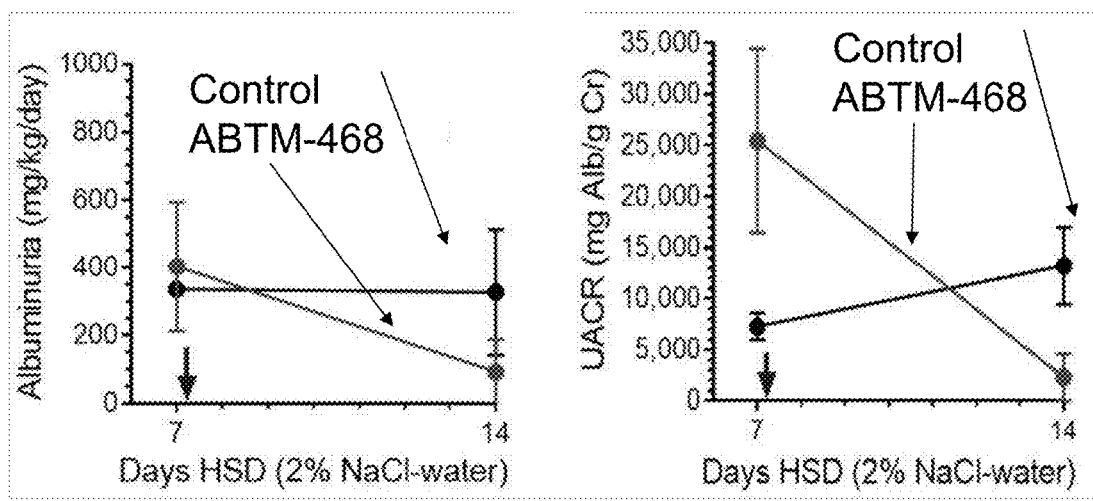
Fig. 41BFig. 41C

US 10,849,966 B2

METHODS FOR TREATING NETOSIS AND NEUTROPHIL ACTIVATION

CROSS-REFERENCE TO RELATED APPLICATIONS

This application claims benefit under 35 U.S.C. § 119(e) of U.S. Provisional Application No. 62/559,874 filed Sep. 18, 2017 and 62/685,377 filed Jun. 15, 2018, the contents of which are incorporated herein by reference in their entireties.

GOVERNMENT SUPPORT

This invention was made with government support under Grant No. T32EB006359 awarded by the National Institutes of Health. The government has certain rights in the invention.

TECHNICAL FIELD

The technology described herein relates to methods of treating NETosis and neutrophil-associated pathologies.

BACKGROUND

The most common type of blood cells—polynuclear morphogenic neutrophils (PMNs) are very short-lived, usually lasting only mere hours in the bloodstream. During reactions to injury and/or infection, these PMNs are activated in order to kill bacterial cells and their lives are extended as part of this activation process. In parallel, during reactions to injury wherein damage associated molecular patterns (DAMPS) are released, PMNs are also activated in order to initiate wound healing, and live longer, from mere hours to days. However, dysregulated activated PMNs can be lethal or injurious to the host itself, not just to bacteria, leading to vicious cycles of neutrophil-driven secondary (2°) tissue injury, referred to as the neutrophil paradox. Weiss, S. J. 1989. Tissue destruction by neutrophils. N. Engl. J. Med. 320:365-376. This is particularly problematic when activated PMNs persist without resolution, leading to a) self-amplifying cycles of tissue injury and PMN activation that can lead to death, or to b) reciprocal interactions that advance or exacerbate chronic conditions, or lead to immune-evasion.

Normally, an activated PMN is able to turn-off itself upon reaching its target site (site of injury or pathogen) and initiate the process of 'active resolution.' However, when the activated PMN does not turn itself off or becomes dysregulated, this leads to self-sustaining vicious cycles of neutrophil-driven secondary (2°) tissue injury or exacerbations in chronic disease. How to turn off or neutralize neutrophil-driven 2° tissue injury without causing further damage or inducing new problems remains a major challenge. There are no FDA-approved therapies that are able to stop vicious cycles of neutrophil-driven 2° injury in the acute crises or in chronic disease or exacerbation bouts of chronic disease.

Emerging data implicate neutrophil extracellular traps (NETs), in addition to activated PMNs, as key players in neutrophil-driven secondary (2°) tissue injury. NETosis, the process of extruding NETs by PMNs can be a form of PMN cell death, or can occur as vital NETosis wherein the PMN stays alive. Because of the biophysical properties of NETs, they can induce direct injury of tissue (e.g., blood brain barrier disruption), as well as worsen injury (e.g., brain trauma) or pathologies (e.g., vasculitis, atherothrombosis). such as vascular occlusion and thromboses.

Ways to counteract problematic activated PMNs are of considerable interest in treating a number of conditions in which the immune system is misregulated (e.g., autoimmune diseases or cancer), as well as in conditions which are particularly associated with activated PMN damage causing life-threatening secondary tissue injury or exacerbations of chronic diseases (e.g., COPD, sickle cell crises, cystic fibrosis, diabetes, systemic lupus erythematosus). Ways of preventing or averting NETosis or neutralizing NETs are also of considerable interest.

To date, there is no therapy that can avert or stop activated PMN-driven tissue injury or systemic organ dysfunction or chronic disease exacerbation, or NETs-associated tissue injury. Stopping neutrophils and/or NETs without inhibiting or activating other types of white blood cells, or activating neutrophils further, or activating complement system, or disturbing the coagulation system has not been achieved.

SUMMARY

As described herein, the inventors have found that agents which can bind specifically to DEspR can block or reverse the prolonged lifespan of activated PMNs. In one embodiment, humanized antibodies referred to herein as anti-DEspR antibodies can block or reverse the prolonged lifespan of actPMNs. Accordingly, the methods described herein permit rapid functional shutdown and clearance of dysregulated activated PMNs and can reduce or prevent the deleterious side effects (e.g., tissue injury and/or organ dysfunction) caused by dysregulated, e.g., excessive, PMN activation without deleterious side effects on other vital organs or vital functions.

In one aspect of any of the embodiments, described herein is a method of decreasing the survival and/or activity of a neutrophil, the method comprising contacting the neutrophil with a DEspR inhibitor. In one aspect of any of the embodiments, described herein is a method of preventing or decreasing neutrophil extracellular trap (NET) release or actPMN NETosis or vital NETosis in a subject in need thereof, the method comprising administering a therapeutically effective amount of a DEspR inhibitor to the subject.

In some embodiments of any of the aspects, the neutrophil is an activated neutrophil (actPMN).

In one aspect of any of the embodiments, described herein is a method of preventing or decreasing NET release or actPMN NETosis or vital NETosis in a subject in need thereof, the method comprising administering a therapeutically effective amount of an anti-DEspR antibody reagent conjugated to an anti-neutrophil or anti-NET reagent.

In some embodiments of any of the aspects, the DEspR inhibitor is an anti-DEspR antibody reagent or an antigen-binding fragment thereof. In some embodiments of any of the aspects, the anti-DEspR antibody reagent is a monoclonal antibody or an antigen-binding fragment thereof. In some embodiments of any of the aspects, the anti-DEspR antibody reagent is a bi-specific reagent that can bind specifically to i) DEspR and ii) PD1 or PD-L1.

In some embodiments of any of the aspects, the antibody reagent has complementary determining regions selected from SEQ ID Nos: 1-3, 9-11, 17-19, 5-7, 13-15, 21-23, 25-27, 29-31, and 33-35.

In some embodiments of any of the aspects, the subject is in need of treatment for a condition or disease wherein neutrophils contribute to pathogenesis or worsening of disease. In some embodiments of any of the aspects, the condition or disease is selected from the group consisting of: systemic inflammatory response syndrome (SIRS); acute lung injury (ALI); acute respiratory distress syndrome (ARDS); multi-organ failure or multi-organ dysfunction syndrome (MODS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endothelial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis.

In some embodiments of any of the aspects, the subject is in need of treatment for cancer and has a PD-L1+/DespR+ tumor.

In some embodiments of any of the aspects, the subject is in need of treatment for cancer and has previously been treated by tumor resection. In some embodiments of any of the aspects, the subject is further administered a further immunotherapy. In some embodiments of any of the aspects, the subject has previously been administered a further immunotherapy. In some embodiments of any of the aspects, the subject is resistant to treatment with a further immunotherapy. In some embodiments of any of the aspects, the subject has developed a toxicity from treatment with a further immunotherapy. In some embodiments of any of the aspects, the immunotherapy is a PD1 and/or PD-L1 inhibitor therapy. or co-stimulator therapy.

In some embodiments of any of the aspects, the subject is a mammal. In some embodiments of any of the aspects, the subject is a human.

BRIEF DESCRIPTION OF THE DRAWINGS

FIG. 1A) Representative image of human activated neutrophils immunostained with 6g8 mumab fluorescently labeled with AF568; DAPI nuclear stain. FIG. 1B) Isotype control is negative demonstrating specificity of anti-DEspR immunostaining for DEspR expression. FIG. 1C) anti-DEspR 6g8 mumab immunostaining of human neutrophils undergoing NETosis. DAPI stains extruded DNA. FIG. 1D) Hi-magnification view of NETs, and reference published image of NET with DNA stained by SYTOX green (inset).

FIG. 2A) FACS analysis of CD11b activated neutrophils that are DEspR+(bold oval), and DEspR[−] (bold circle). Quiescent neutrophils are DEspR[−] and CD11B[−] in Quadrant Q4. FIG. 2B depicts inhibition of the extended survival of activated neutrophils by two different anti-DEspR mAbs targeting two different epitopes on DEspR.

FIGS. 3A-3F demonstrate in vivo efficacy analysis of anti-DEspR mAb therapy in a model of non-infectious excessive activated-neutrophil-mediated hemorrhagic encephalopathy (HgeEnc). FIG. 3A) control rat brain after PBS-buffer perfusion to eliminate intravascular blood. FIG. 3B) non-treated rat brain exhibiting global hemorrhagic encephalitis 24-hours after infusion of low-dose lipopolysaccharide (LPS) iv. FIG. 3C) Anti-DEspR treated rat brain with minimal to no hemorrhagic encephalitis (1 mg/kg/dose iv given shortly after infusion of LPS). FIG. 3D) ELISA analysis of brain membrane proteins demonstrating no murine IgG in brains from two control groups: Lane C, normal control, i.e., with no LPS-induced encephalopathy, and Lane 1, untreated control with LPS-induced encephalopathy, in contrast to anti-DEspR murine mAb treated rat brains, Lanes 2 and 3, both of which exhibit murine IgG levels. Notably, anti-DEspR 6g8 exhibits greater brain levels than anti-DEspR 10a3. FIG. 3E) ELISA analysis of neutrophil myeloperoxidase (MPO) levels in the brain comparing normal (laneC), non-treated Hge-Enc brains (Lane 1), and response to anti-DEspR treatment of two murine mAbs targeting different DEspR epitopes (lanes 2,3) shows decreased MPO levels in the brain, thus indicating anti-DEspR efficacy to inhibit activated neutrophil infiltrates in the brain. FIG. 3F) ELISA analysis of rat-specific albumin demonstrates decreased albumin levels in both anti-DEspR (10a3, 6g8) mAb-treated rats consistent with decreased brain edema marked by decreased influx of albumin.

FIG. 15 demonstrates that anti-DEspR induces apoptosis in Panc1 tumor cells within 2 hours from application. Panel CSCs plated, exposed to AF568-labeled (*) anti-DEspR 7c5* or isotype IgG* in culture media, washed, fixed and mounted with DAPI at designated timepoints: 1-, and 2 hours (hr). CSCs, cancer stem-like cells. DAPI, DNA nuclear stain, and AF568. Reference images taken from: Malorni et al., Archana et al 2013.

FIGS. 17A-17C depict anti-DEspR-mab (hu6g8 mab). FIG. 17A depicts a diagram of DEspR, murine precursor mabs and humanized IgG and IgG4 mabs. Hu6g8 is notated as 6g8g7-hu-IgG4 raised against epitope 2, spanning the putative binding domain. FIG. 17B depicts a graph of hu6g8 binding to DEspR on intact human cells done in triplicate, EC50 4.2 nM for hu-6g8; vs EC50 178 nM for murine precursor mu-6g8. FIG. 17C depicts a graph of the inhibition of neutrophil (PMN) survival: hu6g8 IC50 7.7 nM vs IC50>198 nM for mu-6g8 mab

FIG. 19E depicts the tumor proportion score of PDAC samples (n=133), FIG. 19F depicts a graph fof the fraction of DEspR [+] cells in invading margins of tumor samples. (n=77). DEspR Expression on PDAC cells: (FIG.

Figures 19A, 19B, 19C, 19D:
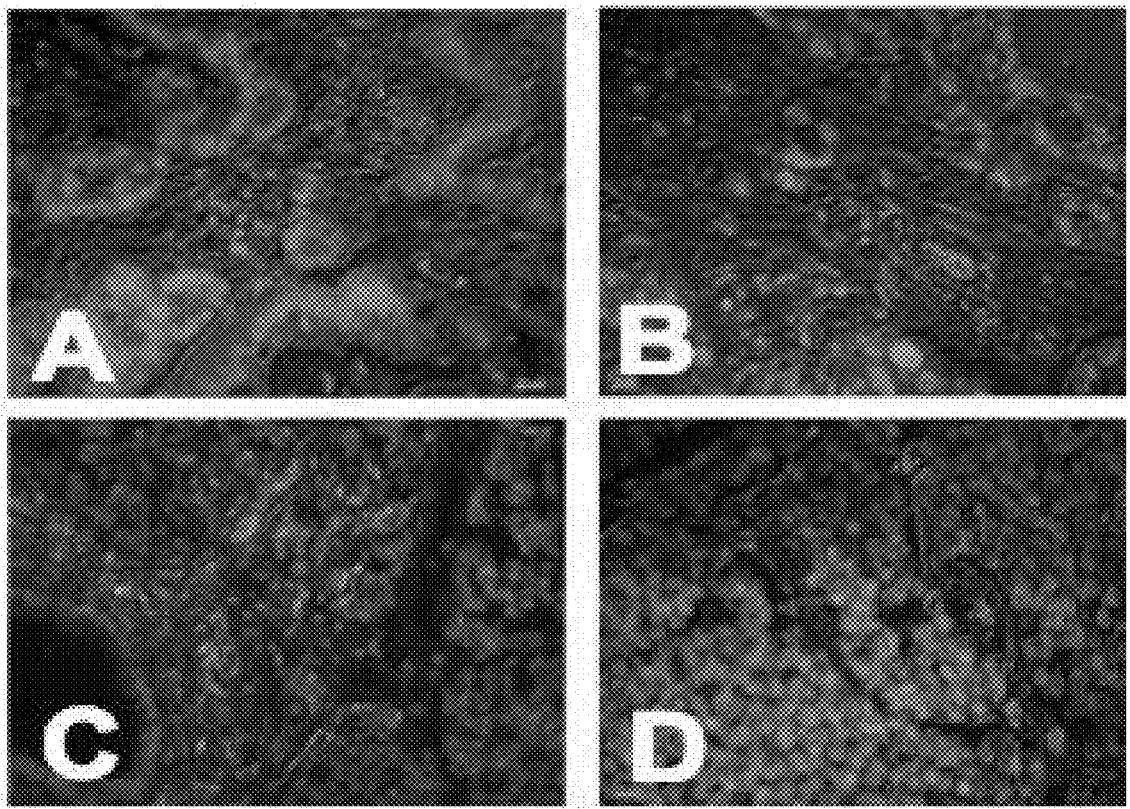
FIGS. 19A-19J depict DEspR expression in PDAC tissue and lines. Fluorescent labeling of human PDAC tissue is depicted for (FIG. 19A) Stage IIB PDAC, (FIG. 19B) Stage IV PDAC, (FIG. 19C) normal pancreas, (FIG. 19D) PDAC: hepatic mets.
Figure 19E:
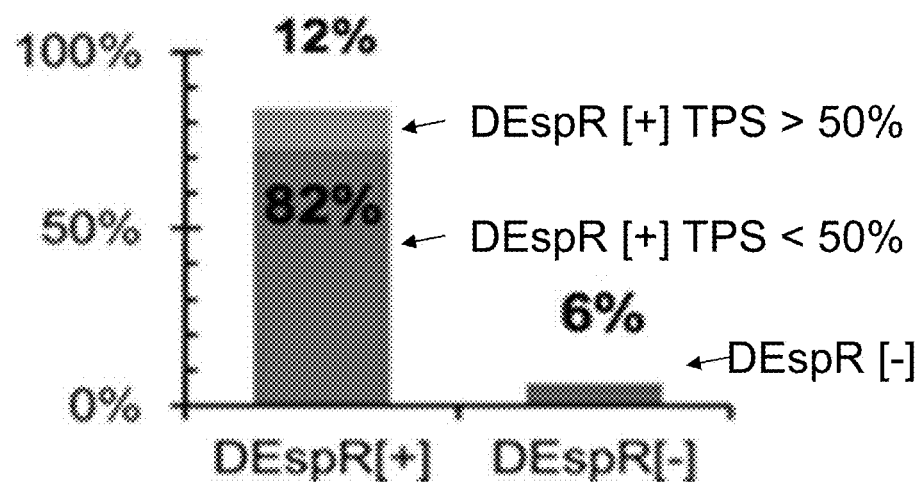
Figure 19F:
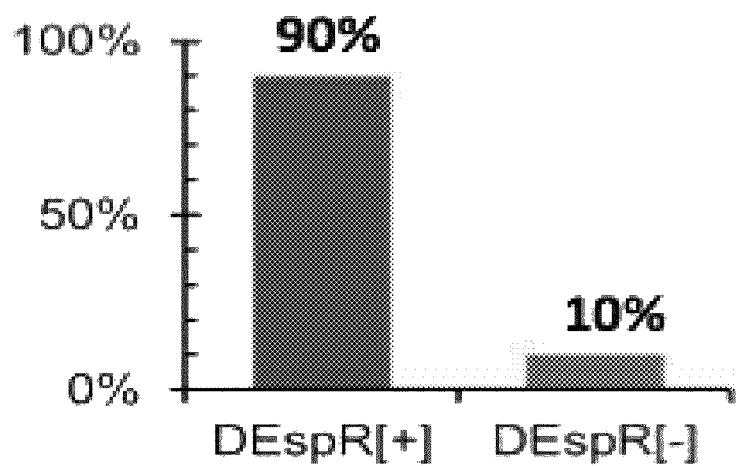
Figures 19G, 19H, 19I, 19J:
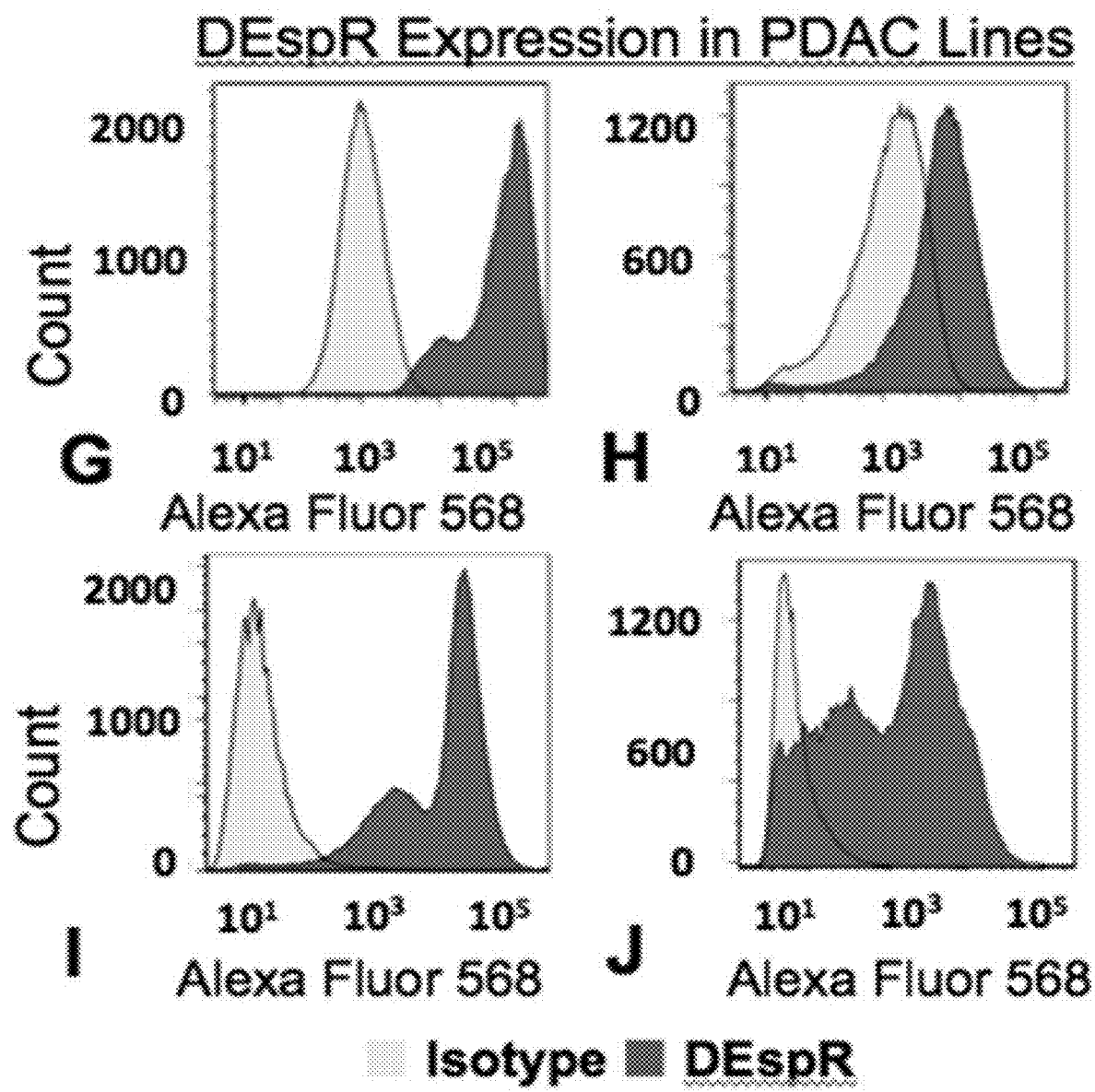

19G) Panel non-CSCs (FIG. 19H) Panel CSCs (FIG. 19I) MIA PaCa2 non-CSCs (FIG. 19J) MIA PaCa2 CSCs.

FIGS. 20A-20F. Panc1 cell viability under (FIG. 20A) basal and (FIG. 20B) low pH with anti-DEspR therapy is depicted. Endocytosis of DEspR-humabAF-568, showed nuclear colocalization by 1hr (FIG. 20C), lysosomal colocalization by 1hr (FIG. 20D), necroptotic (arrow) (FIG. 20E) and apoptotic (arrow) (FIG. 20F) morphology by 1 hr.

Figure 21:
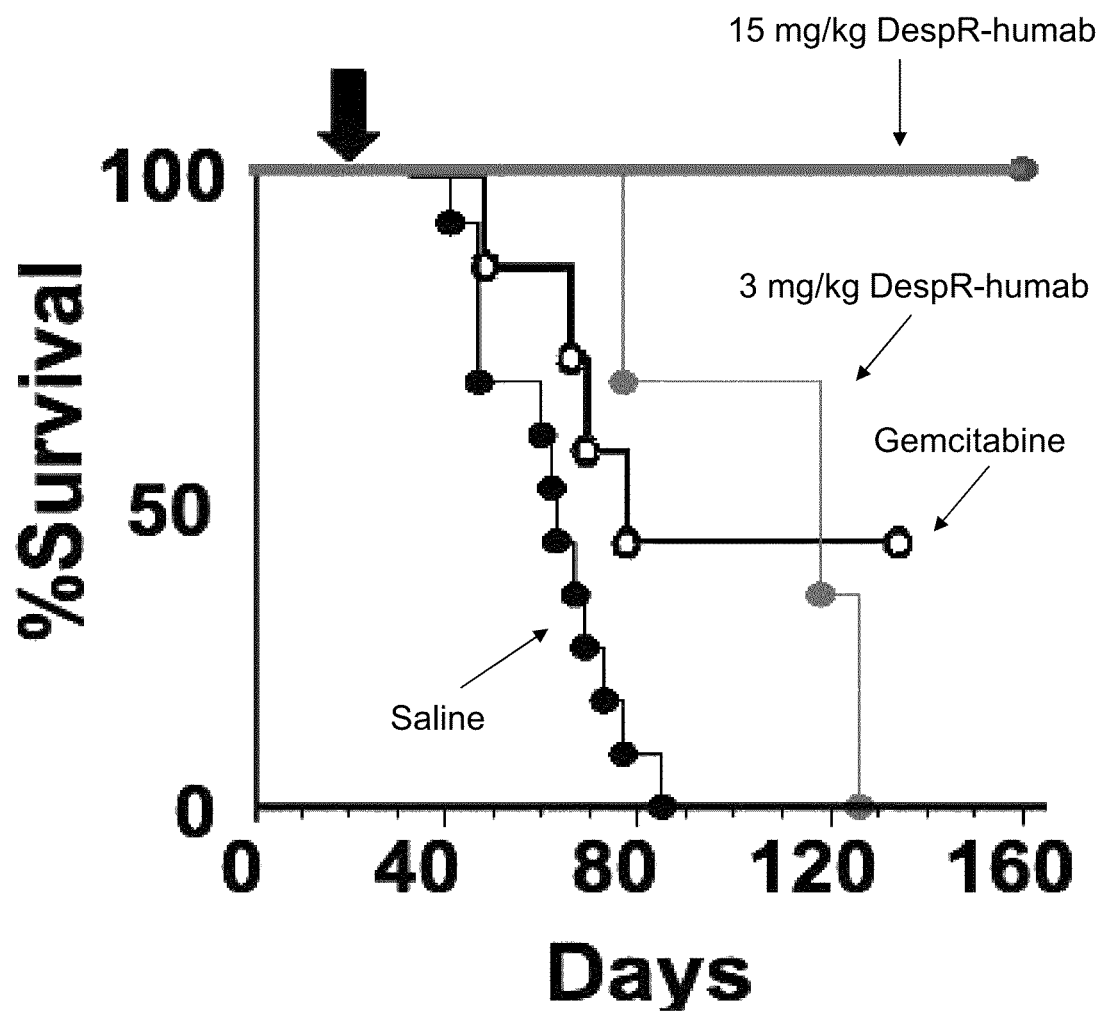

FIG. 21 depicts a survival graph of a Panc1 xenograft model showing increased survival upon treatment with DEspR-humab.

Figure 22:
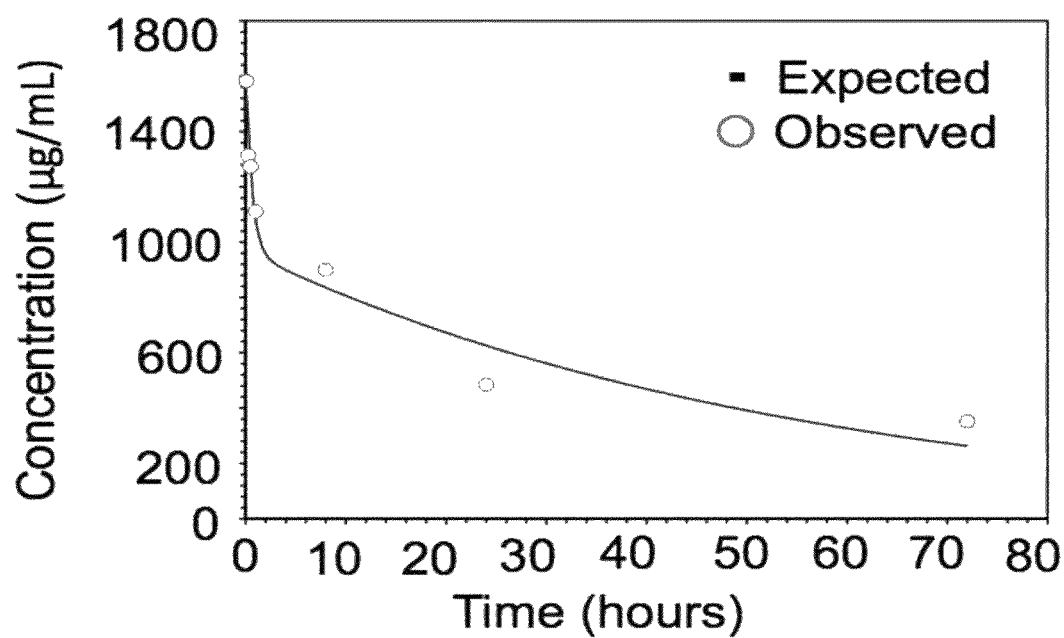

FIG. 22 depicts a PK study of DEspR-humab in Panc1 xenograft mice; 15 mg/kg i.v. (n=3); half-life=1.70 days.

Figure 23A:
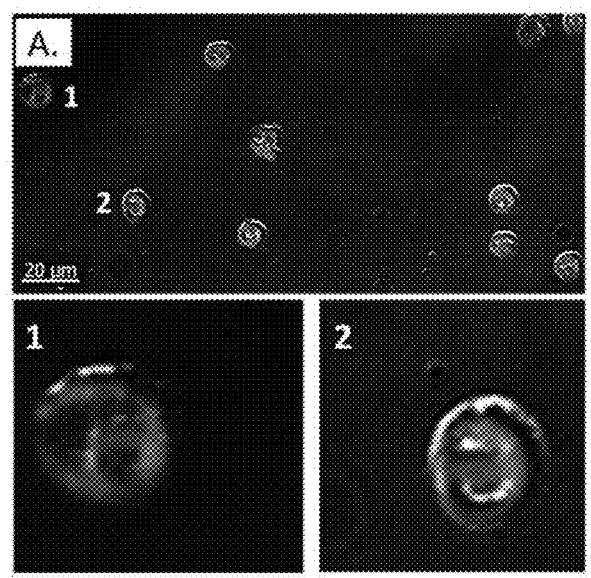
Figure 23B:
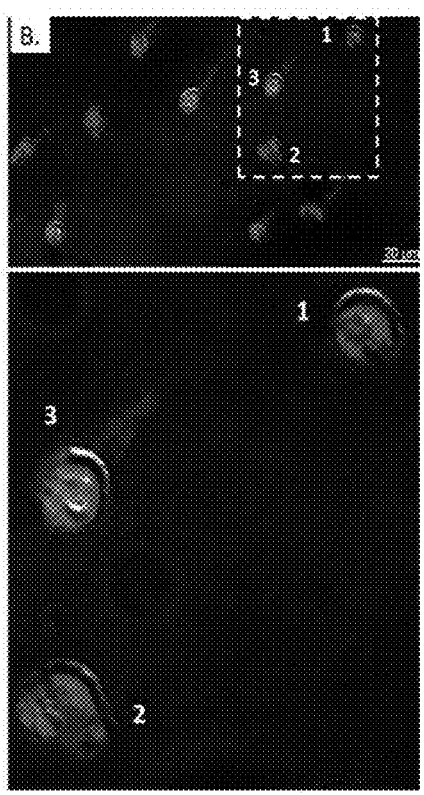

FIGS. 23A-23B depict immunofluorescence analysis of human stress-activated neutrophils shows DEspR+ expression in activated neutrophils with classical poly-lobulated nuclei (FIG. 23A) and in neutrophils undergoing NETosis (FIG. 23B). Depicted are merged images of immunocytostaining of human stress-activated neutrophils from normal human volunteers. FIG. 23A depicts activated neutrophils (actNs) DEspR+ immunostaining. 1] high mag of actNs with no NETS; 2] high mag of actNs with marginalization of DNA suggesting very early NETosis. FIG. 23B depicts ActNs undergoing vital NETosis with intact cell membrances. 1) early, 2) mid; 3) completed extrusion of DNA defining a neutrophil extracellular trap (NET).

Figure 24:
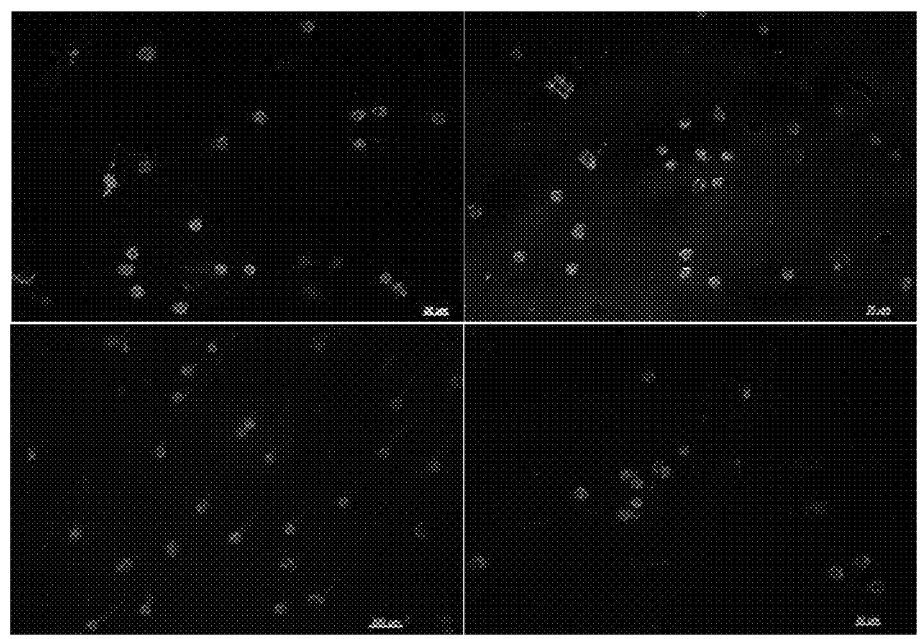

FIG. 24 depicts immunocytostaining of human stress-activated neutrophils detects DEspR+ expression in neutrophils, and in NETosing neutrophils. Notably, not all neutrophils are DEspR positive.

Figures 25, 26:
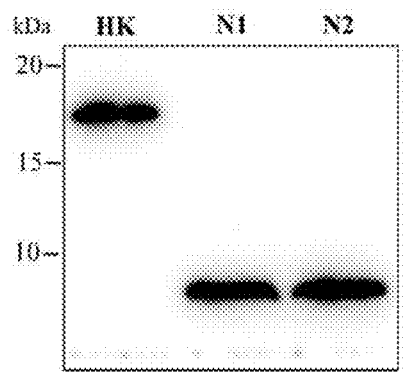

FIG. 25 depicts Western blot analysis detecting DEspR in human tissues using ABTM-468 antibody. HK, human kidney; N1, stress-activated neutrophils from normal human volunteers; N2, LPS-activated neutrophils from normal human volunteers. Molecular weight markers in kDa, kilodaltons.

FIG. 26 depicts a table of in silico analysis of serine and/or threonine phosphorylation sites in DEspR detects multiple phosphorylation sties with 3.7 to 4.3-fold greater scores than minimal cut-off values are shown in boxes. DEspR S72, and T76, 77, 84.

FIG. 27 depicts putative O-glycosylation sites in the DEspR protein. [NetOGlyc 4.0 server]. DEspR serine residues, S16, S28, S31, and threonine residues, T18, T24 are predicted O-glycosylation sites predicted with scores>threshold 0.5 [Steentoft C, et al 2013; available on the world wide web at cbs.dtu.dk]. Amino acid residues: C, cysteine I, isoleucine G, glycine L, leucine M, methionine Q, glutamine S, serine and T, threonine.

Figure 28:
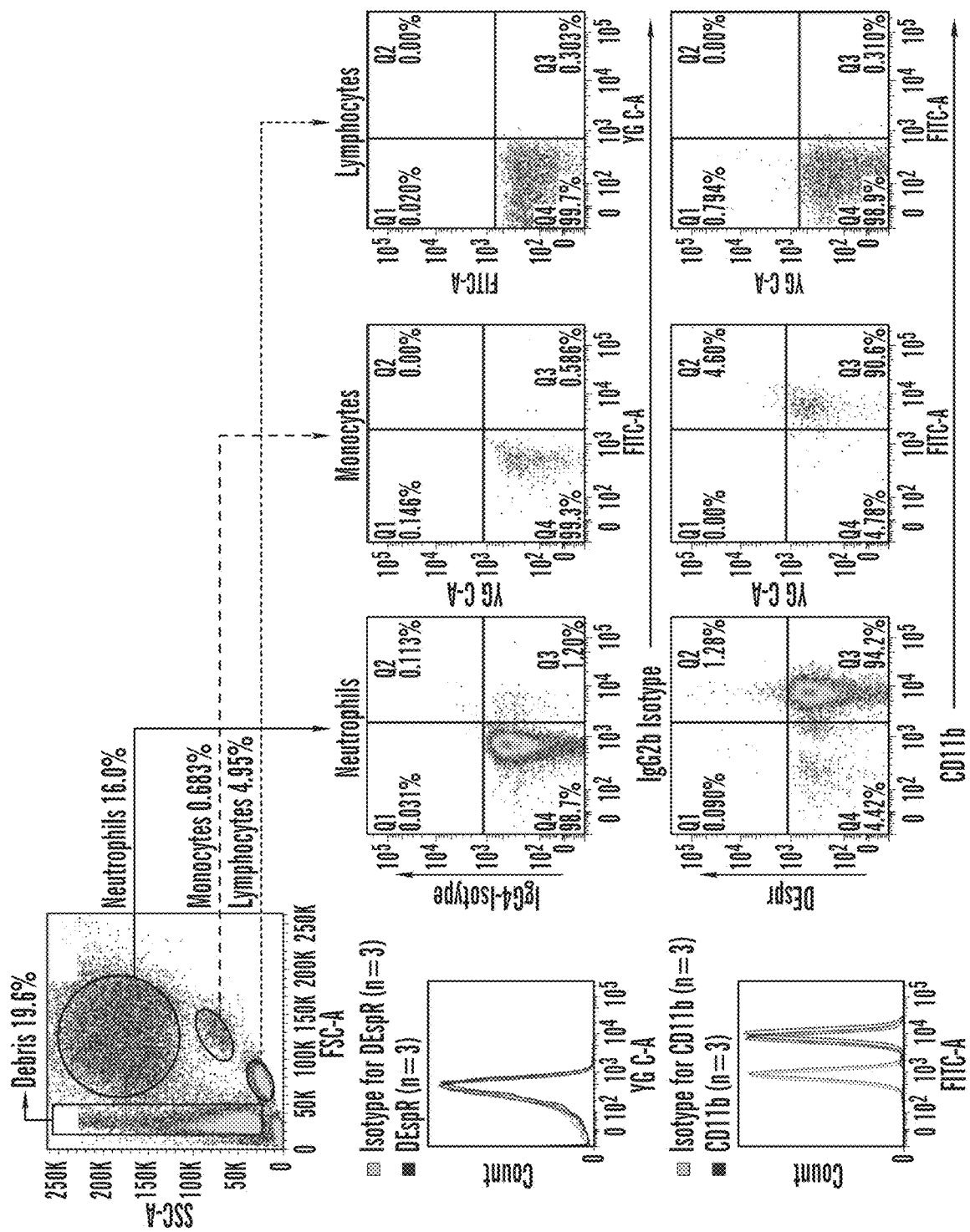

FIG. 28 depicts FACS analysis of ARDS A04 whole blood at 96 hours from diagnosis. A04 survived off vent day (d)-4, discharged day 6. Hu6g8(DEspR-AF568), CD11b-FITC. Ex vivo analysis of DEspR expression in neutrophils, monocytes, and lymphocytes in fresh whole blood sample from ARDS patients: to stimulate patient circulatory microenvironment. Gating by size (FSC) and granularity to distinguish WBC subtypes. Anti-DEspR hu-6g8 IgG4 S228PmAb (isotype control hu-IgG4). Anti-CD11b mAb (isotype control mu-IgG2b).

Figure 29:
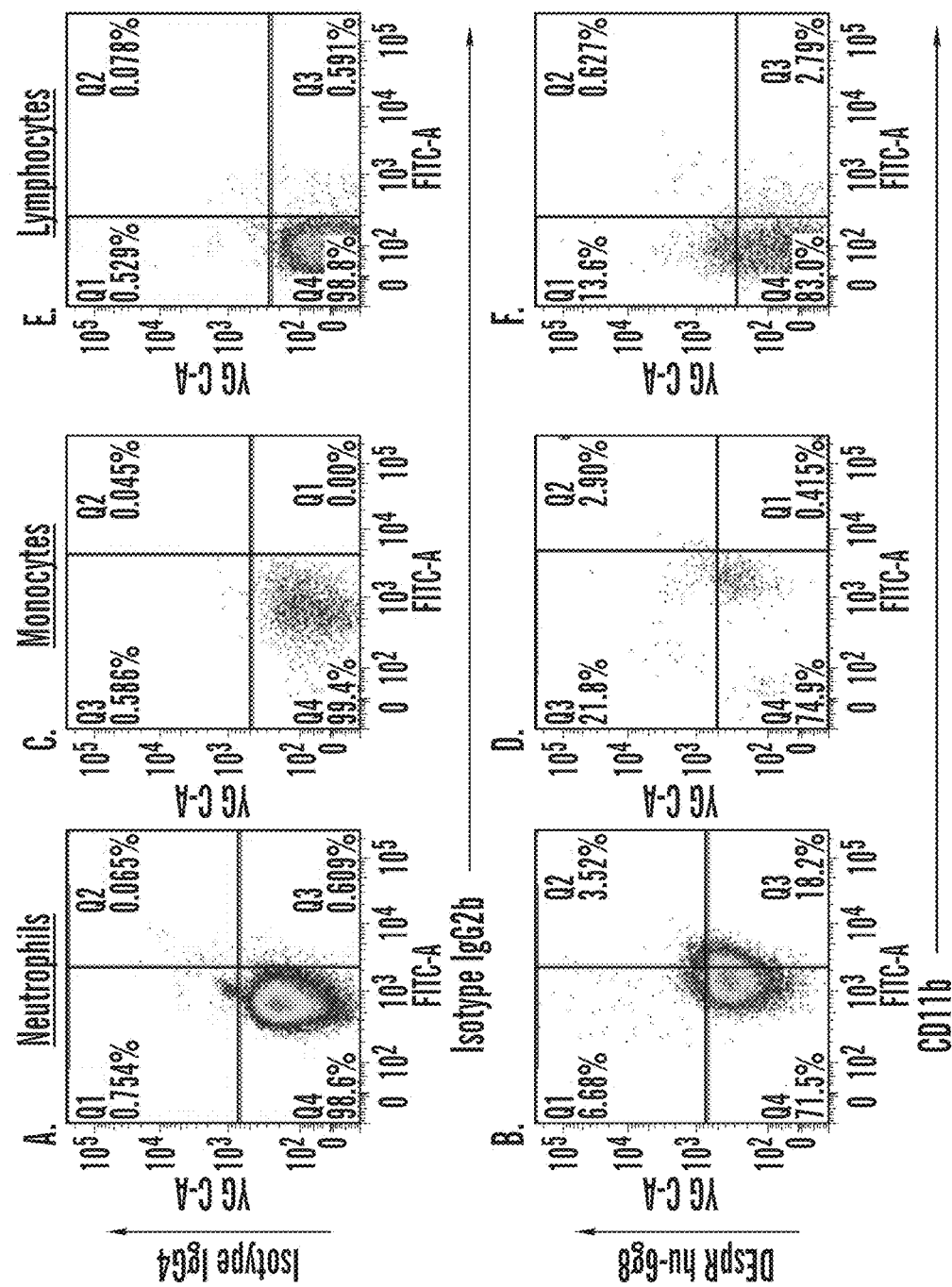
Figure 29:
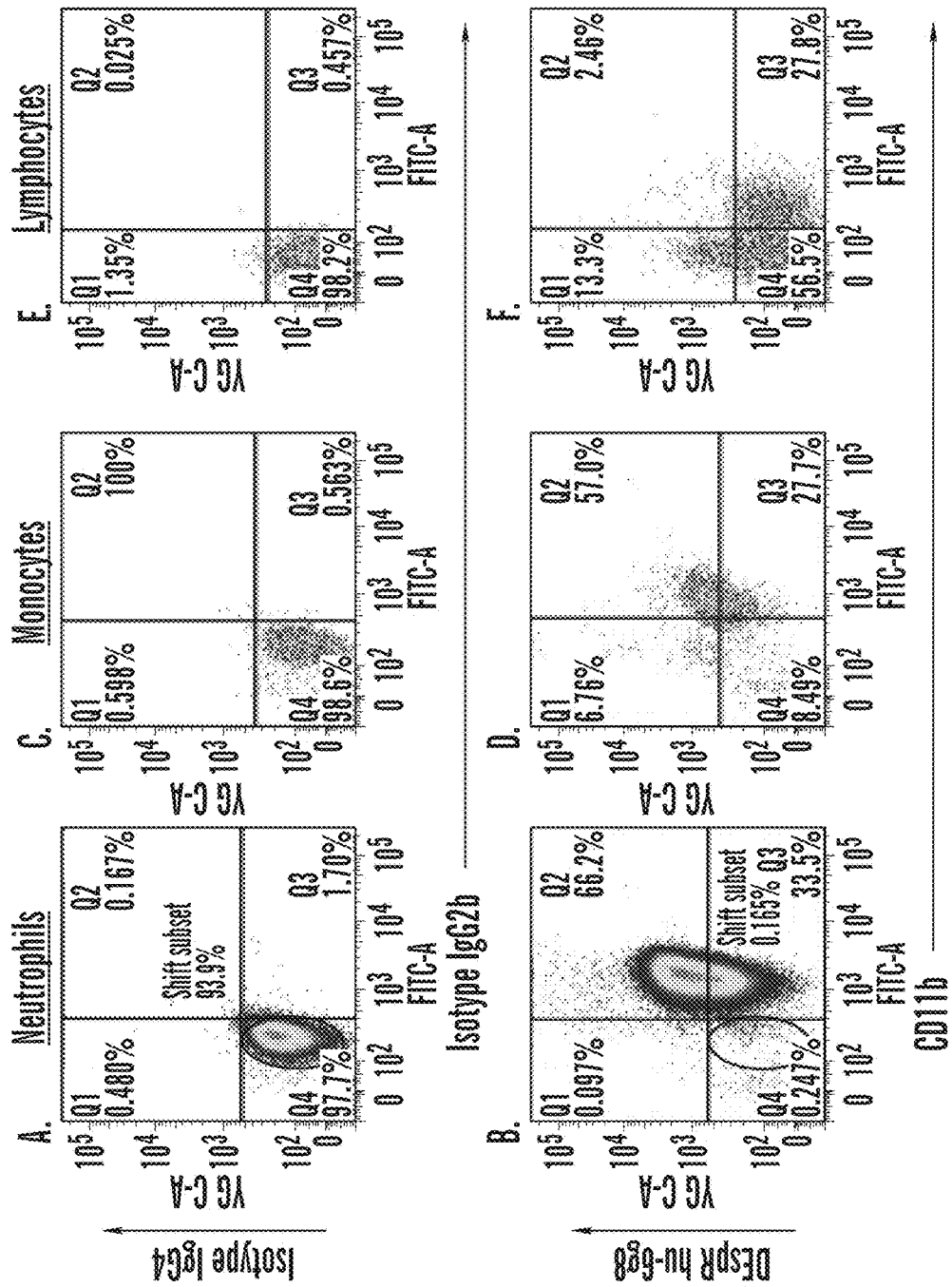

FIG. 29 demonstrates that DEspR+/CD11b+ neutrophil levels are low in ARDS patient survivors in contrast to non-survivors. Controls, AF-568 fluorescently labeled human IgG4 and AF-488 labeled murine IgG2b as isotype controls to anti-DEspR and anti-CD11b mAbs respectively. DEspR hu-6g8, anti-DEspR humanized IgG4 mAb fluorescently labeled with AF-568. CD11b, anti-CD11b murine mAb fluorescently labeled with AF488.

Figure 30:
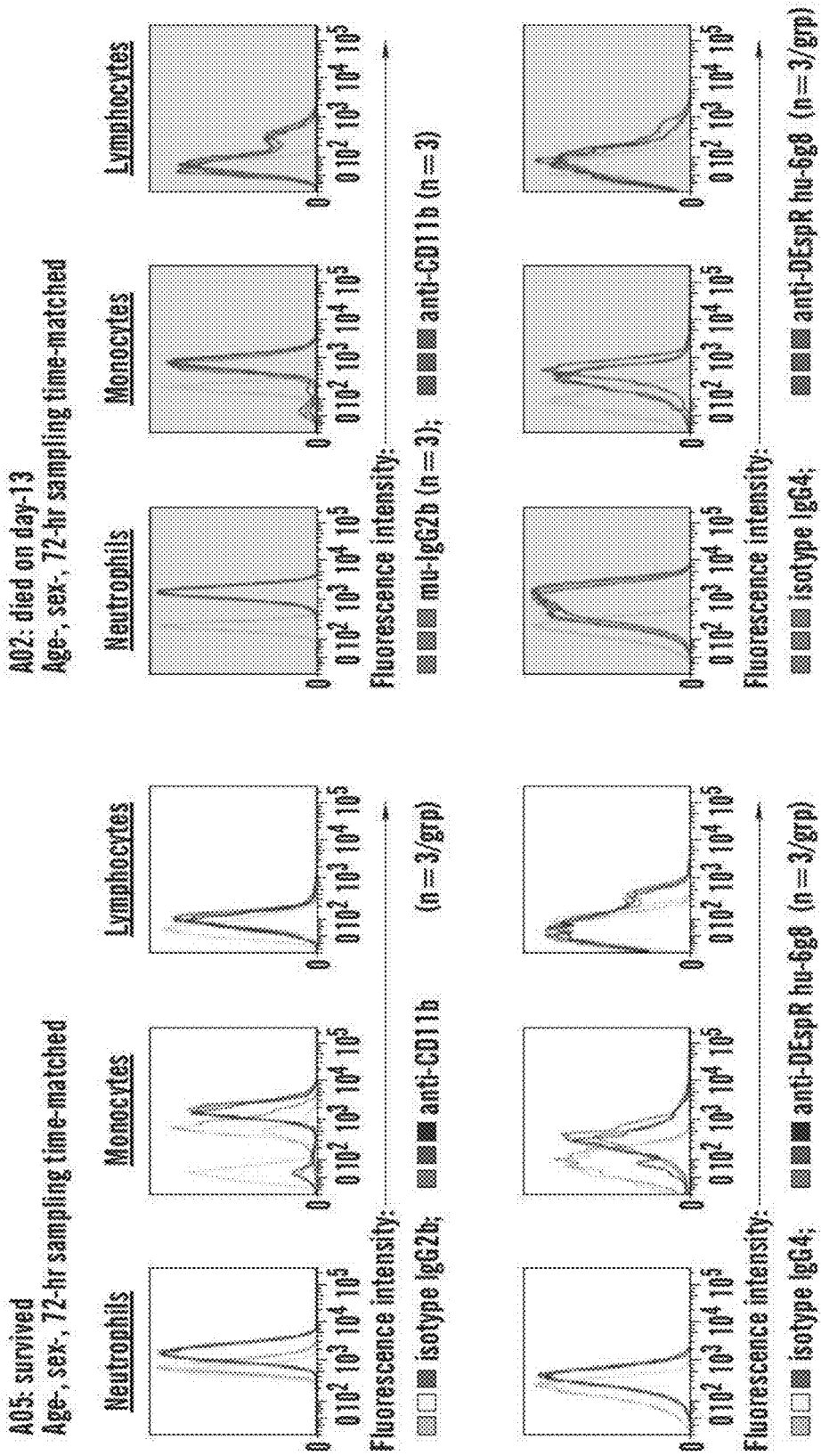

FIG. 30 depicts graphs of DEspR expression levels in the indicated cell types.

Figure 31:
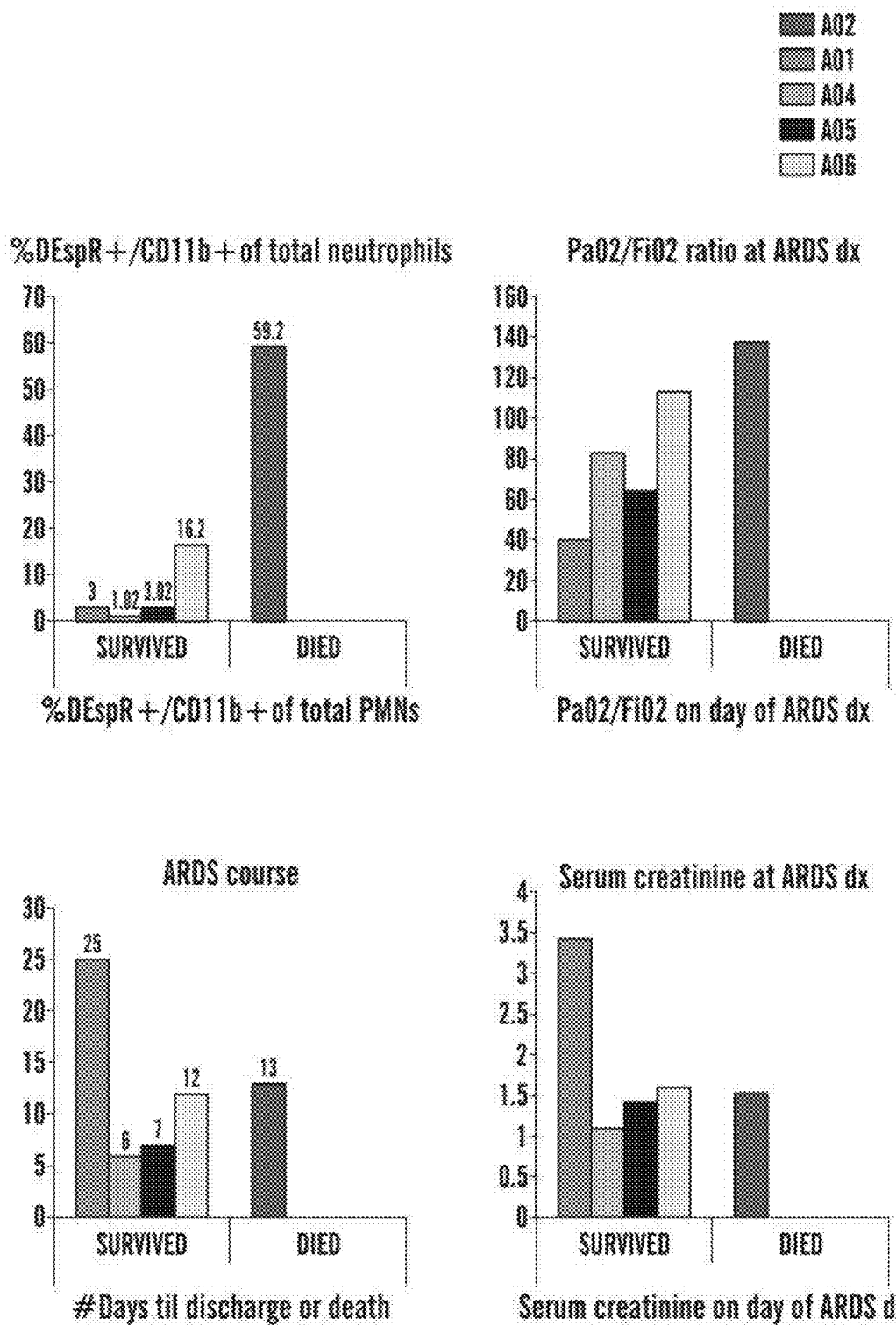

FIG. 31 depicts graphs demonstrating that the number of DEspR+/CD11b+ neutrophils is far less in ARDS survivors vs. ARDS non-survivors in contrast to other parameters. ARDS patients survivors: A01, A04, A05, A06. ARDS non-survivor: A02.

Figure 32:
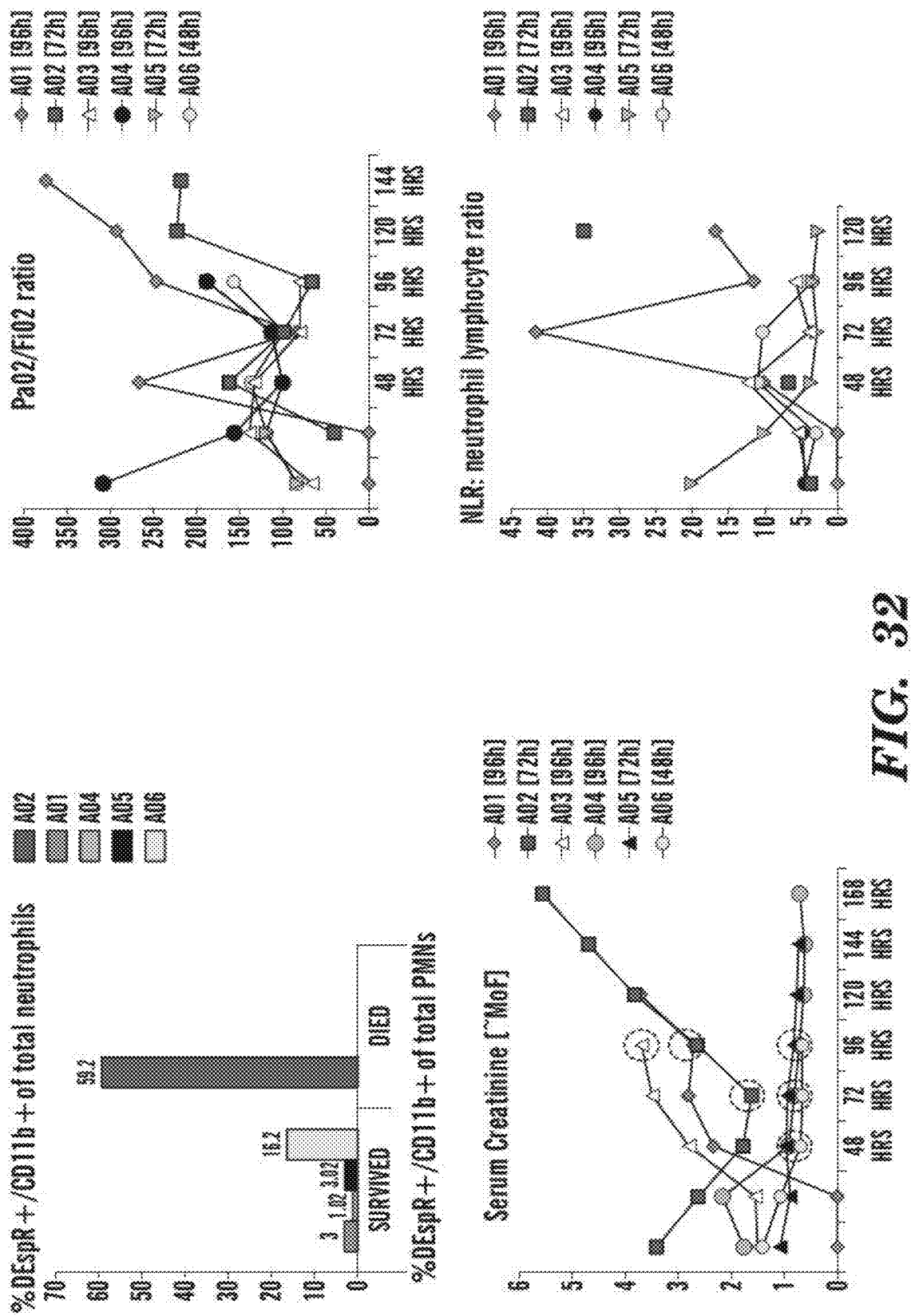

FIG. 32 depicts graphs demonstrating that the association of DEsprR+/CD11b+ neutrophils with ARDS-mortality indicates a key role in systemic tissue injury leading to multi-organ failure in ARDS patients. ARDS patients survivors: A01, A04, A05, A06. ARDS non-survivor: A02.

Figure 33:
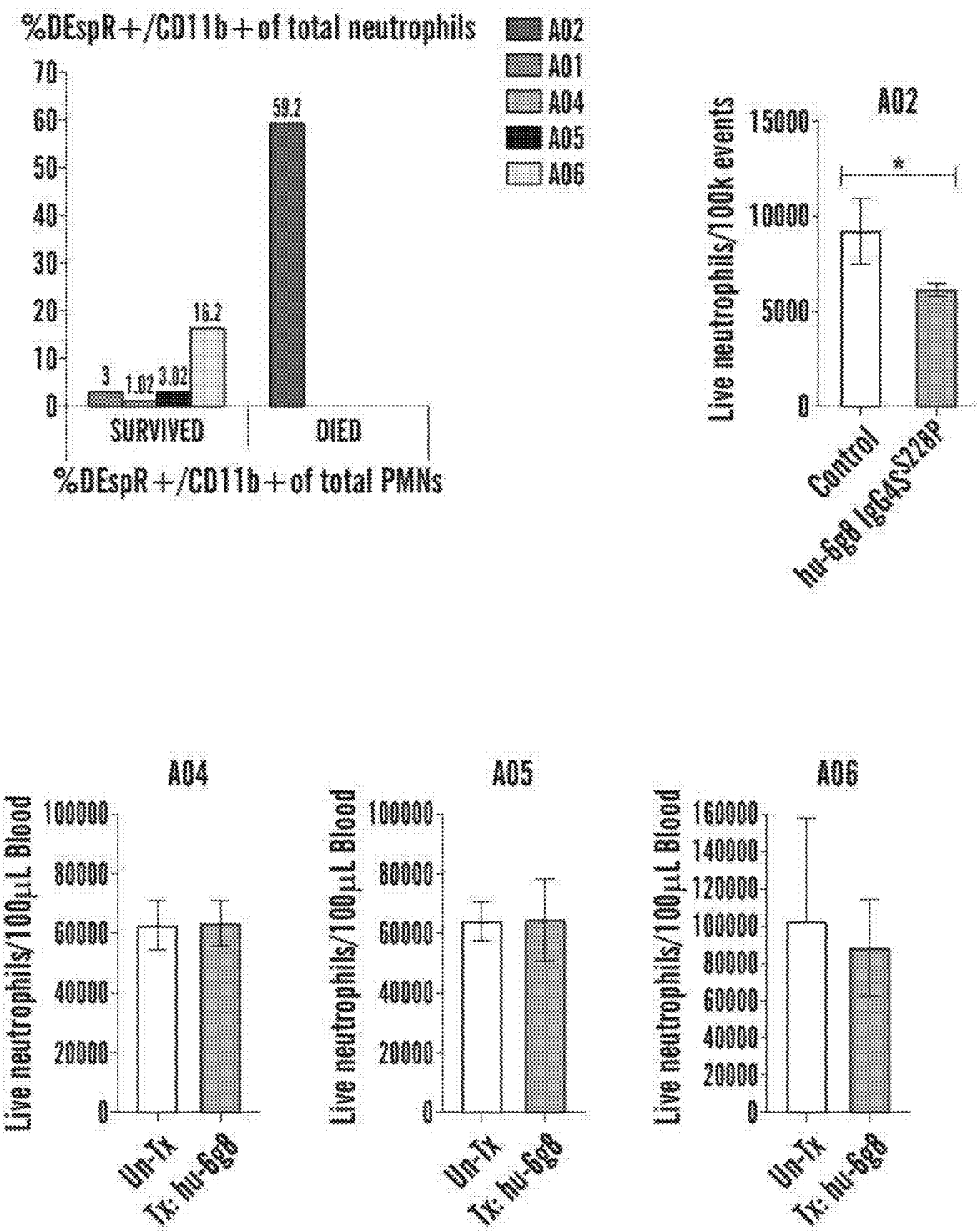

FIG. 33 depicts graphs demonstrating that ABTM-468 (hu-6g8) at 10 ug/mL decreased the number of live neutrophils ex vivo in ARDS patient blood. Neutrophils were gated for unique size/granularity properties via FSC (size) and SSC (granularity) gating. Significant decrease was detected I A02. No effects were observed in patients with low DEspR+/CD11b+ neutrophils (A04, A05, A06). FSC, forward side scatter. SSC, side scatter. N=4-5 replicates; mean+/−SD. Whole blood incubated at 37 C for 24 hours (reg incubator, rotating, in HEPES buffer) for A02 and A03. 37 C for 6 hours for A04, A05, and A06. ABTM-468(cho) at 10 ug/mL. *, P=0.0286 Mann-Whitney Rank Sum Test. ARDS patients survivors: A01, A04, A05, A06. ARDS non-survivor: A02.

Figure 34:
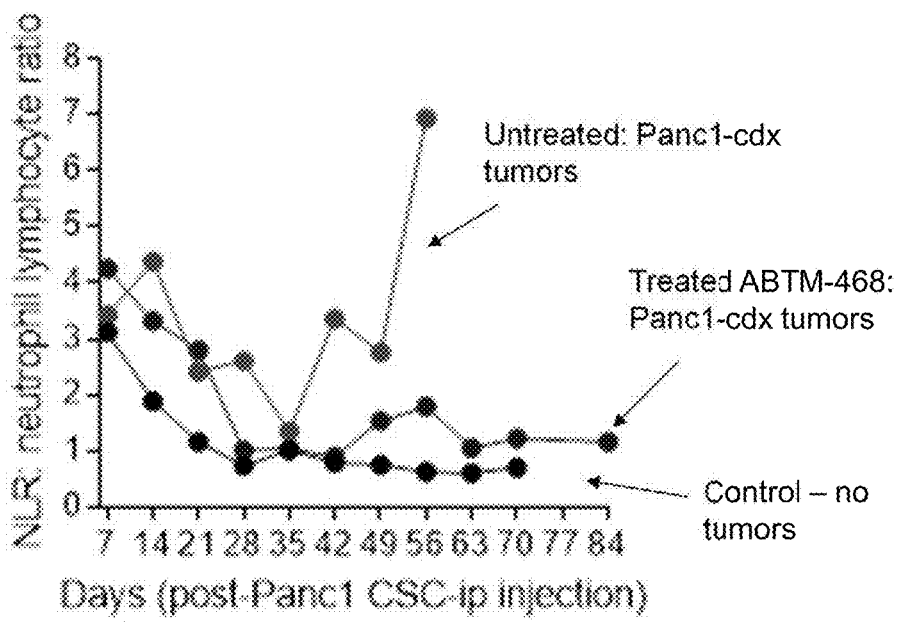
Figure 35A:
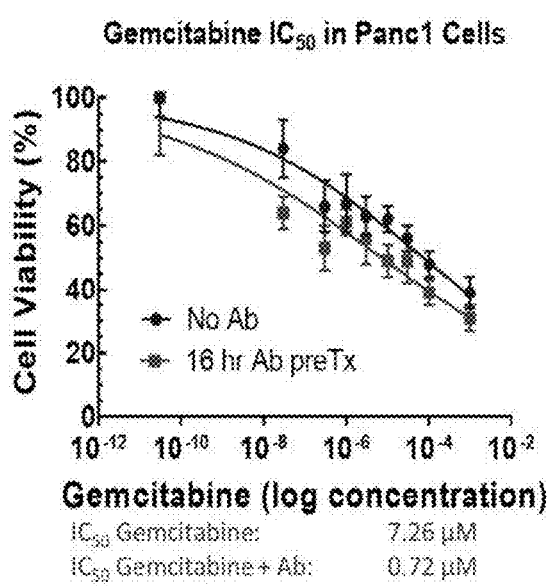
Figure 35B:
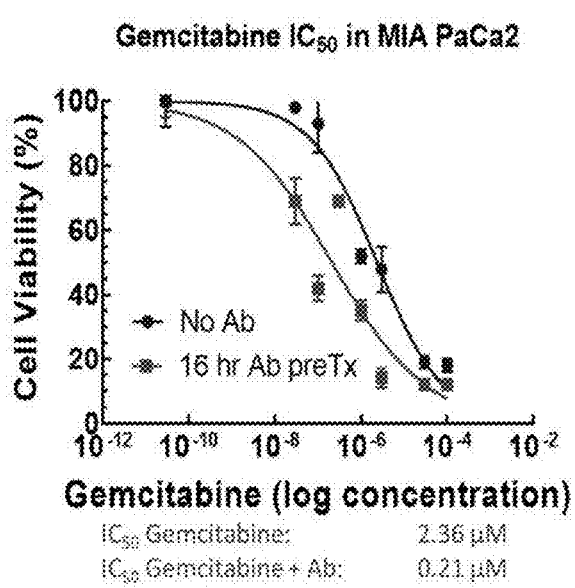

FIG. 34 depicts a graph of analysis of neutrophil-lymphocyte ratio in a xenograft rat model of human pancreatic peritoneal metastasis (Panc1-cancer stem cell CSC derived xenograft or Panc1-cdx model). ABTM-468, humanized anti-DEspR mAb 6g8-IgG4S228P FIG. 35A-35B depict graphs of in vitro testing of concentration-dependent synergy of anti-DEspR mAb induction of apoptosis in human pancreatic cancer cells (Panc1) and gemcitabine standard of care.

FIG. 36 depicts representative images of tumor treated rats with combination anti-DEspR mAb and gemcitabine vs gemcitabine alone, and mock-treated saline controls. GEM tx: gemcitabine treatment (100 mg/kg/dose iv×2). Hu-6g8 or ABTM-468: humanized anti-DEspR mAb treatment 1 mg/kg/dose iv×1/week×2. Combo-tx: combination therapy. Saline mock Tx: mock.

FIGS. 37A-37D depict representative photo-microscopy images of DEspR+ immunohistofluorescence of primary pancreatic cancer (PDAC). Tumor sections from two different patients. FIG. 37A depicts a section from the first patient. FIG. 37B is the same image without the illustrative labels. FIG. 37C depicts a section from the second patient. FIG. 37D is the same image without the illustrative labels. invTCs, invasive tumor cells; actNs, activated neutrophils. Tumor cells are characteristically larger with larger nuclei than infiltrating inflammatory cells. As DEspR is not expressed in lymphocytes or monocytes, DEspR+ inflammatory cells are NET-prone activated neutrophils and NET-ting neutrophils.

FIGS. 38A-38B depict representative immunohistofluorescent photomicrographs of DEspR+ neutrophils in the tumor stroma of pancreatic peritoneal metastatic tumor section. Tumor section is from patient-C: FIG. 38A is a panel with illustrative labels; FIG. 38B is a corresponding identical panel with no labels for unencumbered visual inspection. invTCs, invasive tumor cells; actNs, activated neutrophils, yellow brackets { } frame tumor stroma with DEspR+ invasive tumor cells and infiltrating neutrophils; white arrow points to DEspR+ tumor microvessel.

FIG. 39 depicts a representative image of control untreated tumor rat (left panel) and ABTM-468 treated rat (right panel). Control rat was euthanized due to distress, treated rat was euthanized to obtain age- and tumor-duration-matched tumors. The xenograft tumor model was developed from Panc1-cancer stem cells injected into the peritoneal space 3 weeks prior to the start of treatment. T, tumors; GB, gall bladder.

FIG. 40 depicts images demonstrating that DEspR+ inflammatory cells, NETosis-prone activated neutrophils, are detected in the tumor stroma in all stages of pancreatic cancer (PDAC), similar to metastatic tumors with an increasing trend towards Stage IV-PDAC. Bar=20 microns.

FIGS. 41A-41C depict graphs demonstrating that ABTM-468 anti-DEspR treatment improved kidney function in hypertensive Dahl S rats with mod-severed chronic kidney disease. FIG. 41A is a post-hoc demonstration of chronic kidney disease was done via quantitative analysis of the Raij Score for nephrosclerosis. FIG. 41B demonstrates that without anti-hypertensive therapy, anti-DEspR mAb treatment, ABTM-468, reduced albuminuria and (FIG. 41C) urinary albumin to creatinine ratio (UACR) after 7 days from 1× treatment.

Figure 42:
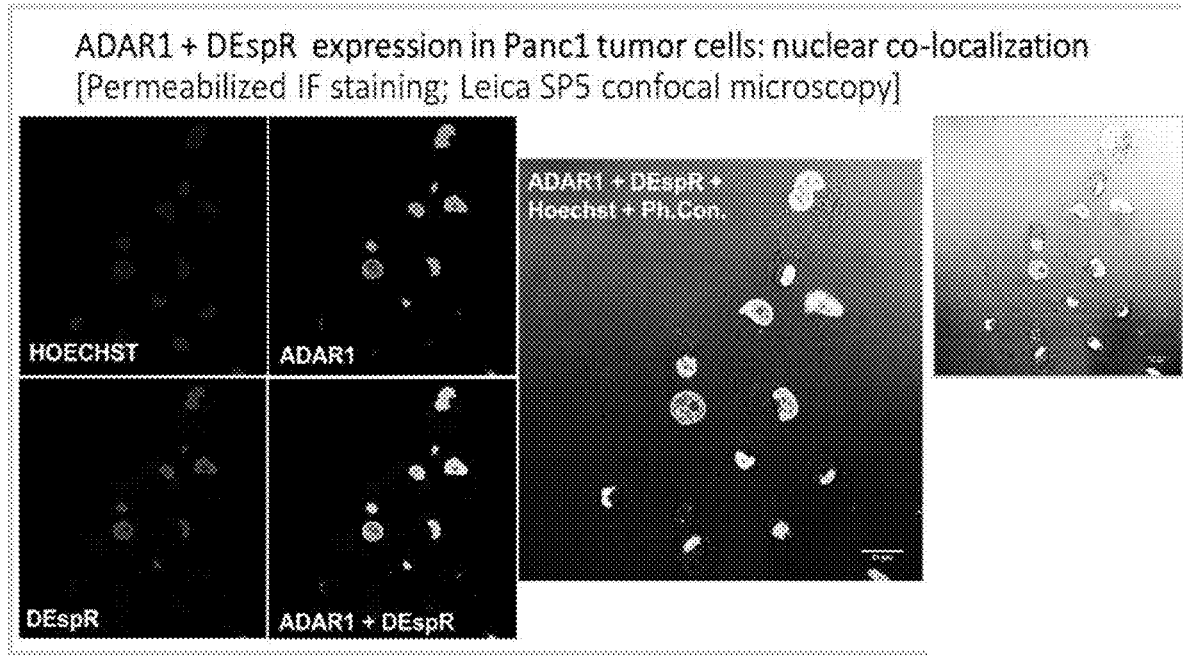

FIG. 42 depicts immunofluorescence staining and confocal microscopy digital photomicrographs. Hoechst: nuclear DNA stain; anti-Adar1 antibody; anti-DEspR hu-IgGS228P mAb (ABTM-468 or hu-6g8), phase contrast, and corresponding merged images.

DETAILED DESCRIPTION

As described herein, it has been found that anti-DEspR reagents functionally shuts down DEspR+ actPMNs that are dysregulated. This dysregulation can lead to tissue injury rather than resolution. Accordingly, the anti-DEspR reagents described herein can inhibit the excessive injurious functions of DEspR+"rogue" or hyper-activated PMNs (actPMNs) that drive neutrophil-mediated secondary tissue injury, e.g., by inhibiting the extended lifespan of such actPMNs. This inhibition reduces the excessive injurious level of actPMNs activity and/or the time during which rogue DEspR+ actPMNs activity of a given level is present in a subject. Accordingly, such anti-DEspR reagents can be used to treat a number of conditions characterized by and/or caused by DEspR+ actPMNs. Without wishing to be bound by theory, it is contemplated herein that the anti-DEspR reagent may act by binding DEspR present on the surface of actPMNs. Alternatively, the anti-DEspR reagents may act through another mechanism, e.g., by binding to a molecule that shares one or more epitopes with DEspR.

In one aspect of any of the embodiments, described herein is a method of decreasing the survival and/or activity of an activated neutrophil, the method comprising contacting the neutrophil with a DEspR inhibitor. In one aspect of any of the embodiments, described herein is a method of preventing or decreasing neutrophil extracellular trap (NET) release or actPMN NETosis in a subject in need thereof, the method comprising administering a therapeutically effective amount of a DEspR inhibitor to the subject.

As used herein "actPMN", "activated PMN", or "activated neutrophil" refers to a neutrophil (e.g. polymorphic nuclear cell) which has been activated, e.g., by chemotactic signals, cytokines, complement, and/or the presence of LPS. Activated neutrophils can exhibit, e.g., NET production/release, increased levels of cell-surface integrins (e.g., CD11b/CD18), ROS production and release, and degranulation. Levels of these markers and activities are readily measured by assays known in the art and described in the Examples herein. ActPMNs are further characterized by increased survival, e.g., beyond the normal lifespan (e.g., hours, or 1-2 days in some reports) of unactivated neutrophils. In some embodiments of any of the aspects, an actPMN can be a DEspR+ neutrophil. In some embodiments of any of the aspects, an actPMN can be a CD11b+ neutrophil.

As used herein, the term "NET" or "neutrophil extracellular trap" refers to an extracellular complex of nucleosomes and proteins, e.g. proteins having anti-microbial activity. Upon activation, neutrophils and other cells undergo a cell death program termed "NETosis" and release portions of nuclear DNA in the form of nucleosomes in complex with various proteins having antimicrobial activity (i.e. NETs). Release of NETs from neutrophils has been associated with inflammation and microthrombosis during sepsis and non-infectious diseases and demonstrated to contribute to the pathology of various diseases described herein. Vital NETosis refers to the release of NETs without concomitant cell death of the neutrophil.

As used herein, "DEspR" or "dual endothelin/VEGF signal peptide receptor" refers to a receptor expressed in tumor cells, microvessels, and anchorage-independent cancer stem cells (CSCs), with differential expression in cell- and nuclear-membranes, as well as in the cytoplasm. DEspR is differentially increased in both human pancreatic cancer and glioblastoma in contrast to adjacent normal tissue. However, despite these data, DEspR is still annotated as a non-coding RNA or ncRNA FBXW7 antisense RNA1 in the NCBI database. Sequences for DEspR polypeptides and nucleic acids are known in the art, e.g., human DEspR (NCBI Gene ID: 102191832). For example, a DEspR polypeptide can be: MTMFKGSNEMKSRWNWGSITCI-ICFTCVGSQLSMSS SKASNFSGPLQLYQRELEIFIVLT-DVPNYR LIKENSHLHTTIVDQGRTV (SEQ ID NO: 37), as described by, e.g., Accession Number EF212178.1, Gene ID 102191832, or Glorioso et al. 2007, together with naturally occurring allelic, splice variants, and processed forms thereof. Typically, as used herein, DEspR refers to human DEspR of SEQ ID NO: 37.

As used herein, the term "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody can be used to determine the level of a polypeptide. The activity of, e.g. DEspR can be determined using methods known in the art. In some embodiments, the inhibitor can be an inhibitory nucleic acid; an aptamer; an antibody reagent; an antibody; or a small molecule.

In some embodiments of any of the aspects, a DEspR inhibitor can be an anti-DEspR antibody reagent, antibody, or an antigen-binding fragment thereof. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof, including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems.

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only $V_L$ domains have also been shown to specifically bind to target epitopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 38), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody or antibody reagent as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cysteine residue, a marker peptide and a C-terminal polyhistidinyl, e.g., hexahistidinyl tag ('hexahistidinyl tag' disclosed as SEQ ID NO: 39) in order to produce bivalent and biotinylated scFv molecules.

In some embodiments, the antibody or antibody reagent described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments, it is possible to make one or more conservative amino acid substitutions of CDR residues without appreciably affecting the binding affinity of the resulting humanized immunoglobulin or human antibody variant. In some embodiments, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent as described herein. Such functional activities include binding to cancer cells and/or anti-cancer activity. Additionally, a polypeptide having functional activity means the polypeptide exhibits activity similar, but not necessarily identical to, an activity of a reference antibody or antibody reagent as described herein, including mature forms, as measured in a particular assay, such as, for example, a biological assay, with or without dose dependency. In the case where dose dependency does exist, it need not be identical to that of the reference antibody or antibody reagent, but rather substantially similar to the dose-dependence in a given activity as compared to the reference antibody or antibody reagent as described herein (i.e., the candidate polypeptide will exhibit greater activity, or not more than about 25-fold less, about 10-fold less, or about 3-fold less activity relative to the antibodies or antibody reagents described herein).

In some embodiments, the antibody reagents described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments, the antibody or antibody reagent is an isolated polypeptide. In some embodiments, the antibody or antibody reagent is a purified polypeptide. In some embodiments, the antibody or antibody reagent is an engineered polypeptide.

In one aspect of any of the embodiments, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3; or
a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding portion thereof specifically binds to DEspR and competes for binding with an antibody comprising:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding fragment thereof, comprises heavy chain CDRs having the amino acid sequences of SEQ ID NOs: 1-3. In some embodiments of any of the aspects, the antibody, antibody reagent, or antigen-binding fragment thereof, comprises heavy chain CDRs having the amino acid sequences of SEQ ID NOs: 1-3 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 9-11. In some embodiments of any of the aspects, the antibody, antibody reagent, or antigen-binding fragment thereof, comprises light chain CDRs having the amino acid sequences of SEQ ID NOs: 9-11 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3.

In some embodiments of any of the aspects, the antibody, antibody reagent, or antigen-binding fragment thereof comprises the heavy or light chain complementarity determining region (CDR)s as follows:
  (a) a light chain CDR1 having the amino acid sequence of SEQ ID NO: 9;
  (b) a light chain CDR2 having the amino acid sequence of SEQ ID NO: 10;
  (c) a light chain CDR3 having the amino acid sequence of SEQ ID NO: 11;
  (d) a heavy chain CDR1 having the amino acid sequence of SEQ ID NO: 1;
  (e) a heavy chain CDR2 having the amino acid sequence of SEQ ID NO: 2; and
  (f) a heavy chain CDR3 having the amino acid sequence of SEQ ID NO: 3; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 1-3 and 9-11. In some embodiments, the antibody, antibody reagent, antigen-binding portion thereof, or CAR can comprise CDRs having the sequence of the CDRs of SEQ ID NOs: 1-3 and 9-11.

In one aspect of any of the embodiments, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
  (a) a light chain CDR1 having the amino acid sequence of SEQ ID NO: 17;
  (b) a light chain CDR2 having the amino acid sequence of SEQ ID NO: 18;
  (c) a light chain CDR3 having the amino acid sequence of SEQ ID NO: 19;
  (d) a heavy chain CDR1 having the amino acid sequence of SEQ ID NO: 1;

(e) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).

In some embodiments of any of the aspects, the antibody, antibody reagent, or antigen-binding fragment thereof comprises at least one heavy or light chain complementarity determining region (CDR) selected from the group consisting of:
(a) a light chain CDR1 having the amino acid sequence of SEQ ID NO: 17;
(b) a light chain CDR2 having the amino acid sequence of SEQ ID NO: 18;
(c) a light chain CDR3 having the amino acid sequence of SEQ ID NO: 19;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3.

In some embodiments of any of the aspects, the antibody, antibody reagent, or antigen-binding portion thereof specifically binds to DEspR and competes for binding with an antibody comprising:
(a) a light chain CDR1 having the amino acid sequence of SEQ ID NO: 17;
(b) a light chain CDR2 having the amino acid sequence of SEQ ID NO: 18;
(c) a light chain CDR3 having the amino acid sequence of SEQ ID NO: 19;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3.

In some embodiments of any of the aspects, the antibody, antibody reagent, or antigen-binding fragment thereof, comprises heavy chain CDRs having the amino acid sequences of SEQ ID NOs: 1-3. In some embodiments of any of the aspects, the antibody, antibody reagent, or antigen-binding fragment thereof, comprises heavy chain CDRs having the amino acid sequences of SEQ ID NOs: 1-3 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 17-19. In some embodiments of any of the aspects, the antibody, antibody reagent, or antigen-binding fragment thereof, comprises light chain CDRs having the amino acid sequences of SEQ ID NOs: 17-19 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 17;
(b) a light chain CDR2 having the amino acid sequence of SEQ ID NO: 18;
(c) a light chain CDR3 having the amino acid sequence of SEQ ID NO: 19;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 17;
(b) a light chain CDR2 having the amino acid sequence of SEQ ID NO: 18;
(c) a light chain CDR3 having the amino acid sequence of SEQ ID NO: 19;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 1-3 and 17-19. In some embodiments, the antibody, antibody reagent, antigen-binding portion thereof, or CAR can comprise CDRs having the sequence of the CDRs of SEQ ID NOs: 1-3 and 17-19.

In one aspect of any of the embodiments, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
(a) a light chain CDR1 having the amino acid sequence of SEQ ID NO: 13;
(b) a light chain CDR2 having the amino acid sequence of SEQ ID NO: 14;
(c) a light chain CDR3 having the amino acid sequence of SEQ ID NO: 15;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7; or
a conservative substitution variant of one or more of (a)-(f).

In some embodiments of any of the aspects, the antibody, antibody reagent, or antigen-binding fragment thereof comprises at least one heavy or light chain complementarity determining region (CDR) selected from the group consisting of:
(a) a light chain CDR1 having the amino acid sequence of SEQ ID NO: 13;
(b) a light chain CDR2 having the amino acid sequence of SEQ ID NO: 14;
(c) a light chain CDR3 having the amino acid sequence of SEQ ID NO: 15;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7.

In some embodiments of any of the aspects, the antibody, antibody reagent, or antigen-binding portion thereof specifically binds to DEspR and competes for binding with an antibody comprising:
- (a) a light chain CDR1 having the amino acid sequence of SEQ ID NO: 13;
- (b) a light chain CDR2 having the amino acid sequence of SEQ ID NO: 14;
- (c) a light chain CDR3 having the amino acid sequence of SEQ ID NO: 15;
- (d) a heavy chain CDR1 having the amino acid sequence of SEQ ID NO: 5;
- (e) a heavy chain CDR2 having the amino acid sequence of SEQ ID NO: 6; and
- (f) a heavy chain CDR3 having the amino acid sequence of SEQ ID NO: 7.

In some embodiments of any of the aspects, the antibody, antibody reagent, or antigen-binding fragment thereof, comprises heavy chain CDRs having the amino acid sequences of SEQ ID NOs: 5-7. In some embodiments of any of the aspects, the antibody, antibody reagent, or antigen-binding fragment thereof, comprises heavy chain CDRs having the amino acid sequences of SEQ ID NOs: 5-7 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 13-15. In some embodiments of any of the aspects, the antibody, antibody reagent, or antigen-binding fragment thereof, comprises light chain CDRs having the amino acid sequences of SEQ ID NOs: 13-15 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
- (a) a light chain CDR1 having the amino acid sequence of SEQ ID NO: 13;
- (b) a light chain CDR2 having the amino acid sequence of SEQ ID NO: 14;
- (c) a light chain CDR3 having the amino acid sequence of SEQ ID NO: 15;
- (d) a heavy chain CDR1 having the amino acid sequence of SEQ ID NO: 5;
- (e) a heavy chain CDR2 having the amino acid sequence of SEQ ID NO: 6; and
- (f) a heavy chain CDR3 having the amino acid sequence of SEQ ID NO: 7.

In some embodiments of any of the aspects, the antibody, antibody reagent, or antigen-binding fragment thereof comprises the heavy or light chain complementarity determining region (CDR)s as follows:
- (a) a light chain CDR1 having the amino acid sequence of SEQ ID NO: 13;
- (b) a light chain CDR2 having the amino acid sequence of SEQ ID NO: 14;
- (c) a light chain CDR3 having the amino acid sequence of SEQ ID NO: 15;
- (d) a heavy chain CDR1 having the amino acid sequence of SEQ ID NO: 5;
- (e) a heavy chain CDR2 having the amino acid sequence of SEQ ID NO: 6; and
- (f) a heavy chain CDR3 having the amino acid sequence of SEQ ID NO: 7; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 5-7 and 13-15. In some embodiments, the antibody, antibody reagent, antigen-binding portion thereof, or CAR can comprise CDRs having the sequence of the CDRs of SEQ ID NOs: 5-7 and 13-15.

In one aspect of any of the embodiments, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
- (a) a light chain CDR1 having the amino acid sequence of SEQ ID NO: 25;
- (b) a light chain CDR2 having the amino acid sequence of SEQ ID NO: 26;
- (c) a light chain CDR3 having the amino acid sequence of SEQ ID NO: 27;
- (d) a heavy chain CDR1 having the amino acid sequence of SEQ ID NO: 21;
- (e) a heavy chain CDR2 having the amino acid sequence of SEQ ID NO: 22; and
- (f) a heavy chain CDR3 having the amino acid sequence of SEQ ID NO: 23; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
- (a) a light chain CDR1 having the amino acid sequence of SEQ ID NO: 25;
- (b) a light chain CDR2 having the amino acid sequence of SEQ ID NO: 26;
- (c) a light chain CDR3 having the amino acid sequence of SEQ ID NO: 27;
- (d) a heavy chain CDR1 having the amino acid sequence of SEQ ID NO: 21;
- (e) a heavy chain CDR2 having the amino acid sequence of SEQ ID NO: 22; and
- (f) a heavy chain CDR3 having the amino acid sequence of SEQ ID NO: 23.

In some embodiments of any of the aspects, the antibody, antibody reagent, or antigen-binding portion thereof specifically binds to DEspR and competes for binding with an antibody comprising:
- (a) a light chain CDR1 having the amino acid sequence of SEQ ID NO: 25;
- (b) a light chain CDR2 having the amino acid sequence of SEQ ID NO: 26;
- (c) a light chain CDR3 having the amino acid sequence of SEQ ID NO: 27;
- (d) a heavy chain CDR1 having the amino acid sequence of SEQ ID NO: 21;
- (e) a heavy chain CDR2 having the amino acid sequence of SEQ ID NO: 22; and
- (f) a heavy chain CDR3 having the amino acid sequence of SEQ ID NO: 23.

In some embodiments of any of the aspects, the antibody, antibody reagent, or antigen-binding fragment thereof, comprises heavy chain CDRs having the amino acid sequences of SEQ ID NOs: 21-23. In some embodiments of any of the aspects, the antibody, antibody reagent, or antigen-binding fragment thereof, comprises heavy chain CDRs having the amino acid sequences of SEQ ID NOs: 21-23 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 25-27. In some embodiments of any of the aspects, the antibody, antibody reagent, or antigen-binding fragment thereof, comprises light chain CDRs having the amino acid sequences of SEQ ID NOs: 25-27 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 21-23 and 25-27. In some embodiments, the antibody, antibody reagent, antigen-binding portion thereof, or CAR can comprise CDRs having the sequence of the CDRs of SEQ ID NOs: 21-23 and 25-27.

In one aspect of any of the embodiments, described herein is an antibody, antigen reagent, or antigen-binding fragment thereof that specifically binds a DEspR polypeptide. In some embodiments of any of the aspects, the antibody, antigen reagent, or antigen-binding fragment thereof comprises at least one heavy or light chain complementarity determining region (CDR) selected from the group consisting of:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31; or a conservative substitution variant of one or more of (a)-(f). In some embodiments of any of the aspects, the antibody, antibody reagent, or antigen-binding fragment thereof comprises at least one heavy or light chain complementarity determining region (CDR) selected from the group consisting of:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding portion thereof specifically binds to DEspR and competes for binding with an antibody comprising:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding fragment thereof, comprises heavy chain CDRs having the amino acid sequences of SEQ ID NOs: 29-31. In some embodiments of any of the aspects, the antibody, antibody reagent, or antigen-binding fragment thereof, comprises heavy chain CDRs having the amino acid sequences of SEQ ID NOs: 29-31 or a conservative substitution variant of such amino acid sequence. In some embodiments of any of the aspects, the antibody, antibody reagent, or antigen-binding fragment thereof, comprises light chain CDRs having the amino acid sequences of SEQ ID NOs: 33-35. In some embodiments of any of the aspects, the antibody, antibody reagent, or antigen-binding fragment thereof, comprises light chain CDRs having the amino acid sequences of SEQ ID NOs: 33-35 or a conservative substitution variant of such amino acid sequence.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 33;
(b) a light chain CDR2 having the amino acid sequence of SEQ ID NO: 34;
(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31.

In some embodiments of any of the aspects, the antibody, antibody reagent, or antigen-binding fragment thereof comprises the heavy or light chain complementarity determining region (CDR)s as follows:
(a) a light chain CDR1 having the amino acid sequence of SEQ ID NO: 33;
(b) a light chain CDR2 having the amino acid sequence of SEQ ID NO: 34;

(c) a light chain CDR3 having the amino acid sequence of SEQ ID NO: 35;
(d) a heavy chain CDR1 having the amino acid sequence of SEQ ID NO: 29;
(e) a heavy chain CDR2 having the amino acid sequence of SEQ ID NO: 30; and
(f) a heavy chain CDR3 having the amino acid sequence of SEQ ID NO: 31; or a conservative substitution variant of the amino acid sequence of any of (a)-(f).

In some embodiments, the antibody, antibody reagent, or antigen-binding portion thereof can comprise one or more CDRs (e.g., one CDR, two CDRs, three CDRs, four CDRs, five CDRs, or six CDRs) having the sequence of a CDR selected from SEQ ID NOs: 29-31 and 33-35. In some embodiments, the antibody, antibody reagent, antigen-binding portion thereof, or CAR can comprise CDRs having the sequence of the CDRs of SEQ ID NOs: 29-31 and 33-35.

In some embodiments, the antibody, antibody reagent, or antigen-binding portion thereof can comprise CDRs having at least 90% homology, at least 95% homology, at least 97% homology, at least 98% homology, or more with the CDRs of an antibody of Table 3. As will be understood by those skilled in the art, a variety of algorithms are available that permit comparison of sequences in order to determine their degree of homology, including by permitting gaps of designated length in one sequence relative to another when considering which residues "correspond" to one another in different sequences. One procedure for obtaining antibody mutants, such as CDR mutants, is "alanine scanning mutagenesis" (Cunningham & Wells, Science 244:1081-1085 (1989); and Cunningham & Wells, Proc Nat Acad Sci USA 84:6434-6437 (1991)). One or more of the hypervariable region residue(s) are replaced by alanine or polyalanine residue(s). Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues. A more systematic method for identifying amino acid residues to modify comprises identifying hypervariable region residues involved in binding DEspR and those hypervariable region residues with little or no involvement with DEspR binding. An alanine scan of the non-binding hypervariable region residues is performed, with each ala mutant tested for enhancing binding to DEspR. In another embodiment, those residue(s) significantly involved in binding DEspR are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained. Even more substantial modification in an antibody range and presentation of biological properties can be accomplished by selecting an amino acid that differs more substantially in properties from that normally resident at a site. Thus, such a substitution can be made while maintaining: (a) the structure of the polypeptide backbone in the area of the substitution, for example, as a sheet or helical conformation; (b) the charge or hydrophobicity of the molecule at the target site, or (c) the bulk of the side chain.

Exemplary antibodies and antibody reagents which bind DEspR are described in US Patent Publications 2017/0058036 and 2016/0108124, each of which are incorporated by reference herein in their entireties.

TABLE 3

Exemplary anti-DEspR antibody reagent sequences, per the Kabat system

| | Sequence | SEQ ID NO |
|---|---|---|
| 6G8G7 | | |
| HV1 | | |
| Heavy chain CDR1 | GYGVN | 1 |
| Heavy Chain CDR2 | MIWDDGSTDYNSALKS | 2 |
| Heavy Chain CDR3 | DPVVHFYAMDY | 3 |
| VH Domain | GSQVQLQESGPGLVAPSQSLSITCTVSGF SLTGYGVNWVRQPPGKGLEWLGMIWDDGS TDYNSALKSRLIITKDNSRSQVFLKMNSL QTDDTARYYCARDPVVHFYAMDYWGQGTS VTVSSAKTTPPSVYGGGGS | 4 |
| HV2 | | |
| Heavy chain CDR1 | RYWMS | 5 |
| Heavy Chain CDR2 | EINPDSSTINYTPSLKD | 6 |
| Heavy Chain CDR3 | HGRGMDY | 7 |
| VH Domain | GSEVQLQESGGGLVQPGGSLKLSCAASGF DFSRYWMSWVRQAPGKGLEWIGEINPDSS TINYTPSLKDKFIISRDTAKKTLYLQMSK VRSEDTALYYCARHGRGMDYWSQGTSVTV SSAKTTPPSVYGGGGS | 8 |
| KV1 | | |
| Light Chain CDR1 | KASQNVDSNVA | 9 |
| Light Chain CDR2 | SASYRYS | 10 |
| Light Chain CDR3 | QQYHSYP | 11 |
| VL Domain | GGGGSDIVLTQTNQIMSASVGDRVSVTCK ASQNVDSNVAWYQQKPGHSPKALIYSASY RYSRVPDRITGSGSGTDFTLTITNVQSKD LADYFCQQYHSYPLLAFGAGTKLELKRAD AAPTVSLE | 12 |
| KV2 | | |
| Light Chain CDR1 | KASQSVSNDVA | 13 |
| Light Chain CDR2 | YASNRYT | 14 |
| Light Chain CDR3 | QQDYSSPFT | 15 |
| VL Domain | GGGSDIVLTQTHKFLLVSAGDRITITCKA SQSVSNDVAWYQQKPGQSPKLLIYYASNR YTGVPDRFTGSGYGTDFTFTISTVQADDL AVYFCQQDYSSPFTFGGGTKLEIKRADAA PTVSLE | 16 |
| KV8 | | |
| Light Chain CDR1 | SASSSVSFMH | 17 |

TABLE 3-continued Exemplary anti-DEspR antibody reagent sequences, per the Kabat system

| | Sequence | SEQ ID NO |
|---|---|---|
| Light Chain CDR2 | STSNLAS | 18 |
| Light Chain CDR3 | QQRSSYP | 19 |
| VL Domain | GGGGSDIVITQSNAIMSASPGEKVTITCS ASSSVSFMHWFQQKPGTSPKLWIYSTSNL ASGVPARFSGSGSGTSYSLTISRMEAEDA ATYYCQQRSSYPLTFGAGTKLELKRADAA PTVSLE | 20 |
| 7C5B2 | | |
| HV2 | | |
| Heavy chain CDR1 | SYAVS | 21 |
| Heavy Chain CDR2 | VIWGDGSTDYHSALIS | 22 |
| Heavy Chain CDR3 | GTGTGFAY | 23 |
| VH Domain | QVQLKESGPGLVAPSQSLSITCTVSGFSL KSYAVSWVRQPPGKGLEWLGVIWGDGSTD YHSALISRLSISKDNSKSQFFLRLNSLQT DDTATYYCARGTGTGFAYWGQGTLVTVSA | 24 |
| KV2 | | |
| Light chain CDR1 | RSSQSLVHSNGNTYLH | 25 |
| Light Chain CDR2 | KVSNRFS | 26 |
| Light Chain CDR3 | SQCTHIPWT | 27 |
| VL Domain | DVVMTQTPLSLPVSLGDQASISCRSSQSL VHSNGNTYLHWYLQKPGQSPKWYKVSNRF SGVPDRFSGSGSGTDFTLKISRVEAEDLG IYFCSQCTHIPWTFGGGTNLEIK | 28 |
| 7C5B2 | | |
| Heavy chain CDR1 | G F S L T S Y D I S | 29 |
| Heavy Chain CDR2 | V I W T G G G T N Y N S A F M S | 30 |
| Heavy Chain CDR3 | DR DYDGWYFDV | 31 |
| VH Domain | Q V Q L K E S G P G L V A P S Q S L S I T C T V S G F S L T S Y D I S W I R Q P P G K G L E W L G V I W T G G G T N Y N S A F M S R L S I S K D N S K S Q V F L K M N S L Q TDDTAIY YCVRDRDYDGWYFDVWGAGTTVTVSS | 32 |
| Light chain CDR1 | RSSQSIVHSNGNTYLE | 33 |
| Light Chain CDR2 | KVSNRFS | 34 |
| Light Chain CDR3 | FQGSHVPYT | 35 |
| VL Domain | D V L M T Q T P L S L P V S L G D Q A S I S C R S S Q S I V H S N G N T Y L E W Y L Q K P G Q S P K L L I Y K V S N R F S G V P D R F S G S G S G T D F T L K I S R V E A E D L G V Y Y C F Q G S H V P Y T F G G G T K L E I K | 36 |

In some embodiments, the antibody or antibody reagent as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., DEspR. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., DEspR). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$, domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments, a conservatively modified variant of an antibody reagent can comprise alterations other than in the CDRs, e.g., a conservatively modified variant of an antibody, antibody reagent, or antigen-binding portion thereof, can comprise CDRs having the sequence of one or more of SEQ ID NOs: 1-3, 9-11, 17-19, 5-7, 13-15, 21-23, 25-27, 29-31, and 33-35. In some embodiments, a conservatively modified variant of an antibody, antibody reagent, or antigen-binding portion thereof, can comprise CDRs having the sequences of SEQ ID NOs: 1-3, 9-11, 17-19, 5-7, 13-15, 21-23, 25-27, 29-31, and 33-35.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody or antibody reagent as described herein comprises at least one CDR which is not identical to the sequence of SEQ ID Nos: 1-3, 9-11, 17-19, 5-7, 13-15, 21-23, 25-27, 29-31, and 33-35, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments of any of the aspects, the DEspR inhibitor described herein can be a bi-specific reagent, e.g., a bi-specific antibody or antibody reagent. Bispecific agents comprise a molecule which is able to physically contact and inhibit two different molecules simultaneously. In some embodiments of any of the aspects, the bispecific agent is a bispecific monoclonal antibody reagent, e.g., a bsAb. In some embodiments of any of the aspects, bispecific agents comprise a molecule which is able to physically contact and inhibit i) DEspR and ii) PD1 or PD-L1 simultaneously. As used herein, the term "bispecific" antibody or antibody reagent refers to an antibody or antibody reagent that comprises a first domain which has a binding site that has binding specificity for a first target, and a second domain which has a binding site that has binding specificity for a second target, i.e., the agent has specificity for two targets, e.g., i) DEspR and ii) PD1 or PD-L1. The first target and the second target are not the same (i.e., are different targets (e.g., proteins)). In some embodiments, the different targets can be co-expressed on the same cell. In some embodiments, a bispecific reagent can bind targets present on a single cell (heterophilic binding in cis), and/or bind one target on one cell and the other on another cell (heterophilic binding in trans). Accordingly, a bispecific reagent as described herein can selectively and specifically bind to a cell that expresses the first target and the second target. A non-limiting example of a bispecific reagent is a bispecific antibody construct. Bispecific antibody constructs comprising antigen-binding portions of antibodies specific for two different antigens can be readily constructed by one of skill in the art. Generally, sequences encoding the antigen-binding domain of a first antibody characterized and known to bind a desired epitope on one antigen can be joined, either directly, or through any of a variety of linkers as known to the ordinarily skilled artisan, to sequences encoding the antigen-binding domain of a second antibody characterized and known to bind a desired epitope on a second antigen. Such sequences can be inserted into an appropriate vector and introduced to a cell to produce the bispecific antibody polypeptide by methods known to those of ordinary skill in the art. PD-1 and/or PD-L1 inhibitors (e.g., anti-PD1 and/or anti-PD-L1 antibodies) are known in the art.

In some embodiments of any of the aspects, the bi-specific antibody reagent can bind specifically to and inhibit i) DEspR and ii) a target that modulates (e.g., inhibits) immune cell activity and/or survival. The purpose of binding to the target that modulates immune cell activity can include to simulate or inhibit immune cell activity, e.g., to enhance T-cell activity for tumor-surveillance, or to bind to an immune cell to approximate (bring together) two cells, e.g., the DEspR+ neutrophil and CD14+ macrophage. The target can be, e.g., a cell surface receptor, ligand or extracellular protein, or an intracellular protein. It has previously been demonstrated that anti-DEspR antibodies are internalized after binding to DEspR (see, e.g., Herrera et al. PLoS One 2014 9:e112335; which is incorporated by reference herein in its entirety), permitting the use of bispecific antibodies that bind to both DEspR and an intracellular target. Non-limiting examples of suitable cell surface receptors are PD1; CTLA-4 (e.g., NCBI Gene ID: 1493); TLR-2 (e.g., NCBI Gene ID: 7097); TLR-4 (e.g., NCBI Gene ID: 7099); CD14 (e.g., NCBI Gene ID: 929); or CD168 (e.g., NCBI Gene ID: 3161). Non-limiting examples of suitable ligands or extracellular protein are PD-L1; CD80 (e.g., NCBI Gene ID: 941): CD86 (e.g., NCBI Gene ID: 942); myeloperoxidase (MPO) (e.g., NCBI Gene ID 4353); cathepsin-G (e.g., NCBI Gene ID: 1511); neutrophil elastase (NE) (e.g., NCBI Gene ID: 1991), arginase-1 (e.g., NCBI Gene ID: 383), G-CSF (e.g., CSF3 or NCBI Gene ID: 1441), and GM-CSF (e.g., CSF2 or NCBI Gene ID: 1439). Non-limiting examples of suitable intracellular proteins include Mcl-1 (e.g., NCBI Gene ID: 4170); cIAP2 (e.g., NCBI Gene ID: 330); STAT3 (e.g., NCBI Gene ID: 6774); ERK1/2 (e.g. NCBI Gene ID: 5595 and 5594) petptidylarginine deaminase (PAD4) (e.g., NCBI Gene ID: 23569); galectin 1 (e.g., NCBI Gene ID: 3956), galectin 3 (e.g., NCBI Gene ID: 3958), or adenosine deaminase of RNA-1 (ADAR-1) (e.g., NCBI Gene ID: 103). Antibodies specific for such targets are known in the art, e.g., as shown in Table 6.

TABLE 6

| Target | Exemplary Antibody inhibitors |
|---|---|
| TLR-2 | ab9100, ab209217, ab191458, ab213676, ab16894, or ab1655 from Abcam; 11-9022-82 (mT2.7), 11-9021-82 (6C2), 11-922-42 (TL2.1) from Invitrogen |
| TLR-4 | 76B357.1 (ab22048), HTA125 (ab30667) MTS510 (ab95562) from Abcam: UT41 (53-9041-82) from Invitrogen |
| CD14 | 4B4F12 (ab182032); SP192 (ab183322); EPR3653 (ab133335), MEM-15 (ab28061) MEM-18 (ab6083); 1H5D8 (ab181470), 61D3 (ab25390) from Abcam; TuK4 (MHCD1401-4) from Invitrogen |
| CD168 | EPR4055 (ab108339), EPR4054 (ab124729); 2F2C9 (ab234065) from Abcam |
| CD80 | 16-10A1 (ab106162), EPR1157(2) (ab134120), 2A2 (ab86473), MEM-233 (ab69778) from Abcam; 2D10.4 (11-0809-42) from Invitrogen |
| CD86 | EP1158Y (ab53004), GL-1 (ab119857), BU63 (ab213044) from Abcam; B7-2 (11-0862-82) from Invitrogen |
| MPO | EPR20257 (ab208670), 2C7 (ab25989), 2D4 (ab90812), EPR4793 (ab134132), EPR4792 (ab 109116), EPR17996 (ab 188211) from Abcam; 8E6 (GM4192), MP0455-8E6 (11-1299-42) from Invitrogen |
| Cathepsin-G | 19C3 (LS-C87867) from LifeSpan Biosciences of Seattle WA; 9i239 (MBS249442) from MyBioSource of San Diego CA |
| NE | EPR7479 (ab 131260), SP203 (ab228286), RM0484-4W296 (ab205670) from Abcam; 39A (MAI-83125), 265-3K1 (MAI-40220), ELAI0-101.5 (MA1-10608), EL A10-103.2 (MAI-10609), EL A11-207.2 (MA1-10606) from Invitrogen |
| Arginase-1 | ARG1/1125 (ab212522) from Abcam; S16arg (14-9779-82), 24HL3 (702730), AlexF5 (25-3697-82) from Invitrogen |
| G-CSF | EPR3203 (ab 181053), 7E4F7 (ab204989), 8G5F7 (ab204998) from Abcam; 67604 (MA5-23758), 8F5CSF (50-7351-42), BVD13-3A5 (AHC2034) from Invitrogen |
| GM-CSF | 30-4 (ab54429), BVD2-21C11 (ab212313), KT35 (ab106790) from Abcam; MPI-22E9 (12-7331-82), MP122E9 (MA5-23799) from Invitrogen |
| Mcl-1 | Y37 (ab 186822), OTI2E11 (ab114026) from Abcam, LVUBKM (14-9047-82), Ab22 (14-6701-82), RCI3 (AHO0102) from Invitrogen |
| cIAP2 | E40 (ab32059) from Abcam; OTI3G4 (MA5-26360), J.391.2 (MAS-14997) from Invitrogen |
| STAT3 | 9D8 (ab119352), ERP787Y (ab68153), EP2147Y (ab76315), ERP361 (ab109085) El21-21 (ab32500) from Abcam; ST3-5G7 (13-7000), 3B5 (MA5-15712) from Invitrogen |
| ERK1 | 12D11 (Ab119357), EP4967 (ab 109282), Y72 (ab32537) from Abcam; ERK-6B11 (12-8600), 1E5 (MA5-15896) from Invitrogen |
| ERK2 | E460 (ab32081) from Abcam; 6F8 (MA1-099) from Invitrogen |
| PAD4 | OTI4H5 (ab 128086), EPR20706 (ab214810) from Abcam; OTI5C10 (MA5-26009), ATI6A2 (MA5-26006) from Invitrogen |
| Galectin 1 | EPR3206 (ab 138513), EPR3205 (ab225540), 6C8.4-1 (ab205889) from Abcam. |
| Galectin 3 | A3A12 (ab2785), EP2775Y (ab76245), EPR19244 (ab209344), EPR2774 (ab76466) from Abcam; AG001 (39-5100), M3/38 (12-5301-82) from Invitrogen |
| ADAR-1 | EPR7033 (ab126745), EPR7033 (ab206086) from Abcam; GT1066 (MA5-17285) from Invitrogen |

PD1 (or CD279) is a 288 amino acid type I transmembrane protein composed of one immunoglobulin (Ig) superfamily domain, a 20 amino acid stalk, a transmembrane domain, and an intracellular domain of approximately 95 residues containing an immunoreceptor tyrosine-based inhibitory motif (ITIM), as well as an immunoreceptor tyrosine-based switch motif (ITSM). PD1 is encoded by the Pdcd1 and PDCD1 genes on chromosome 1 in mice and chromosome 2 in humans respectively. In both species, Pdcd1 is encoded by 5 exons. Exon 1 encodes a short signal sequence, whereas exon 2 encodes an Ig domain. The stalk and transmembrane domains make up exon 3, and exon 4 codes for a short 12 amino acid sequence that marks the beginning of the cytoplasmic domain. Exon 5 contains the C-terminal intracellular residues and a long 3'UTR (Keir M E et al., 2008. Annu Rev Immunol. 26:677-704). PD1 is a member of the B7 family of receptors. The sequences for PD-1 are known for a number of species, e.g., human PD-1 (NCBI Gene ID: 5133). The term "PD-1" refers to any naturally occurring allele, splice variant, and/or processed forms thereof.

PD1 has two known ligands, PD-L1 and PD-L2, which are also members of the B7 family. The binding interface of PD1 to PD-L1 is via its IgV-like domain (i.e., PD1 (42-136)). Residues important for binding of PD1 to its ligands include residues 64, 66, 68, 73, 74, 75, 76, 78, 90, 122, 124, 126, 128, 130, 131, 132, 134, and 136. PD-L1/CD274 has been shown to be constitutively expressed on mouse T and B cells, DCs, macrophages, mesenchymal stem cells, and bone marrow-derived mast cells. CD274/PD-L1 expression is also found on a wide range of nonhematopoietic cells and is upregulated on a number of cell types after activation. PD-L1 is expressed on almost all murine tumor cell lines, including PA 1 myeloma, P815 mastocytoma, and B16 melanoma upon treatment with IFN-γ. Residues of PD-L1 important for binding to PD1 include PD-L1 (67), PD-L1 (121), PD-L1 (122), PD-L1 (123), PD-L1 (123), PD-L1 (124), and PD-L1 (126). The sequences for PD-L1 are known for a number of species, e.g., human PD-1 (NCBI Gene ID: 29126). The term "PD-L1" refers to any naturally occurring allele, splice variant, and/or processed forms thereof.

PD-1 inhibition can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments the PD-1 inhibitors include anti-PD-L1 inhibitors, e.g., antibodies. In certain other embodiments the PD-1 inhibitors include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade. Also specifically contemplated herein are agents that disrupt or block the interaction between PD-1 and PD-L1, such as a high affinity PD-L1 antagonist. Non-limiting examples of PD-1 inhibitors can include: pembrolizumab (Merck); nivolumab (Bristol Meyers Squibb); pidilizumab (Medivation); and AUNP12 (Aurigene).

Non-limiting examples of PD-L1 inhibitors can include atezolizumab (Genentech); MPDL3280A (Roche); MEDI4736 (AstraZeneca); MSB0010718C (EMD Serono); avelumab (Merck); and durvalumab (Medimmune).

Non-limiting examples of CTLA-4 inhibitors can include abatacept, ipilimumab and tremelimumab.

Bi-specific antibody reagents against DEspR and any of the targets described herein are readily prepared using the CDRs of any of the target-specific antibodies described herein or known in the art.

The antibody reagents described herein can be further modified to improve, e.g., immunogenicity or half-life. For example, an antibody reagent as described herein can be an IgG4 antibody reagent and/or a hinge-stabilized IgG4 antibody reagent. In some embodiments of any of the aspects, hinge-stabilization can comprise a S228P mutation relative to the wildtype IgG4 sequence, e.g., as described in the Examples herein.

Antibody reagents described herein can be administered to a subject by administering a cell comprising and/or expressing the antibody reagent. For example, the cell can be a T cell, CAR-T cell, or adoptively transferred T cell. In some embodiments of any of the aspects, the antibody reagent is a chimeric antigen receptor (CAR). In some embodiments of any of the aspects, the antibody reagent described herein is not a CAR, and the cell comprises the presently described antibody reagent in addition to a CAR. CAR-T cell and related therapies relate to adoptive cell transfer of immune cells (e.g., T cells) expressing a CAR that binds specifically to a targeted cell type (e.g., cancer cells) to treat a subject. In some embodiments of any of the aspects, the cells administered as part of the therapy can be autologous to the subject. In some embodiments of any of the aspects, the cells administered as part of the therapy are not autologous to the subject. In some embodiments of any of the aspects, the cells are engineered and/or genetically modified to express the CAR and/or the antibody reagent described herein. CAR, CAR-T, and other adoptive cell transfer technologies are well known in the art. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, the DEspR inhibitor, or anti-DEspR antibody reagent, or bi-specific antibody reagent described herein is an antibody-drug conjugate. The antibody-drug conjugate can comprise at least one anti-DEspR antibody reagent and at least one drug conjugated to the antibody reagent.

In particular embodiments, an antibody-drug conjugate comprises an antibody, antibody reagent, or antigen-binding portion thereof as described herein. The drug can be, e.g., a chemotherapeutic molecule as described elsewhere herein. In some embodiments of any of the aspects, the antibody-drug conjugate comprises a chemotherapeutic agent directly conjugated and/or bound to an antibody or antigen-binding portion thereof. In some embodiments of any of the aspects, binding can be non-covalent, e.g., by hydrogen bonding, electrostatic, or van der Waals interactions; however, binding may also be covalent. By "conjugated" is meant the covalent linkage of at least two molecules. In some embodiments of any of the aspects, the composition can be an antibody-drug conjugate.

In some embodiments of any of the aspects, an antibody, antibody reagent, or antigen-binding portion thereof can be bound to and/or conjugated to multiple chemotherapeutic molecules. In some embodiments of any of the aspects, an antibody-drug conjugate can be bound to and/or conjugated to multiple chemotherapeutic molecules. In some embodiments of any of the aspects, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments of any of the aspects, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

Exemplary drugs for use in antibody-drug conjugates can comprise a thrombolytic, a chemotherapeutic, a nanoparticle, a polypeptide, an imaging agent, a fluorophore, a small molecule, an enzyme, a nucleic acid molecule, or a chemical. Non-limiting examples of chemotherapeutics include mertansine, emtansine, gemcitabine, temozolomide, paclitaxel, or cis/oxali-platin. Non-limiting examples of nanoparticles include iron oxide-nanoparticle (IONP), polymeric nanoparticle, or gold nanoparticle, or chimeric nanoparticle. Non-limiting examples of an enzyme include DNaseI, e.g., human DNaseI, DNAseI, matrix metalloproteinase 1 (MMP1) matrix metalloproteinase 2 (MMP2), matrix metalloproteinase 3 (MMP3), a tissue inhibitor of metalloproteinases (TIMP), a protease, a recombinase, or a plasminogen activator. Non-limiting examples of polypeptides include chymostatin, angiopoietin 1/2, and SDF-1. Non-limiting examples of chemicals include 4-aminobenzoichydrazide or NX-059 nitrone. In some embodiments of the methods described herein, the subject can be a subject who is further administered a PD1 and/or PD-L1 inhibitor therapy, e.g., sequentially or concurrently, e.g., in the same composition or in separate compositions. Non-limiting examples of nucleic acid molecules can include RNA-inhibitors (siRNA, miRNA) or RNA modulator (miRNA) or transcription factor decoys (DNA-decoy).

PD-1 and/or PD-L1 inhibitor therapies can comprise antibodies, antibody reagents, CAR-Ts, or other molecules which bind to PD-1 and/or PD-L1 and thereby inhibit their activity and/or increase the apoptosis or phagocytosis of PD-1 and/or PD-L1-expressing cells.

In some embodiments of the methods described herein, the subject can be a subject who was previously administered a PD1 and/or PD-L1 inhibitor therapy. In some embodiments of the methods described herein, the subject can be resistant to treatment with PD1 and/or PD-L1 inhibitor therapy. The resistance can be innate, e.g., the tumor was never responsive to PD1 and/or PD-L1 inhibitor therapy or the resistance can develop over the course of treatment with PD1 and/or PD-L1 inhibitor therapy. In some embodiments of the methods described herein, the subject can be a subject with a toxicity from treatment with PD1 and/or PD-L1 inhibitor therapy, e.g., administration of PD1 and/or PD-L1 inhibitor therapy caused undesirable side effects, e.g. side effects which necessitated the cessation of the PD1 and/or PD-L1 inhibitor therapy.

In some embodiments of the methods described herein, the subject can be a subject who was previously administered a further immunotherapy. In some embodiments of the methods described herein, the subject can be resistant to treatment with a further immunotherapy. The resistance can be innate, e.g., the tumor was never responsive to the further immunotherapy or the resistance can develop over the course of treatment with the immunotherapy. In some embodiments of the methods described herein, the subject can be a subject with a toxicity from treatment with a further immunotherapy, e.g., administration of immunotherapy caused undesirable side effects, e.g. side effects which necessitated the cessation of the immunotherapy. In some embodiments of any of the aspects, the further immunotherapy can be PD1 and/or PD-L1 inhibitor therapy.

As used herein, "immunotherapy" refers to a diverse set of therapeutic strategies designed to induce the patient's own immune system to fight a disease, e.g., cancer or a tumor. Non-limiting examples of immunotherapies can include intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach, i.e., adoptive immunotherapy. In some embodiments, the methods described herein can further comprise administering an additional antibody, antibody reagent, antigen-binding portion thereof, or T cell comprising a CAR to the subject. In some embodiments, the methods described herein can further comprise administering one or more cytokines to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

In one aspect of any of the embodiments, described herein is a DEspR inhibitor, anti-DEspR antibody reagent, antibody-drug conjugate, and/or fi bispecific reagent as described in any of the aspects or embodiments herein.

In one aspect of any of the embodiments, described herein is a method of treating a condition or disease wherein neutrophils contribute to pathogenesis or worsening of the disease in a subject in need thereof, the method comprising administering a therapeutically effective amount of a DEspR inhibitor to the subject.

In one aspect of any of the embodiments, described herein is a method of treating a condition or disease wherein neutrophils, NETs, or NETosing or NETting neutrophils contribute to pathogenesis, chronicity, or worsening of the disease in a subject in need thereof, the method comprising administering a therapeutically effective amount of a DEspR inhibitor to the subject.

In one aspect of any of the embodiments, described herein is a method of preventing or decreasing NET release or actPMN NETosis in a subject in need thereof, the method comprising administering a therapeutically effective amount of an anti-DEspR antibody reagent conjugated to another anti-neutrophil or anti-NET reagent, e.g., to a second anti-neutrophil or anti-NET reagent.

A condition or disease wherein neutrophils contribute to pathogenesis or worsening of the disease is any disease in which the activity and/or level of neutrophils, e.g., activated neutrophils, contributes to the pathology of the condition, e.g., contribute to the development or cause of the disease, as opposed to being a symptom of or reaction to the disease itself. Such conditions are known in the art and can include, by way of non-limiting example, systemic inflammatory response syndrome (SIRS); acute lung injury (ALI); acute respiratory distress syndrome (ARDS); multi-organ failure or multi-organ dysfunction syndrome (MOS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endothelial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis.

In some embodiments of any of the aspects, a subject treated according to the methods described herein can be a subject having or diagnosed as having systemic inflammatory response syndrome (SIRS); acute lung injury (ALI); acute respiratory distress syndrome (ARDS); multi-organ failure or multi-organ dysfunction syndrome (MOS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endothelial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis.

Neutrophils have been implicated in the exacerbation bouts in multiple sclersosis. Accordingly, the methods described herein can relate to treatment of multiple sclersosis. Neutrophils have been implicated in acute kidney injury, which has no treatment to date. Accordingly, the methods described herein can relate to treatment of acute kidney injury. Immune evasion is implicated in the progression of precancerous lesions to malignant lesions, or micrometastatic lesions to macro-metastases. Neutrophils contribute to immune evasion by releasing substances that inhibit T-cells in their roles in immune-surveillance, thus increased DEspR-mediated survival in DEspR+ neutrophils contribute to the precancer-to-malignancy switch. Accordingly, the methods described herein can relate to treatment of precancerous lesions. Notably, several cancers are associated with prior infections and/or neutrophilia: pancreatitis is a risk factor for pancreatic cancer, and neutrophilia is induced by smoking which is linked to lung cancer.

In some embodiments of any of the aspects, a subject treated according to the methods described herein can have or be diagnosed as having cancer, and has a PD-L1+/DEspR+ tumor and/or cancer cells. A cell or tumor which is "positive" for a particular marker or polypeptide is a cell or tumor expressing an increased level of the marker or polypeptide, e.g., as compared to a healthy cell of the same type or an average level of the marker or polypeptide found in healthy cells of the same type. In some embodiments, an increased level of the marker or polypeptide can be a level which is at least 1.5× the level found in a reference, e.g., 1.5×, 2×, 3×, 4×, 5× or greater than the reference level.

In some embodiments of any of the aspects, a subject treated according to the methods described herein can have or be diagnosed as having cancer, and has previously been treated by tumor resection. In some embodiments of any of the aspects, the cancer is pancreatic ductal adenocarcinoma, glioblastoma, lung cancer, breast cancer, triple negative breast cancer, melanoma, or colorectal cancer.

In some embodiments, the subject treated according to the methods described herein can be a subject who has, or is determined to have a PD-L1+/DespR+ tumor; increased levels of circulating DEspR+ neutrophils; increased levels of DEspR+ activated neutrophils; increased levels of NETs; increased plasma levels of neutrophil elastase (NE); increased plasma levels of neutrophil myeloperoxidase (MPO); or a tumor comprising one or more of: DEspR+ neutrophils; DEspR+ NETosing neutrophils; NETs; an increased level of a neutrophil released immune-suppressor; an increased level of citrullinated-histone-3; and increased level of a neutrophil stimulator. Non-limiting neutrophil-released immune suppressors include arginase-1; PD-L1; myeloperoxidase (MPO); neutrophil-elastase (NE); or cathepsin G. Non-limiting neutrophil stimulators include G-CSF, ET1, Hif1a, or a DAMP. In some embodiments of any of the aspects, a level can be increased relative to a reference level, e.g., to the subject at an earlier time point, to a subject without cancer, or a subject with a cancer not involving NETs, NETosis, or activated neutrophils.

As used herein, "anti-NET" compound or reagent refers to any compound or reagent that degrades or targets for degradation any component of a NET for clearance and/or prevents the formation of NETs. Also included are compounds that otherwise inhibit the activity of a NET component. An anti-NET compound can be a nucleic acid (DNA or RNA), small molecule, lipid, carbohydrate, protein, peptide, antibody, or antibody fragment. In some embodiments, an anti-NET compound can be an enzyme, e.g. an enzyme which cleaves and/or degrades, e.g. a nucleic acid, protein, polypeptide, or carbohydrate. Examples of anti-NET compounds are described in US Patent Publication US 2014-0199329; which is incorporated by reference herein in its entirety. Non-limiting examples of anti-NET reagents can include DNase; RNAse; a histone-degrading enzyme; an inhibitor of chromatin decondensation; an antibody against a component of a NET; an elastase inhibitor; a PAD inhibitor; and a PAD4 inhibitor.

As used herein, "anti-neutrophil" compound or reagent refers to any compound or reagent that is toxic to a neutrophil, promotes apoptosis, and/or inhibits one or more activities of an actPMN, such as inhibition of neutrophil adhesion or transmigration (e.g., anti-ICAM 1), inhibition of neutrophil activation (e.g., anti-CD11b), or depletion of neutrophil precursors in the bone marrow (e.g., chemotherapies).

The compositions and methods described herein can be administered to a subject having or diagnosed as having a disease or condition as described herein. In some embodiments, the methods described herein comprise administering an effective amount of compositions described herein, e.g. an agent, e.g., a DEspR inhibitor, to a subject in order to alleviate a symptom of a disease or condition. As used herein, "alleviating a symptom" is ameliorating any condition or symptom associated with the disease or condition. As compared with an equivalent untreated control, such reduction is by at least 5%, 10%, 20%, 40%, 50%, 60%, 80%, 90%, 95%, 99% or more as measured by any standard technique. In one embodiment, the method described herein comprises administering an effective amount of a human or humanized antibody referred to herein as an anti-DEspR antibody. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an agent, e.g., a DEspR inhibitor needed to alleviate at least one or more symptom of the disease or disorder, and relates to a sufficient amount of pharmacological composition to provide the desired effect. The term "therapeutically effective amount" therefore refers to an amount of an agent, e.g., a DEspR inhibitor that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for actPMNs and/or NETs, among others. The dosage can be determined by a physician and adjusted, as necessary, to suit observed effects of the treatment.

In some embodiments, the technology described herein relates to a pharmaceutical composition comprising an agent, e.g., a DEspR inhibitor, as described herein, and optionally a pharmaceutically acceptable carrier. In some embodiments, the active ingredients of the pharmaceutical composition comprise an agent, e.g., a DEspR inhibitor, as described herein. In some embodiments, the active ingredients of the pharmaceutical composition consist essentially of an agent, e.g., a DEspR inhibitor, as described herein. In some embodiments, the active ingredients of the pharmaceutical composition consist of an agent, e.g., a DEspR inhibitor, as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an agent, e.g., a DEspR inhibitor, as described herein.

In some embodiments, the pharmaceutical composition comprising an agent, e.g., a DEspR inhibitor, as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agent, e.g., a DEspR inhibitor, as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt as disclosed herein can also be incorporated into the parenteral dosage forms of the disclosure, including conventional and controlled-release parenteral dosage forms.

Pharmaceutical compositions comprising an agent, e.g., a DEspR inhibitor, as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the agent, e.g., a DEspR inhibitor, described herein is administered as a monotherapy, e.g., another treatment for the disease or condition is not administered to the subject.

In some embodiments of any of the aspects, the methods described herein can further comprise administering a second agent and/or treatment to the subject, e.g. as part of a combinatorial therapy. Non-limiting examples of a second agent (including exemplary chemotherapies) and/or treatment can include radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In some embodiments of any of the aspects, the subject is further administered a further immunotherapy and/or chemotherapy. In some embodiments of any of the aspects, the subject has previously been administered a further immunotherapy and/or chemotherapy. In some embodiments of any of the aspects, the subject is resistant to treatment with a further immunotherapy and/or chemotherapy. In some embodiments of any of the aspects, the chemotherapy (e.g., administered with the DEspR inhibitor or as part of an antibody-drug conjugate) can be gemcitabine, paclitaxel, temozolomide, irinotecan, abraxane, a platinum-based chemotherapy, a cisplatin, an oxiloplatin, or combinations thereof, such as FOLFIRINOX.

As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments of any of the aspects, the immunotherapy stimulates NK responses. In some embodiments of any of the aspects, the immunotherapy is an adoptive cell transfer approach, i.e., adoptive immunotherapy. Exemplary immunotherapies can include an immune checkpoint protein immunotherapy (e.g., a PD1 and/or PD-L1 inhibitor therapy, a T-cell co-stimulator; or CAR-T therapy.

In certain embodiments, an effective dose of a composition comprising an agent, e.g., a DEspR inhibitor, as described herein can be administered to a patient once. In certain embodiments, an effective dose of a composition comprising an agent, e.g., a DEspR inhibitor, as described herein can be administered to a patient repeatedly. For systemic administration, subjects can be administered a therapeutic amount of a composition comprising an agent, e.g., a DEspR inhibitor, as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agent, e.g., a DEspR inhibitor, as described herein can be administered over a period of time, such as over a 5 minute, 10 minute, 15 minute, 20 minute, or 25 minute period.

The dosage ranges for the administration of an agent, e.g., a DEspR inhibitor, as described herein, according to the methods described herein depend upon, for example, the form of the agent, e.g., a DEspR inhibitor, as described herein, its potency, and the extent to which symptoms, markers, or indicators of a condition described herein are desired to be reduced, for example the percentage reduction desired for actPMNs and/or NETs. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agent, e.g., a DEspR inhibitor, as described herein in, e.g. the treatment of a condition described herein, or to induce a response as described herein (e.g. increased PMN cell death) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. level of actPMNs and/or NETs. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer or NETosis. When using an experimental animal model, efficacy of treatment is evidenced when a statistically significant change in a marker is observed, e.g. actPMN and/or NET levels.

In vitro and animal model assays are provided herein which allow the assessment of a given dose of an agent, e.g., a DEspR inhibitor, as described herein. By way of non-limiting example, the effects of a dose of an agent, e.g., a DEspR inhibitor, as described herein can be assessed by measuring actPMN levels, actPMN survival, actPMN activity (e.g., myeloperoxidase levels, neutrophil elastase levels), neutrophil-lymphocyte ratio, and/or levels of NETs.

In some embodiments of any of the aspects, the subject administered a treatment as described herein can be a subject determined to have DEspR+ neutrophils and/or an increased or elevated level of DEspR+ neutrophils.

In one aspect of any of the embodiments, described herein is a method of identifying a subject at risk of neutrophil extracellular trap (NET) release, vital NETosis or actPMN NETosis, the method comprising detecting the level of DEspR+ neutrophils in a sample obtained from the subject, wherein an increased level of DEspR+ neutrophils relative to a reference indicates the subject is at increased risk of neutrophil extracellular trap (NET) release, vital NETosis or actPMN NETosis. In one aspect of any of the embodiments, described herein is a method of identifying a subject at risk of neutrophil extracellular trap (NET) release, vital NETosis or actPMN NETosis, the method comprising detecting the level of DEspR in neutrophils obtained from the subject, wherein an increased level of DEspR+ in the neutrophils relative to a reference indicates the subject is at increased risk of neutrophil extracellular trap (NET) release, vital NETosis or actPMN NETosis.

In some embodiments of any of the aspects, the expression level of e.g., DEspR, can be measured by determining the level of an expression product of the DEspR, gene, e.g., a DEspR RNA transcript or a DEspR polypeptide. Such molecules can be isolated, derived, or amplified from a biological sample, such as a biofluid. In some embodiments of any of the aspects, a detectable signal is generated by the antibody or antigen-binding portion thereof when a DEspR molecule is present. In some embodiments of any of the aspects, the antibody or antigen-binding portion thereof is detectably labeled or capable of generating a detectable signal. In some embodiments of any of the aspects, the level of the, e.g., DEspR molecule, is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy; FACS; and immunoelectrophoresis assay. In some embodiments of any of the aspects, the antibody or antigen-binding portion thereof is detectably labeled or generates a detectable signal. In some embodiments of any of the aspects, the expression level of, e.g., DEspR, is normalized relative to the expression level of one or more reference genes or reference proteins. In some embodiments of any of the aspects, the reference level DEspR is the expression level of DEspR in a prior sample obtained from the subject.

In some embodiments of any of the aspects, the level of, e.g., DEspR, can be the level of DEspR polypeptide. Detection of polypeptides can be according to any method known in the art. Immunological methods to detect particular polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, an e.g., DEspR polypeptide. In some embodiments of any of the aspects, the assays, methods, and/or systems described herein can comprise: an anti-DEspR antibody reagent. In some embodiments of any of the aspects, the antibody reagent can be detectably labeled. In some embodiments of any of the aspects, the antibody reagent can be attached to a solid support (e.g., bound to a solid support). In some embodiments of any of the aspects, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., DEspR). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a target molecule. Between each step the plate is typically washed with a mild detergent solution to remove any proteins or antibodies that are not specifically bound. After the final wash step the plate is developed by adding an enzymatic substrate to produce a visible signal, which indicates the quantity of the target polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of, e.g., DEspR polypeptide in a sample. LFIAs are a simple device intended to detect the presence (or absence) of a target in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of the target present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a DEspR-specific antibody reagent). The test line will also contain antibody reagents (e.g., a DEspR-specific antibody reagent). The test line will show as a colored band in positive samples. In some embodiments of any of the aspects, the lateral flow immunoassay can be a double antibody sandwich assay, a competitive assay, a quantitative assay or variations thereof.

There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of, e.g., DEspR polypeptides. In some embodiments of any of the aspects, the dip stick (or LFIA) can be suitable for use with urine samples. In some embodiments of any of the aspects, a dip stick can be suitable for use with blood samples.

Immunochemistry is a family of techniques based on the use of a specific antibody, wherein antibodies are used to specifically target molecules inside or on the surface of cells. In some embodiments of any of the aspects, immunohistochemistry ("IHC") and immunocytochemistry ("ICC") techniques can be used to detect or measure the levels of, e.g., DEspR polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments of any of the aspects, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments of any of the aspects, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments of any of the aspects, a detectable label can be a radiolabel including, but not limited to $^3$H, $^{125}$I, $^{35}$S, $^{14}$C, $^{32}$p, and $^{33}$P.

In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments of any of the aspects, a detectable label is a chemiluminescent label, including, but not limited to lucigenin, luminol, luciferin, isoluminol, theromatic acridinium ester, imidazole, acridinium salt and oxalate ester.

In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The methods as described herein can relate to determining if a subject has an increased level of, e.g., DEspR relative to a reference level. In some embodiments of any of the aspects, the reference level of the marker (e.g., DEspR) can be the level of the marker in a healthy subject not having, or not diagnosed as having, e.g., cancer. In some embodiments of any of the aspects, the reference level can be the level in a sample of similar cell type, sample type, sample processing, and/or obtained from a subject of similar age, sex and other demographic parameters as the sample/subject for which the level of the target is to be determined. In some embodiments of any of the aspects, the test sample and control reference sample are of the same type, that is, obtained from the same biological source, and comprising the same composition, e.g., the same number and type of cells and/or type of sample material. Accordingly, in some embodiments of any of the aspects, the level of the target which is increased can vary as demographic factors such as age, gender, genotype, environmental factors, and individual medical histories vary. In some embodiments of any of the aspects, the reference level can comprise the level of the target, (e.g., DEspR or DEspR+ neutrophils) in a sample of the same type taken from a subject not exhibiting any signs or symptoms of, e.g., cancer. In some embodiments of any of the aspects, the reference expression level of the marker can be the expression level of the marker in a prior sample obtained from the subject. This permits a direct analysis of any change in levels in that individual.

In some embodiments of any of the aspects, a level of a marker can be increased relative to a reference level if the level of the marker is at least 1.25× the reference level, e.g., at least 1.25×, at least 1.5×, at least 2×, at least 3×, at least 4×, at least 5×, at least 6×, or greater of the reference level. In some embodiments of any of the aspects, the expression level of the marker can be normalized relative to the expression level of one or more reference genes or reference proteins. In some embodiments of any of the aspects, the expression level of the marker can be normalized relative to a reference value.

In some embodiments of any of the aspects, the expression level of no more than 20 other genes is determined. In some embodiments of any of the aspects, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments of any of the aspects, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, prepared by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of a marker as described herein.

In some embodiments of any of the aspects, the methods, assays, and systems described herein can further comprise a step of obtaining a test sample from a subject. In some embodiments of any of the aspects, the subject can be a human subject.

In some embodiments of any of the aspects, the methods, assays, and systems described herein can comprise creating a report based on the level of the marker. In some embodiments of any of the aspects, the report denotes raw values for the marker, in the test sample (plus, optionally, the level of the marker in a reference sample) or it indicates a percentage or fold increase in the marker as compared to a reference level, and/or provides a signal that the subject is at risk of having, or not having cancer.

As used herein "at risk of having" refers to at least a 2-fold greater likelihood of having a particular condition as compared to a subject that did not have an elevated and/or increased level of the marker, e.g., a 2-fold, or 2.5-fold, or 3-fold, or 4-fold, or greater risk.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition described herein, e.g., cancer. A subject can be male or female.

In some embodiments of any of the aspects, the subject or patient can be a human. In some embodiments of any of the aspects, the subject or patient can be a mammal. Thus, in one embodiment, mammals can include cats, dogs, pigs, horses, cows, sheep, and goats, as well as humans. The methods described herein are applicable to veterinary methods and treatments. For example, where laminitis in horses is caused by actPMNs, in some embodiments the subject is a non-human mammal.

A subject can be one who has been previously diagnosed with or identified as suffering from or having a condition in need of treatment or one or more complications related to such a condition, and optionally, have already undergone treatment for a disease or condition or the one or more complications related to the disease or condition. Alternatively, a subject can also be one who has not been previously diagnosed as having the disease or condition or one or more complications related to the disease or condition. For example, a subject can be one who exhibits one or more risk factors for the disease or condition or one or more complications related to the disease or condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g. an antibody or antibody reagent) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression"

refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder described herein. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "thrombolytic" refers to any agent capable of inducing reperfusion by dissolving, dislodging or otherwise breaking up a clot, e.g., by either dissolving a fibrin-platelet clot, or inhibiting the formation of such a clot. Reperfusion occurs when the clot is dissolved and blood flow is restored. Exemplary thrombolytic agents include, but are not limited to, tissue-type plasminogen activator (t-PA), streptokinase (SK), prourokinase, urokinase (uPA), alteplase (also known as Activase®, Genentech, Inc.), reteplase (also known as r-PA or Retavase®, Centocor, Inc.), tenecteplase (also known as TNK™, Genentech, Inc.), Streptase® (AstraZeneca, LP), lanoteplase (Bristol-Myers Squibb Company), monteplase (Eisai Company, Ltd.), saruplase (also known as r-scu-PA and Rescupase™, Grunenthal GmbH, Corp.), staphylokinase, and anisoylated plasminogen-streptokinase activator complex (also known as APSAC, Anistreplase and Eminase®, SmithKline Beecham Corp.). Thrombolytic agents also include other genetically engineered plasminogen activators. The invention can additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10,000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, or portion thereof) described herein to bind to a target, such as DEspR, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody reagent is said to specifically bind an antigen when it preferentially recognizes its target antigen in a complex mixture of proteins and/or macromolecules.

In some embodiments, an antibody reagent as described herein binds to DEspR with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody reagent as described herein binds to DEspR with a dissociation constant ($K_D$) of from about $10^{-5}$ M to $10^{-6}$ M. In some embodiments, an antibody reagent as described herein binds to DEspR with a dissociation constant ($K_D$) of from about $10^{-6}$ M to $10^{-7}$M. In some embodiments, an antibody reagent as described herein binds to DEspR with a dissociation constant ($K_D$) of from about $10^{-7}$ M to $10^{-8}$ M. In some embodiments, an antibody reagent as described herein binds to DEspR with a dissociation constant ($K_D$) of from about $10^{-8}$ M to $10^{-9}$ M. In some embodiments, an antibody reagent as described herein binds to DEspR with a dissociation constant ($K_D$) of from about $10^{-9}$ M to $10^{-10}$ M. In some embodiments, an antibody reagent as described herein binds to DEspR with a dissociation constant ($K_D$) of from about $10^{-10}$ M to $10^{-11}$ M. In some embodiments, an antibody reagent as described herein binds to DEspR with a dissociation constant ($K_D$) of from about $10^{-11}$M to $10^{-12}$ M. In some embodiments, an antibody reagent as described herein binds to DEspR with a dissociation constant ($K_D$) of less than $10^{-12}$ M.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some embodiments of any of the aspects, the agent that inhibits DEspR is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or translation and/or activity of a target, e.g. DEspR. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art.

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2).nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of decreasing the survival and/or activity of a neutrophil, the method comprising contacting the neutrophil with a DEspR inhibitor.
2. A method of preventing or decreasing neutrophil extracellular trap (NET) release or actPMN NETosis in a subject in need thereof, the method comprising administering a therapeutically effective amount of a DEspR inhibitor to the subject.

3. The method of any one of paragraphs 1-2, wherein the neutrophil is an activated neutrophil (actPMN).
4. The method of any one of paragraphs 1-3, wherein the DEspR inhibitor is an anti-DEspR antibody reagent or an antigen-binding fragment thereof.
5. The method of paragraph 4, wherein the anti-DEspR antibody reagent is a bi-specific reagent that can bind specifically to i) DEspR and ii) PD1 or PD-L1.
6. A method of preventing or decreasing NET release or actPMN NETosis in a subject in need thereof, the method comprising administering a therapeutically effective amount of an anti-DEspR antibody reagent conjugated to an anti-neutrophil or anti-NET reagent to the subject.
7. The method of any one of paragraphs 1-6, wherein the anti-DEspR antibody reagent is a monoclonal antibody or an antigen-binding fragment thereof.
8. The method of paragraph 7, wherein the anti-DEspR antibody reagent is a bi-specific reagent that can bind specifically to i) DEspR and ii) PD1 or PD-L1.
9. The method of any one of paragraphs 1-8, wherein the antibody reagent has complementary determining regions selected from SEQ ID Nos: 1-3, 9-11, 17-19, 5-7, 13-15, 21-23, 25-27, 29-31, and 33-35.
10. The method of any one of paragraphs 1-9, wherein the subject is in need of treatment for a condition or disease wherein neutrophils contribute to pathogenesis or worsening of disease.
11. The method of paragraph 10, wherein the condition or disease is selected from the group consisting of: systemic inflammatory response syndrome; acute lung injury (ALI); acute respiratory distress syndrome (ARDS); multi-organ failure or multi-organ dysfunction syndrome from ARDS, sepsis, infections, or cytokine storms induced by drugs or any agent; ischemic or hemorrhagic stroke; ischemic or drug-induced hemorrhagic transformation in the brain, hemorrhagic encephalopathy, traumatic brain injury; anoxic brain injury, chronic kidney disease; cancer; an actPMN-dependent cancer; diabetes; deep vein thrombosis; cancer, cancer metastasis, systemic microthrombosis; atherosclerotic thrombosis; systemic lupus erythematosus (SLE); rheumatoid arthritis; COPD; cystic fibrosis; pulmonary disease; and Alzheimer's Disease.
12. The method of any one of paragraphs 1-11, wherein the subject is in need of treatment for cancer and has a PD-L1+/DespR+ tumor.
13. The method of any one of paragraphs 1-12, wherein the subject is in need of treatment for cancer and has previously been treated by tumor resection.
14. The method of any one of paragraphs 1-13, wherein the subject is further administered a further immunotherapy.
15. The method of any one of paragraphs 1-13, wherein the subject has previously been administered a further immunotherapy.
16. The method of any one of paragraphs 1-13, wherein the subject is resistant to treatment with a further immunotherapy.
17. The method of any one of paragraphs 1-13, wherein the subject has developed a toxicity from treatment with a further immunotherapy.
18. The method of any one of paragraphs 14-17, wherein the immunotherapy is a PD1 and/or PD-L1 inhibitor therapy.
19. The method of any one of paragraphs 1-18, wherein the subject is a mammal.
20. The method of any one of paragraphs 1-19, wherein the subject is a human.
21. The use of a DEspR inhibitor to decrease the survival and/or activity of a neutrophil, comprising contacting the neutrophil with the DEspR inhibitor.
22. The use of a DEspR inhibitor to prevent or decrease neutrophil extracellular trap (NET) release or actPMN NETosis in a subject in need thereof, comprising administering a therapeutically effective amount of the DEspR inhibitor to the subject.
23. The use of any one of paragraphs 21-22, wherein the neutrophil is an activated neutrophil (actPMN).
24. The use of any one of paragraphs 21-23, wherein the DEspR inhibitor is an anti-DEspR antibody reagent or an antigen-binding fragment thereof.
25. The use of paragraph 44, wherein the anti-DEspR antibody reagent is a bi-specific reagent that can bind specifically to i) DEspR and ii) PD1 or PD-L1.
26. The use of an anti-DEspR antibody reagent conjugated to an anti-neutrophil or anti-NET reagent to prevent or decrease NET release or actPMN NETosis in a subject in need thereof, comprising administering a therapeutically effective amount of the anti-DEspR antibody reagent conjugated to an anti-neutrophil or anti-NET reagent to the subject.
27. The use of any one of paragraphs 21-26, wherein the anti-DEspR antibody reagent is a monoclonal antibody or an antigen-binding fragment thereof.
28. The use of paragraph 27, wherein the anti-DEspR antibody reagent is a bi-specific reagent that can bind specifically to i) DEspR and ii) PD1 or PD-L1.
29. The use of any one of paragraphs 21-28, wherein the antibody reagent has complementary determining regions selected from SEQ ID Nos: 1-3, 9-11, 17-19, 5-7, 13-15, 21-23, 25-27, 29-31, and 33-35.
30. The use of any one of paragraphs 21-29, wherein the subject is in need of treatment for a condition or disease wherein neutrophils contribute to pathogenesis or worsening of disease.
31. The use of paragraph 30, wherein the condition or disease is selected from the group consisting of: systemic inflammatory response syndrome; acute lung injury (ALI); acute respiratory distress syndrome (ARDS); multi-organ failure or multi-organ dysfunction syndrome from ARDS, sepsis, infections, or cytokine storms induced by drugs or any agent; ischemic or hemorrhagic stroke; ischemic or drug-induced hemorrhagic transformation in the brain, hemorrhagic encephalopathy, traumatic brain injury; anoxic brain injury, chronic kidney disease; cancer; an actPMN-dependent cancer; diabetes; deep vein thrombosis; cancer, cancer metastasis, systemic microthrombosis; atherosclerotic thrombosis; systemic lupus erythematosus (SLE); rheumatoid arthritis; COPD; cystic fibrosis; pulmonary disease; and Alzheimer's Disease.
32. The use of any one of paragraphs 21-31, wherein the subject is in need of treatment for cancer and has a PD-L1+/DespR+ tumor.
33. The use of any one of paragraphs 21-32, wherein the subject is in need of treatment for cancer and has previously been treated by tumor resection.
34. The use of any one of paragraphs 21-33, wherein the subject is further administered a further immunotherapy.

35. The use of any one of paragraphs 21-33, wherein the subject has previously been administered a further immunotherapy.
36. The use of any one of paragraphs 21-33, wherein the subject is resistant to treatment with a further immunotherapy.
37. The use of any one of paragraphs 21-33, wherein the subject has developed a toxicity from treatment with a further immunotherapy.
38. The use of any one of paragraphs 34-37, wherein the immunotherapy is a PD1 and/or PD-L1 inhibitor therapy.
39. The use of any one of paragraphs 21-38, wherein the subject is a mammal.
40. The use of any one of paragraphs 21-39, wherein the subject is a human.

Some embodiments of the technology described herein can be defined according to any of the following numbered paragraphs:

1. A method of decreasing the survival and/or activity of a neutrophil, the method comprising contacting the neutrophil with a DEspR inhibitor.
2. A method of preventing or decreasing neutrophil extracellular trap (NET) release, or actPMN NETosis or vital NETosis in a subject in need thereof, the method comprising administering a therapeutically effective amount of a DEspR inhibitor to the subject.
3. The method of any one of paragraphs 1-2, wherein the neutrophil is an activated neutrophil (actPMN) or a CD1 b+ neutrophil.
4. The method of any of paragraphs 1-3, wherein the neutrophil or NET is DEspR$^+$.
5. The method of any one of paragraphs 1-3, wherein the DEspR inhibitor is an anti-DEspR antibody reagent or an antigen-binding fragment thereof.
6. The method of paragraph 4, wherein the anti-DEspR antibody reagent is a bi-specific reagent that can bind specifically to i) DEspR and ii) PD1 or PD-L1.
7. A method of preventing or decreasing NET release, vital NETosis, or actPMN NETosis in a subject in need thereof, the method comprising administering a therapeutically effective amount of an anti-DEspR antibody reagent conjugated to an anti-neutrophil or anti-NET reagent to the subject.
8. The method of any one of paragraphs 1-7, wherein the anti-DEspR antibody reagent is an anti-DEspR antibody reagent, a monoclonal antibody, or an antigen-binding fragment thereof.
9. The method of paragraph 8, wherein the anti-DEspR antibody reagent is a bi-specific antibody reagent that can bind specifically to and inhibit i) DEspR and ii) a target that modulates immune cell activity and/or survival selected from:
   a. a cell surface receptor;
   b. a ligand or extracellular protein;
   c. an intracellular protein.
10. The method of paragraph 9, wherein the cell surface receptor is PD1; CTLA-4; TLR-2; TLR-4; CD14; or CD168
11. The method of paragraph 9, wherein the ligand or extracellular protein is PD-L1; CD80: CD86; G-CSF; GM-CSF; myeloperoxidase; cathepsin-G; neutrophil elastase; or arginase-1.
12. The method of paragraph 9, wherein the intracellular protein is Mcl-1; cIAP2; STAT3; ERK1/2; petptidy-larginine deaminase (PAD4); galectin-1/3; or adenosine deaminase of RNA-1 (ADAR-1).
13. The method of any one of paragraphs 1-12, wherein the anti-DEspR antibody reagent or bi-specific antibody reagent comprises complementary determining regions selected from SEQ ID Nos: 1-3, 9-11, 17-19, 5-7, 13-15, 21-23, 25-27, 29-31, and 33-35.
14. The method of any of paragraphs 1-13, wherein the anti-DEspR antibody reagent or bi-specific antibody reagent is a hinge-stabilized IgG4 antibody reagent.
15. The method of paragraph 14, wherein the hinge-stabilized IgG4 antibody reagent comprises a S228P mutation relative to the wildtype IgG4 sequence.
16. The method of any of paragraphs 1-15, wherein a cell expressing the anti-DEspR antibody reagent or bi-specific antibody reagent comprises the antibody reagent which is being administered or provided in the contacting step.
17. The method of paragraph 16, wherein the cell is a T cell, CAR-T cell, or adoptively transferred T cell.
18. The method of paragraph 17, wherein the anti-DEspR antibody reagent or bi-specific antibody reagent is a CAR.
19. The method of any of paragraphs 1-18, wherein the DEspR inhibitor, anti-DEspR antibody reagent, or bi-specific antibody reagent is an antibody-drug conjugate comprising at least one anti-DEspR antibody reagent and at least one drug conjugated to the antibody reagent.
20. The method of paragraph 19, wherein the drug is selected from the group consisting of:
   a thrombolytic, a chemotherapeutic, a nanoparticle, a polypeptide, an imaging agent, fluorophore, a small molecule, an enzyme, a nucleic acid molecule, or a chemical.
21. The method of paragraph 20, wherein the chemotherapeutic is mertansine, emtansine, gemcitabine, temozolomide, paclitaxel, or cis/oxali-platin.
22. The method of paragraph 20, wherein the nanoparticle is an iron oxide-nanoparticle (IONP), polymeric nanoparticle, or gold nanoparticle, or chimeric nanoparticle.
23. The method of paragraph 20, wherein the enzyme is DNAseI, matrix metalloproteinase 1 (MMP1) matrix metalloproteinase 2 (MMP2), matrix metalloproteinase 3 (MMP3), a tissue inhibitor of metalloproteinases (TIMP), a protease, a recombinase, or a plasminogen activator.
24. The method of paragraph 20, wherein the chemical is 4-aminobenzoichydrazide or NX-059 nitrone.
25. The method of paragraph 20, wherein the polypeptide is chymostatin, angiopoietin 1/2, SDF-1.
26. The method of any one of paragraphs 1-25, wherein the subject is in need of treatment for a condition or disease wherein neutrophils; NETs; or NETosing or NETting neutrophils contribute to pathogenesis, chronicity, or worsening of disease.
27. The method of paragraph 26, wherein the condition or disease is selected from the group consisting of:
   systemic inflammatory response syndrome (SIRS); acute lung injury (ALI); acute respiratory distress syndrome (ARDS); multi-organ failure or multi-organ dysfunction syndrome (MODS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endothelial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis.

28. The method of any one of paragraphs 1-27, wherein the subject is in need of treatment for cancer.

29. The method of paragraph 28, wherein the subject has a PD-L1+/DespR+ tumor; increased levels of circulating or tumor DEspR+ neutrophils; increased levels of DEspR+ activated neutrophils; increased levels of NETs; increased plasma levels of neutrophil elastase (NE); increased plasma levels of neutrophil myeloperoxidase (MPO); or a tumor comprising one or more of: DEspR+ neutrophils; DEspR+ NETosing neutrophils; NETs; an increased level of a neutrophil released immune-suppressor; an increased level of citrullinated-histone-3; and increased level of a neutrophil stimulator.

30. The method of paragraph 29, wherein the neutrophil-released immune suppressor is arginase-1; PD-L1; myeloperoxidase (MPO); or neutrophil-elastase (NE); or cathepsin G (CG).

31. The method of paragraph 30, wherein the neutrophil stimulator is G-CSF, ET1, Hif1a, or a DAMP.

32. The method of any of paragraphs 1-31, wherein the cancer is pancreatic ductal adenocarcinoma; glioblastoma; lung cancer; triple negative breast cancer; melanoma; colorectal cancer, gastric cancer, or ovarian cancer.

33. The method of any one of paragraphs 1-32, wherein the subject is in need of treatment for cancer and has previously been treated by tumor resection.

34. The method of any one of paragraphs 1-33, wherein the subject is further administered a further immunotherapy or chemotherapy.

35. The method of any one of paragraphs 1-34, wherein the subject has previously been administered a further immunotherapy or chemotherapy.

36. The method of any one of paragraphs 1-35, wherein the subject is resistant to treatment with a further immunotherapy or chemotherapy.

37. The method of any one of paragraphs 1-36, wherein the subject has developed a toxicity from treatment with a further immunotherapy or chemotherapy.

38. The method of any one of paragraphs 1-37, wherein the immunotherapy is an immune checkpoint protein immunotherapy, T-cell co-stimulator; or CAR-T therapy.

39. The method of any one of paragraphs 1-38, wherein the immunotherapy is a PD1 and/or PD-L1 inhibitor therapy.

40. The method of any of paragraphs 1-39, wherein the chemotherapy is gemcitabine, paclitaxel, temozolomide, irinotecan, abraxane, a platinum-based chemotherapy, a cisplatin, an oxiloplatin, or combinations thereof.

41. The method of any one of paragraphs 1-40, wherein the subject is a mammal.

42. The method of any one of paragraphs 1-41, wherein the subject is a human.

43. The method of any of paragraphs 1-42, wherein the subject has or has been determined to have DEspR+ neutrophils.

44. A method of identifying a subject at risk of neutrophil extracellular trap (NET) release, vital NETosis or actPMN NETosis, the method comprising detecting the level of DEspR+ neutrophils in a sample obtained from the subject, wherein an increased level of DEspR+ neutrophils relative to a reference indicates the subject is at increased risk of neutrophil extracellular trap (NET) release, vital NETosis or actPMN NETosis.

45. A method of identifying a subject at risk of neutrophil extracellular trap (NET) release, vital NETosis or actPMN NETosis, the method comprising detecting the level of DEspR in neutrophils obtained from the subject, wherein an increased level of DEspR+ in the neutrophils relative to a reference indicates the subject is at increased risk of neutrophil extracellular trap (NET) release, vital NETosis or actPMN NETosis 46. The method of paragraphs 44 or 45, wherein the subject at increased risk of NET release, vital NETosis, or actPMN NETosis is at increased risk of life-threatening neutrophil-driven secondary tissue injury leading to organ dysfunction or multi-organ dysfunction or at increased risk of neutrophil-driven exacerbation of chronic disease, vascular disease, infections, thromboses.

47. A DEspR inhibitor for use in a method of decreasing the survival and/or activity of a neutrophil.

48. A DEspR inhibitor for use in a method of preventing or decreasing neutrophil extracellular trap (NET) release, or actPMN NETosis or vital NETosis in a subject in need thereof, the method comprising administering a therapeutically effective amount of the DEspR inhibitor to the subject.

49. The inhibitor of any one of paragraphs 47-48, wherein the neutrophil is an activated neutrophil (actPMN) or a CD11b+ neutrophil.

50. The inhibitor of any of paragraphs 47-49, wherein the neutrophil or NET is DEspR$^+$.

51. The inhibitor of any of paragraphs 47-50, wherein the DEspR inhibitor is an anti-DEspR antibody reagent or an antigen-binding fragment thereof.

52. The inhibitor of paragraph 51, wherein the anti-DEspR antibody reagent is a bi-specific reagent that can bind specifically to i) DEspR and ii) PD1 or PD-L1.

53. An anti-DEspR antibody reagent conjugated to an anti-neutrophil or anti-NET reagent for use in a method of preventing or decreasing NET release, vital NETosis, or actPMN NETosis in a subject in need thereof.

54. The inhibitor or reagent of any one of paragraphs 47-53, wherein the anti-DEspR antibody reagent is an anti-DEspR antibody reagent, a monoclonal antibody, or an antigen-binding fragment thereof.

55. The inhibitor or reagent of paragraph 54, wherein the anti-DEspR antibody reagent is a bi-specific antibody reagent that can bind specifically to and inhibit i) DEspR and ii) a target that modulates immune cell activity and/or survival selected from:
    a. a cell surface receptor;
    b. a ligand or extracellular protein;
    c. an intracellular protein.
56. The inhibitor or reagent of paragraph 55, wherein the cell surface receptor is PD1; CTLA-4; TLR-2; TLR-4; CD14; or CD168
57. The inhibitor or reagent of paragraph 55, wherein the ligand or extracellular protein is PD-L1; CD80: CD86; G-CSF; GM-CSF; myeloperoxidase; cathepsin-G; neutrophil elastase; or arginase-1.
58. The inhibitor or reagent of paragraph 55, wherein the intracellular protein is Mcl-1; cIAP2; STAT3; ERK1/2; petptidylarginine deaminase (PAD4); galectin-1/3; or adenosine deaminase of RNA-1 (ADAR-1).
59. The inhibitor or reagent of any of paragraphs 47-58, wherein the anti-DEspR antibody reagent or bi-specific antibody reagent comprises complementary determining regions selected from SEQ ID Nos: 1-3, 9-11, 17-19, 5-7, 13-15, 21-23, 25-27, 29-31, and 33-35.
60. The inhibitor or reagent of any of paragraphs 47-59, wherein the anti-DEspR antibody reagent or bi-specific antibody reagent is a hinge-stabilized IgG4 antibody reagent.
61. The inhibitor or reagent of any of paragraphs 47-60, wherein the hinge-stabilized IgG4 antibody reagent comprises a S228P mutation relative to the wildtype IgG4 sequence.
62. The inhibitor or reagent of any of paragraphs 47-61, wherein a cell expressing the anti-DEspR antibody reagent or bi-specific antibody reagent comprises the antibody reagent which is being administered or provided in the contacting step.
63. The inhibitor or reagent of paragraph 62, wherein the cell is a T cell, CAR-T cell, or adoptively transferred T cell.
64. The inhibitor or reagent of paragraph 63, wherein the anti-DEspR antibody reagent or bi-specific antibody reagent is a CAR.
65. The inhibitor or reagent of any of paragraphs 47-64, wherein the DEspR inhibitor, anti-DEspR antibody reagent, or bi-specific antibody reagent is an antibody-drug conjugate comprising at least one anti-DEspR antibody reagent and at least one drug conjugated to the antibody reagent.
66. The inhibitor or reagent of paragraph 65, wherein the drug is selected from the group consisting of:
    a thrombolytic, a chemotherapeutic, a nanoparticle, a polypeptide, an imaging agent, fluorophore, a small molecule, an enzyme, a nucleic acid molecule, or a chemical.
67. The inhibitor or reagent of paragraph 66, wherein the chemotherapeutic is mertansine, emtansine, gemcitabine, temozolomide, paclitaxel, or cis/oxali-platin.
68. The inhibitor or reagent of paragraph 66, wherein the nanoparticle is an iron oxide-nanoparticle (IONP), polymeric nanoparticle, or gold nanoparticle, or chimeric nanoparticle.
69. The inhibitor or reagent of paragraph 66, wherein the enzyme is DNAseI, matrix metalloproteinase 1 (MMP1) matrix metalloproteinase 2 (MMP2), matrix metalloproteinase 3 (MMP3), a tissue inhibitor of metalloproteinases (TIMP), a protease, a recombinase, or a plasminogen activator.
70. The inhibitor or reagent of paragraph 66, wherein the chemical is 4-aminobenzoichydrazide or NX-059 nitrone.
71. The inhibitor or reagent of paragraph 66, wherein the polypeptide is chymostatin, angiopoietin 1/2, SDF-1.
72. The inhibitor or reagent of any of paragraphs 47-71, wherein the subject is in need of treatment for a condition or disease wherein neutrophils; NETs; or NETosing or NETting neutrophils contribute to pathogenesis, chronicity, or worsening of disease.
73. The inhibitor or reagent of paragraph 72, wherein the condition or disease is selected from the group consisting of:
    systemic inflammatory response syndrome (SIRS); acute lung injury (ALI); acute respiratory distress syndrome (ARDS); multi-organ failure or multi-organ dysfunction syndrome (MODS) from, e.g., ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections, or cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities (e.g., thrombosis and endothelial dysfunction) in kidney dialysis patients; ischemic or drug-induced hemorrhagic transformation in the brain, hemorrhagic encephalopathy, traumatic brain injury; anoxic brain injury, chronic kidney disease; cancer; an actPMN-dependent cancer; diabetes; type 1 diabetes; type 2 diabetes; angiopathies; vasculopathies; end-organ complications (e.g., retinopathy or diabetic kidney disease); poor wound healing of diabetic ulcers; deep vein thrombosis; cancer metastasis; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; sickle cell disease; inflammatory bowel disease (IBD); Crohn's disease; ulcerative colitis; and indeterminate colitis.
74. The inhibitor or reagent of any of paragraphs 47-73, wherein the subject is in need of treatment for cancer.
75. The inhibitor or reagent of paragraph 74, wherein the subject has a PD-L1+/DespR+ tumor; increased levels of circulating or tumor DEspR+ neutrophils; increased levels of DEspR+ activated neutrophils; increased levels of NETs; increased plasma levels of neutrophil elastase (NE); increased plasma levels of neutrophil myeloperoxidase (MPO); or a tumor comprising one or more of:
    DEspR+ neutrophils; DEspR+ NETosing neutrophils; NETs; an increased level of a neutrophil released immune-suppressor; an increased level of citrullinated-histone-3; and increased level of a neutrophil stimulator.
76. The inhibitor or reagent of paragraph 75, wherein the neutrophil-released immune suppressor is arginase-1;

PD-L1; myeloperoxidase (MPO); or neutrophil-elastase (NE); or cathepsin G (CG).
77. The inhibitor or reagent of paragraph 76, wherein the neutrophil stimulator is G-CSF, ET1, Hif1a, or a DAMP.
78. The inhibitor or reagent of any of paragraphs 47-77, wherein the cancer is pancreatic ductal adenocarcinoma; glioblastoma; lung cancer; triple negative breast cancer; melanoma; colorectal cancer, gastric cancer, or ovarian cancer.
79. The inhibitor or reagent of any of paragraphs 47-78, wherein the subject is in need of treatment for cancer and has previously been treated by tumor resection.
80. The inhibitor or reagent of any of paragraphs 47-79, wherein the subject is further administered a further immunotherapy or chemotherapy.
81. The inhibitor or reagent of any of paragraphs 47-80, wherein the subject has previously been administered a further immunotherapy or chemotherapy.
82. The inhibitor or reagent of any of paragraphs 47-81, wherein the subject is resistant to treatment with a further immunotherapy or chemotherapy.
83. The inhibitor or reagent of any of paragraphs 47-82, wherein the subject has developed a toxicity from treatment with a further immunotherapy or chemotherapy.
84. The inhibitor or reagent of any of paragraphs 47-83, wherein the immunotherapy is an immune checkpoint protein immunotherapy, T-cell co-stimulator; or CAR-T therapy.
85. The inhibitor or reagent of any of paragraphs 47-84, wherein the immunotherapy is a PD1 and/or PD-L1 inhibitor therapy.
86. The inhibitor or reagent of any of paragraphs 47-85, wherein the chemotherapy is gemcitabine, paclitaxel, temozolomide, irinotecan, abraxane, a platinum-based chemotherapy, a cisplatin, an oxiloplatin, or combinations thereof.
87. The inhibitor or reagent of any of paragraphs 47-86, wherein the subject is a mammal.
88. The inhibitor or reagent of any of paragraphs 47-87, wherein the subject is a human.
89. The inhibitor or reagent of any of paragraphs 47-88, wherein the subject has or has been determined to have DEspR+ neutrophils.

EXAMPLES

Example 1: Anti-DEspR Therapy in Maladaptive Neutrophil-Excess Mediated Pathology This invention relates to anti-DEspR technologies which inhibit or abrogate the extended survival mechanisms in activated neutrophils ($IC_{50}$<8 nM) thus inhibiting all activated neutrophil activity that drives and reciprocally interacts with other cell players towards a maladaptive pathogenic cascade. The actPMN-driven pathogenic cascade results in a rapid feed-forward reciprocal interaction toward disease progression, and subsequent debilitating sequelae or death.

This invention further relates to compositions comprising DEspR-inhibiting compounds and methods of using these DEspR-inhibiting compounds for the treatment of conditions or diseases that involve pathogenic cascades induced, driven and/or propagated by activated neutrophils (actPMNs) and/or by NETosis.

Neutrophils are polymorphic nuclear cells (PMCs) with 2-5 lobes in their nucleus, and are the most abundant type of white blood cells in humans. Under physiologic conditions, neutrophils are constitutively apoptotic with short circulating half-life of 6-8 hrs. Upon activation as occurs in inflammation, neutrophils have extended survival or delayed apoptosis (beyond 1-2 days) in order to fulfill their vital roles in defending the host against invading pathogens. Neutrophils are first-responders in innate immunity and within minutes localize to sites of injury or infection. They are the hallmark of inflammation capable of 1) killing bacteria upon release of radical oxygen species, protease, myeloperoxidase, elastase; as well as capable of 2) trapping bacteria physically and killing them in neutrophil extracellular traps (NETs)— "web-like structures made up of decondensed chromatin fibers 15-17 nm diameters, histones and DNA containing antimicrobial enzymes."

However, the very same bacterial killing mechanisms can result in maladaptive pathogenic cascades that cause tissue injury directly (much like killing bacteria), the neutrophil paradox. Moreover, the activated neutrophil's maladaptive effects are expanded by crosstalk between activated neutrophils and other cells (lymphocytes, antigen-presenting cells, endothelial cells, cancer cells) through mediators such as cytokines, setting up feed-forward reciprocal interactions. The very same NETs can cause thrombosis—as seen in deep vein thrombosis and in cancer microthrombosis as well as in atherosclerotic thrombosis.

Activated neutrophil-mediated tissue injury mechanisms can drive pathogenic cascades in different organ system diseases such as the following examples (not all inclusive).
  the lungs in acute lung injury (ALI) and acute respiratory distress syndrome (ARDS)
  in hemorrhagic transformation in stroke,
  in chronic kidney disease
  in aggressive cancer and metastasis [refs. 13-25]
    High neutrophil counts (high neutrophil-to-lymphocyte ratios, NLR) are associated with poor clinical outcome in multiple human cancer types: pancreatic ductal adenocarcinoma, hepatocellular, colorectal, renal, non-small cell lung cancer melanoma, gastric, glioblastoma, and head and neck cancers.
    Neutrophils are active players in tumor progression and promote aggressive tumor growth with epithelial to mesenchymal transition and increased metastatic potential, seen in pancreatic ductal adenocarcinoma, breast and colorectal cancers
  thrombosis thru NETosis
    NETS promote thrombosis by providing a scaffold for platelet and RBC adhesion and aggregation and enhancing coagulation. NETosis associated thrombi and NETosis markers correlate with thrombotic diseases activity as reported in thrombotic microangiopathies in cancer, deep vein thrombosis, and in atherothrombosis
  in diabetes poor wound healing
  in several pulmonary diseases:
    The detrimental effect of excessive NET release is particularly important to lung diseases, because NETs can expand more easily in the pulmonary alveoli, causing lung injury. Moreover, NETs and its associated molecules are able to directly induce epithelial and endothelial cell death. In this regard, massive NET formation has been reported in several pulmonary diseases, including asthma, chronic obstructive pulmonary disease, cystic fibrosis, respiratory syncytial virus bronchiolitis, influenza, bacterial pneumonia, and tuberculosis, among others. Thus, NET formation must be tightly regulated in order to avoid NET-mediated tissue damage.

in Alzheimer's Disease

Excessive and uncontrolled neutrophil functional activity and excess NETosis in multiple diseases [refs 8-35] contribute to a 'feeding-frenzy-like' pathogenic cascade that is hard to stop. Novel therapies are needed. To date, potential new therapies have failed to demonstrate efficacy, as seen in acute lung injury and acute respiratory distress syndrome.

Because of the rapid pace of activated neutrophil-driven pathogenic cascade, a quick-response therapy is needed as provided, e.g., by anti-DEspR humab therapy as described herein. Just as anti-DEspR decreases survival of CSCs, anti-DEspR abrogates the extended survival in activated neutrophils, hence preventing maladaptive excessive neutrophil-mediated tissue injury and NET-mediated pathogenic cascades.

Anti-DEspR re-engages the neutrophil's apoptosis mechanisms by blocking STAT3-mediated upregulation of Mcl1, as well as causes decreased Mcl1. Mcl1 is implicated in the extended survival of activated neutrophils, which in the quiescent state are constitutively apoptotic. By inducing apoptosis of activated neutrophils (which are phagocytosed by macrophages), anti-DEspR prevents the pathogenic cascade of neutrophil-mediated tissue injury (via proteases, cathepsin G, proteinase 3, myeloperoxidase). Prevention of activated neutrophil progression to NETosis, thus prevents NET-mediated pathogenic cascades in non-infectious diseases. Anti-DEspR can also be used as a targeting moiety for nanoconjugates/drug conjugates targeting activated neutrophil infiltrates, circulating neutrophils, and NETs in the circulation or in tissues (e.g., lungs, joints, muscle, heart, etc) or in pathologies (e.g., thrombus, tumors, ulcers, wounds).

Anti-DEspR mAb therapy for excessive neutrophil-mediated feeding-frenzy-like pathogenic cascades.

Figure 1C:
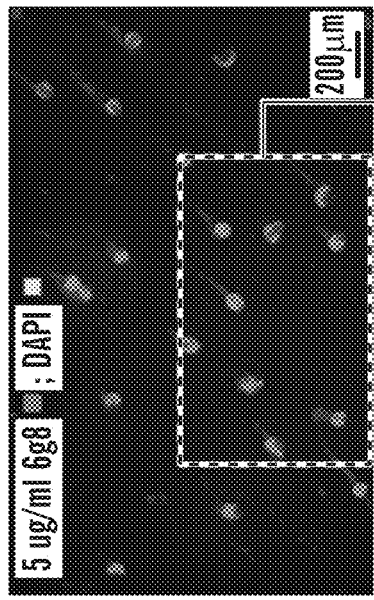
FIGS. 1A-1D depict DEspR expression on human activated neutrophils detected by anti-DEspR murine mAb, 6g8, prototype to humanized anti-DEspR mAbs, 6g8-IgG4 humab.
Figure 1D:
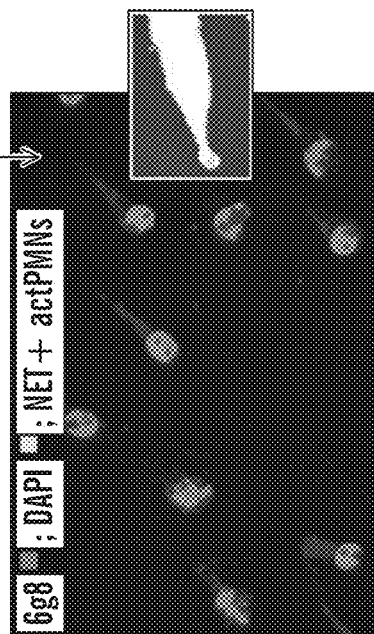
Figure 1A:
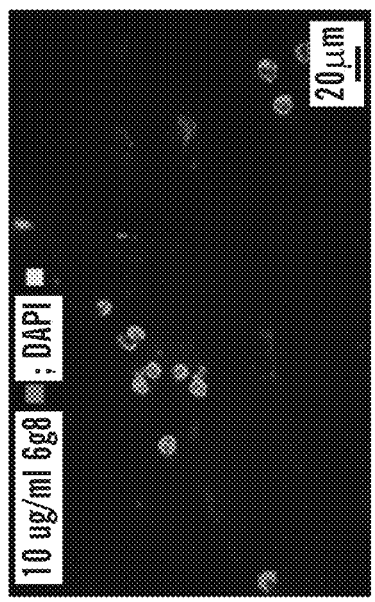
Figure 1B:
Figure 2B:
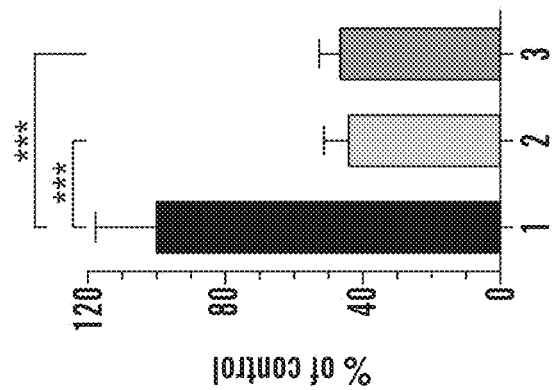
FIGS. 2A-2B depict DEspR expression on rat activated neutrophils and anti-DEspR inhibition of activated neutrophil survival.
Figure 2A:
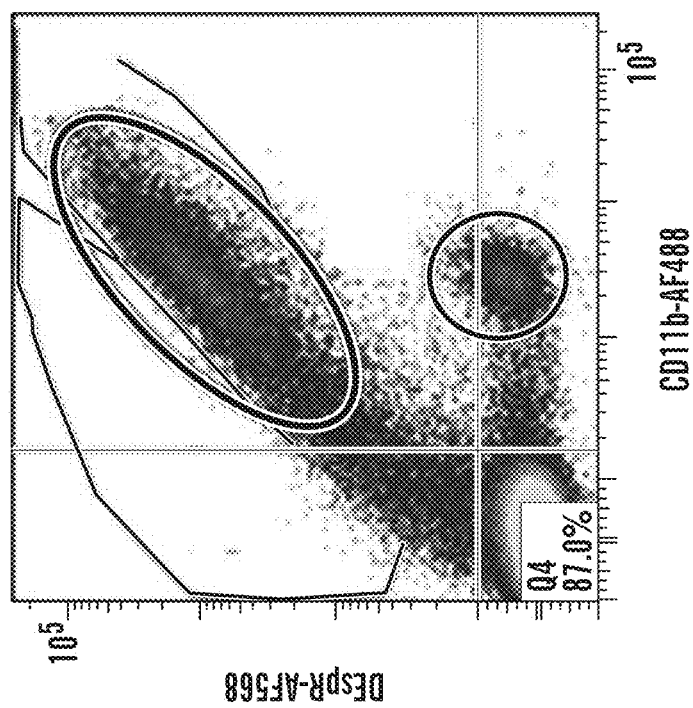

DEspR is expressed on activated human neutrophils (FIG. 1A) and in neutrophils undergoing NETosis (FIG. 1C-D), in contrast to isotype control (FIG. 1B). Anti-DEspR mAb detects DEspR expression on rat LPS-activated neutrophils (FIG. 2A). Notably, low-dose (1-2 mg/kg/dose instead of usual 15-20 mg/kg/dose) lipopolysaccharide activated neutrophils as marked by CD11b (Mac1) induction compared to non-activated or quiescent neutrophils (Q4). Majority of CD11b activated neutrophils are DEspR+(Red bold circle) in contrast to CD11b+ but DEspR(−) (yellow circle) activated neutrophils (FIG. 2A). Ex vivo, anti-DEspR mabs [anti-ratDEspR 10a3 lane 2, and pan-species reactive anti-Human/Rat/Monkey DEspR mAb, 6g8], treatment of activated neutrophils decreased their survival in contrast to control non-treated activated neutrophils (1-way ANOVA, Tukey's post-hoc multiple comparisons P<0.0001) (FIG. 2B).

Figure 5:
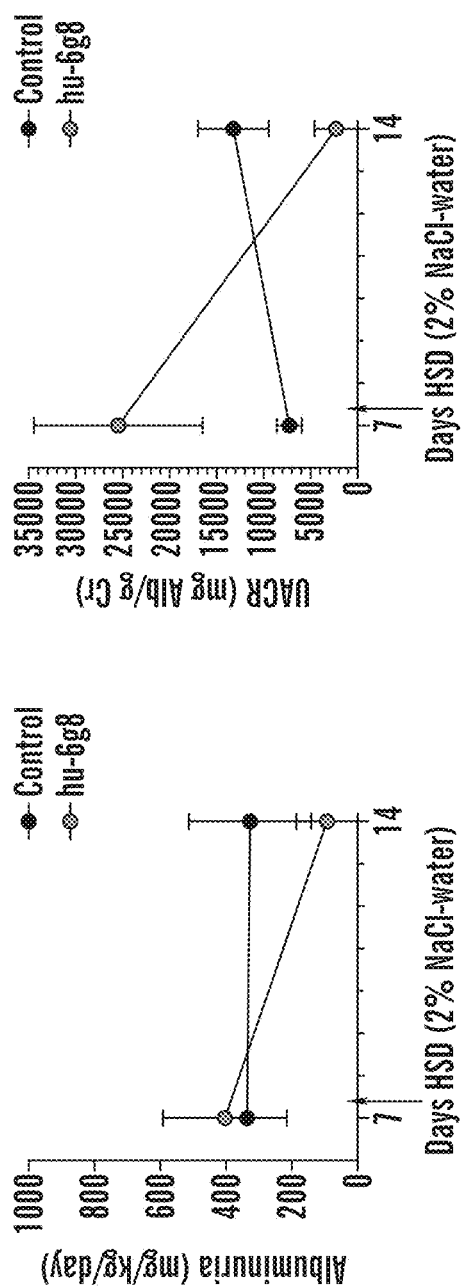
FIG. 5. demonstrates that anti-DEspR mAb (hu-6g8) (3 mg/kg iv dose×1 dose given after baseline sampling) decreased albuminuria, urinary albumin creatinine ratio (UACR) in female rats with moderate-severe chronic kidney disease~Stage 4 (4) and Stage 5 (5). Legend: hu-6g8, humanized anti-DEspR monoclonal antibody, HSD, high salt diet induced via 2% NaCl water to drink ad lib; CKD, Dahl salt-sensitive hypertensive rats with chronic kidney disease with moderate nephrosclerosis (Raij scores~300) induced with a high salt diet (2% NaCl); control, non-treated age- and sex-matched CKD rats.

In vivo efficacy: anti-DEspR mAb decreases the albuminuria/proteinuria in both female (Table 1) and male (Table 2) hypertensive rats with moderate-severe chronic kidney disease (FIG. 5).

Figure 3A:
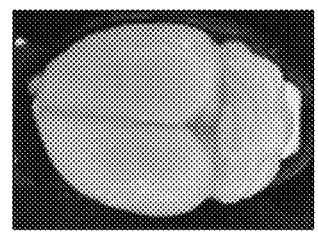
Figure 3B:
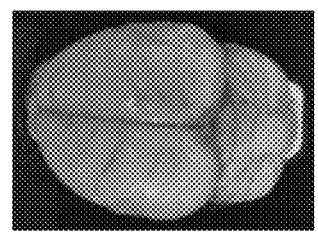
Figure 3C:
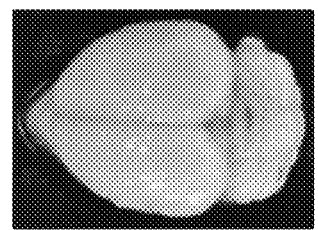

As shown in FIG. 3A-3F, low-dose LPS 1.8 mg/kg/dose in stroke prone rats induced severe hemorrhagic encephalitis in 24 hours (FIG. 3B) compared with control normal rat brain (FIG. 3A). Importantly, one-time treatment with anti-DEspR mAb (1 mg/kg/dose iv) attenuated the progression to life-threatening hemorrhagic encephalitis (FIG. 3C). As confirmation of anti-DEspR targeted effects, we demonstrate target engagement by detecting anti-DEspR murine IgG in the brain of treated rats (FIG. 3D) in contrast to control normal brain with no LPS-induced hemorrhagic encephalitis, and control non-treated LPS-induced hemorrhagic encephalitis rat brains (FIG. 3D). Concordantly, decrease in functional activity of activated neutrophils is detected with decreased myeloperoxidase levels in the treated rat brains compared to the control non-treated LPS-induced hemorrhagic encephalitis rat brain (FIG. 3E). Brain myeloperoxidase levels are increased upon released by activated neutrophils, hence the observed decrease indicates decrease in activated neutrophils in the brain.

To further confirm in vivo efficacy in abrogating neutrophils, we analyzed and detected a decrease in brain albumin content indicating a decrease in brain edema (FIG. 3F). A decrease in brain edema indicates blood brain barrier stabilization by the anti-DEspR-mediated attenuation of activated neutrophils-mediated hemorrhagic encephalopathy. Neutrophil-mediated tissue injury has been implicated in blood brain barrier disruption or injury.

Figure 4:
FIG. 4 depicts a survival curve analysis of anti-DEspR treated rats compared with non-treated rats in a rat model of LPS-induced multi-organ failure manifesting predominantly as hemorrhagic encephalopathy (phenotype corroborated in FIG. 3A-3F).

In order to demonstrate anti-DEspR effects on a clinically relevant outcome, we determined whether anti-DEspR can increase survival of rats with acute onset LPS-induced hemorrhagic encephalopathy. As shown in FIG. 4, anti-DEspR mAb treatment increased survival in ⅝ rats treated, with 50% (⅘) of the treated rats reaching complete response and aborting risk of death, Survival Analysis p=0.0007.

In vivo efficacy: anti-DEspR mAb decreases the albuminuria/proteinuria in both female (Table 1) and male (Table 2) hypertensive rats with moderate-severe chronic kidney disease (FIG. 5).

Summary of Findings in Female Rats with Chronic Kidney Disease.

TABLE 1

Effect of hu-6g8 on CKD in Dahl S female rats fed a HSD.

| Group | D7 | D14 | % Change |
|---|---|---|---|
| Albuminuria (mg/kg/day) | | | |
| Control | 336 ± 7.8 | 327 ± 186 | — |
| hu-6g8 | 404 ± 190 | 92.5 ± 95 | ↓ 77 |
| Creatinine Clearance (µL/min) | | | |
| Control | 292 ± 101 | 135 ± 49 | ↓ 54 |
| hu-6g8 | 104 ± 35 | 168 ± 118 | ↑ 62 |
| UACR | | | |
| Control | 7278 ± 1303 | 13187 ± 3800 | ↑ 81 |
| Hu-6g8 | 25450 ± 8980 | 2285 ± 2337 | ↓ 91 |
| Urinary Exosome Excretion (mg/kg/day) | | | |
| Control | 494 ± 45 | 792 ± 405 | ↑ 60 |
| Hu-6g8 | 663 ± 224 | 876 ± 348 | ↑ 32 |

Dahl S female rats 20 weeks of age at D0;
HSD, high salt diet (2% NaCl in drinking water, D0-D14);
% Change, % change from D7;
hu-6g8 3 mg/kg IV at D7;
UACR, urinary albumin/urinary creatinine ratio.
Data shown as Mean ± SD.

TABLE 2

Effect of hu-6g8 on CKD in Tg25+ male rats fed a HSD.

| Group | D14 | D28 | % Change |
|---|---|---|---|
| Albuminuria (mg/kg/day) | | | |
| Control | 179 ± 34.5 | 217 ± 87 | ↑ 21 |
| Hu-6g8 | 217 ± 87 | 164.8 ± 86 | ↓ 24 |

TABLE 2-continued

Effect of hu-6g8 on CKD in Tg25+ male rats fed a HSD.

| Group | D14 | D28 | % Change |
|---|---|---|---|
| Creatinine Clearance (μL/min) | | | |
| Control | 225 ± 117 | 309 ± 102 | ↑ 37 |
| Hu-6g8 | 279 ± 82 | 268 ± 30 | ↓ 4 |
| UACR | | | |
| Control | 7398 ± 1372 | 12910 ± 7665 | ↑ 75 |
| Hu-6g8 | 8309 ± 3731 | 5567 ± 2210 | ↓ 33 |
| Urinary Exosome Excretion (mg/kg/day) | | | |
| Control | 604 ± 283 | 761 ± 500 | ↑ 26 |
| Hu-6g8 | 771 ± 220 | 651 ± 191 | ↓ 16 |

Tg25+ male rats 12 weeks of age at D0;
HSD, high salt diet (8% NaCl food pellets D0-D21;
2% NaCl in drinking water, D21-D28);
% Change, % change from D14;
hu-6g8 3 mg/kg IV at D0, D7, D14 and D21;
UACR, urinary albumin/urinary creatinine ratio.
Data shown as Mean ± SD.

Figure 6:
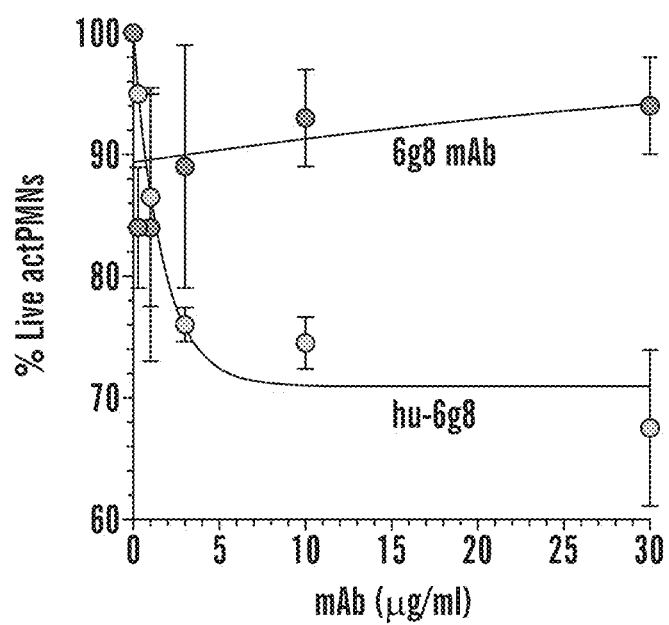
FIG. 6 depicts a graph comparison of functional activity of anti-DEspR fully humanized 6g8 mAb, 6g8-humab, and prototype murine anti-DEspR 6g8 mAb, 6g8-mumab. In in vitro assays of inhibition of survival with and without anti-DEspR mAb treatment, the 6g8-humab exhibited improved $IC_{50}$<8 nM (7.7 nM±2.0) compared with 6g8 mumab ($IC_{50}$>200 nM or (>30 μg/ml), the maximum dose used in the dose-response survival assay. Live cells were counted using Trypan blue dye exclusion assay.

Fully humanized anti-DEspR 6g8-IgG4 humab, hu-6g8, inhibits activated neutrophil survival with improved $IC_{50}$ compared to counterpart anti-DEspR 6g8-murine mAb (FIG. 6).

Figure 7:
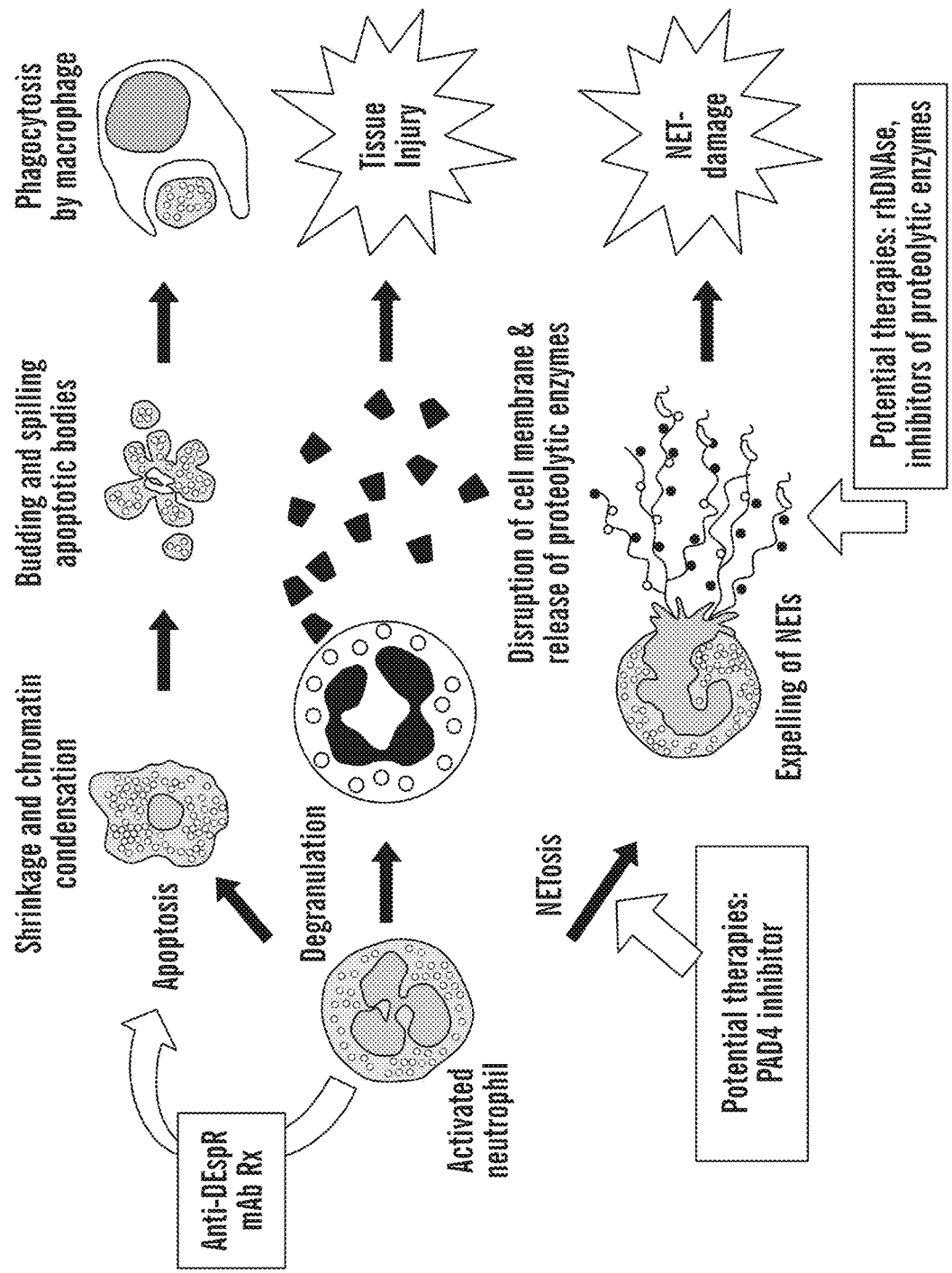
FIG. 7 depicts a diagram of activated neutrophil antibacterial functions which become maladaptive when in excess and dysregulated. Sites targeted by different therapies marked.
Figure 8:
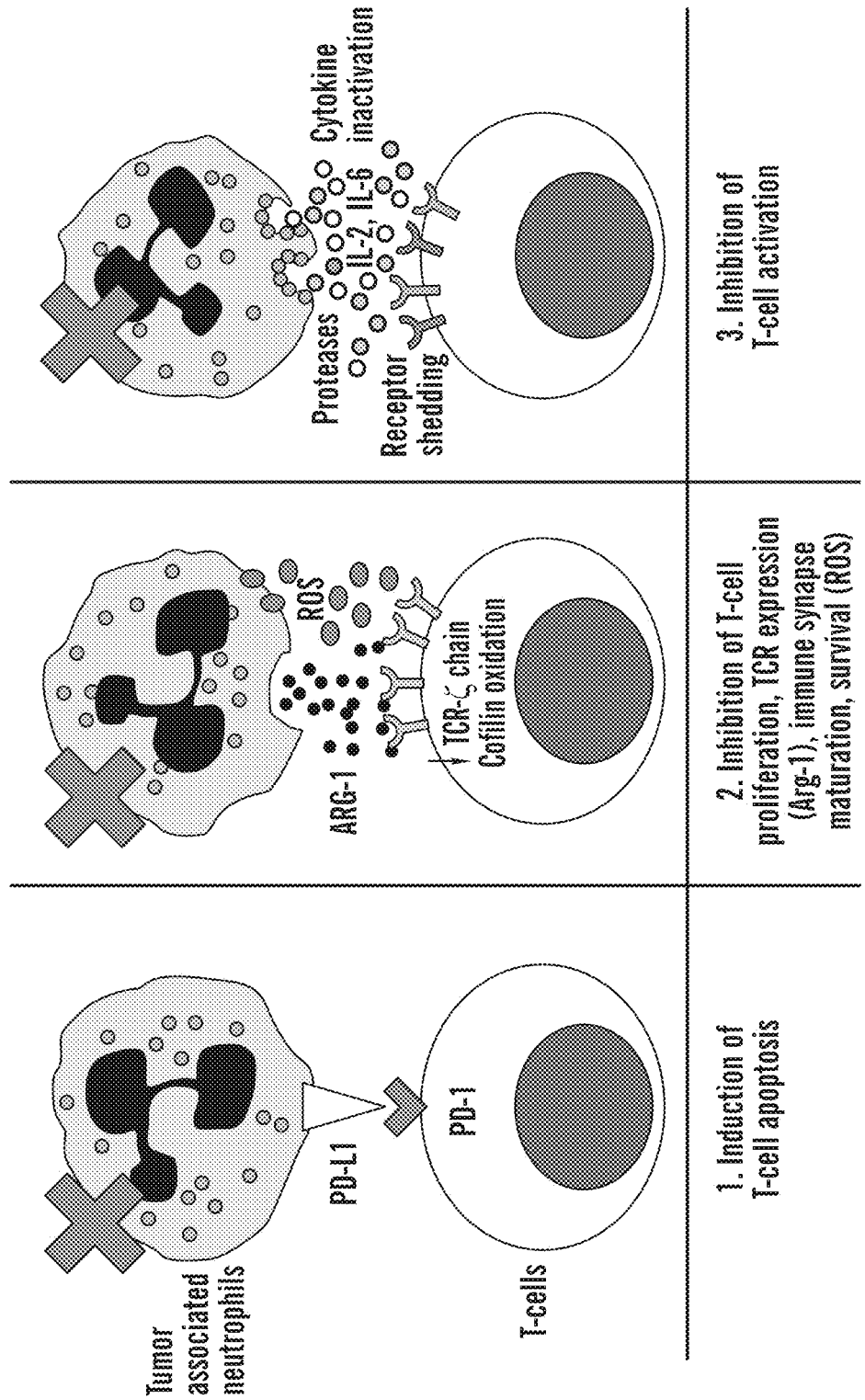
FIG. 8 depicts a diagram of neutrophil mechanisms (#1-#3) of T-cell inhibition promoting immune evasion in tumors, and hence anti-DEspR induction of apoptosis or decrease of survival of activated neutrophils eliminates neutrophil-mediated immune evasion. #1) induction of T-cell apoptosis, #2) inhibition of T-cell proliferation and T-cell receptor ζ-chain expression by neutrophil released arginase-1, and T-cell immune synapse maturation and survival by oxidation of cofilin by neutrophil-released reactive oxygen species (ROS); and #3) inhibition of T-cell activation via release of proteases (cathepsin G, elastase) that breaks down T-cell stimulating cytokines (IL-2, IL-6) and induces receptor shedding. The diagram demonstrates how activated neutrophils in tumors contribute to tumor immune-evasion, and how anti-DEspR induced programmed cell death of activated neutrophils hence eliminates activated neutrophils (X) also leads to elimination of multiple mechanisms of neutrophil-mediated immune-evasion in tumors.

A schematic overview of potential therapies to abrogate NET-mediated pathogenic cascades is provided in FIG. 7. Anti-DEspR mAb therapy aims to revert the extended-survival of activated neutrophils toward apoptosis in order to stop tissue injury from excessive neutrophil release of proteolytic enzymes [Degranulation] and NETosis.

REFERENCES

Summers C, et al. 2010. Neutrophil kinetics in health and disease. Trends Immuno 31:318-324.
Yang H et al. 2016. New insights into neutrophil extracellular traps: mechanisms of formation and role in inflammation. Frontiers in Immunol 7: Article 302.
Cohen S, 2002. Cohen, Stephen; Burns, Richard C. (2002). Pathways of the Pulp (8th ed.). St. Louis: Mosby. p. 465
Brinkmann V et al. 2004. Neutrophil extracellular traps kill bacteria. Science 303:12-15. Yang H et al 2016.
Leliefeld P H C, Koenderma L, Pillay J. 2015. How neutrophils shape adaptive immune responses. Frontiers in Immunology. 14 Sep. 2015, 6: Article 471.
Fuchs T A, et al. 2010. Proc Natl Acad Sci. Sep. 7; 107(36):15880-15885.
Martinod K, Wagner D D. 2014. Thrombosis: tangled up in NETs. Blood 123:2768-2776.
Grommes J, Soehnlein O. 2011. Contributio of neutrophils to acute lung injury. Mo Med 17:293-307.
Abraham E. 2003. Neutrophils and acute lung injury. Crit Care Med 31:5195-5199.
Jickling G C et al. Targeting neutrophils in ischemic stroke: translational insights from experimental studies. J Cerb Blood Flow Metab 35:888-901.
Kato S, et al. 2015. Neutrophil/lymphocyte ratio: a promising prognostic marker in patients with chronic kidney disease. Inflammation Cell Signaling 2015, 2:e683.
Perez-de-Puig I., et al. Neutrophil recruitment to the brain in mouse and human ischemic stroke. Acta Neuropathol 2015 February; 129(2):239-57
Dumitru C A, Lang S, Brandau S. 2013. Modulation of neutrophil granulocytes in the tumor microenvironment: mechanisms and consequences for tumor progression.
Steele C W, et al. 2016. CXCR2 inhibition profoundly suppresses metastases and augments immunotherapy in pancreatic ductal adenocarcinoma. Cancer Cell 29:832-845.
He G, et al. 2015. Peritumoral neutrophils negatively regulate adaptive immunity via the PD-L1/PD-1 signaling pathway in hepatocellular carcinoma. J Exp Clin Cancer Research 34:141.
Rao H L, et al. 2012. Increased intratumoral neutrophil in colorectal carcinomas correlates closely with malignant phenotype and predicts patients' adverse prognosis. PLoS One 2012:7:e30806.
Li Y W, et al. 2011. Intratumoral neutrophils: a poor prognostic factor for hepatocellular carcinoma following resection J Hepatol 54:948-955.
Jensen H K, et al. 2009. Presence of intratumoral neutrophils is an independent prognostic factor in localized renal cell carcinoma. J Clin Oncol 27:4709-4717.
Ilie M et al. 2011. Predictive clinicl outcome of the intratumoral CD66b-positive neutrophil-to-CD8+ T-cell ratio in patients with resectable non-small cell lung cancer. Cancer 118:1726-1737,
Jensen T O, et al., 2012. Intratumoral neutrophils and plasmacytoide dendritic cells indicate poor prognosis and are associated with pSTAT3 expression in JCC stage I/II melanoma. Cancer 118:2476-2485.
Zhao J J, et al. 2012. The prognostic value of tumor-infiltrating neutrophils in gastric adenocarcinoma after resection. PLoS One 2012:7:e33655.
Fossati G, et al. 1999. Neutrophil infiltration into human gliomas. Act Neuropathologica 98:349-354.
Dumitru C A, et al. 2011. Tumor-derived macrophage migration inhibitory factor modulates the biology of head and neck cancer cells via neutrophil activation. Int J Cancer 129:859-869.
Felix K, Gaida M M. 2016. Neutrophil-derived proteases in the microenvironment of pancreatic cancer—active players in tumor progression. Int J Biol Sci 12:302-313.
TenKate M, et al. 2007. Polymorphonuclear leukocytes increase the adhesion of circulating tumor cells to microvascular endothelium. Anticancer Res 27:17-22.
Demers M, Wagner D D. 2014. NETosis: a new factor in tumor progression and cancer-associated thrombosis. 40:277-283.
Fuchs et al 2010.
Massberg S, et al. 2010. Reciprocal coupling of coagulation and innate immunity via neutrophil serine proteases Nat Med 16:887-896.
Demers M 2014.
Diaz J A, et a. 2013. Plasma DNA is elevated in patients with deep vein thrombosis. J Vasc Surg Venous Lymphat Disord 1:341-348.
vanMontfoort M L, et al. circulating nucleosomes and neutrophil activation as risk factors for deep vein thrombsosi. Arterioscler Thromb Vasc Biol 33:147-151.
Borissoff J I, et al. 2013. Elevated levels of circulating DNA and chromatin are independently associated with severe coronary atherosclerosis and a prothrombotic state. Arterioscler Thromb Vasc Biol 33:2032-2040.
Wong S L et al. 2015. Diabetes primes neutrophils to undergo NETosis, which impairs wound healing. Nature Med 21:815-819.
Fadini G P, et al. 2016. NETosis delays diabetic wound healing in mice and humans. Diabetes 65:1061-1071.
Porto B N, Stein R T. 2016. Neutrophil extracellular traps in pulmonary diseases: too much of a good thing? Fron Immunol 2016 Aug. 15:7:311.

Zenaro E et al. 2015. Neutrophils promote Alzheimer's disease-like pathology and cognitive decline via LFA-1 integrin. Nat Med 21:880-886.

Yamashita C M, Lewis J F. 2012. Emerging therapies for treatment of acute lung injury and acute respiratory distress syndrome.

Liu H, et al. 2003. Serine phosphorylation of STT3 is essential for Mcl-1 expression and macrophage survival. Blood 102:344-352.

Michael J. Hickey & Paul Kubes. 2009. Nature Reviews Immunology 9, 364-375.

Williams A E, Chambers R C. 2014. The mercurial nature of neutrophils: still an enigma in ARDS? Am J Physiol Lung Cell Mol Physiol 308: L217-L230.

Iba T et al. 2013. Neutrophil extracellular traps, damage-associated molecular patterns, and cell death during sepsis. Acute Med Surg doi: 10/1002/ams2.10.

Example 2: Anti-DEspR mAb Therapy [Hu-6g8]: Efficacy-Safety Advantages

Figure 16:
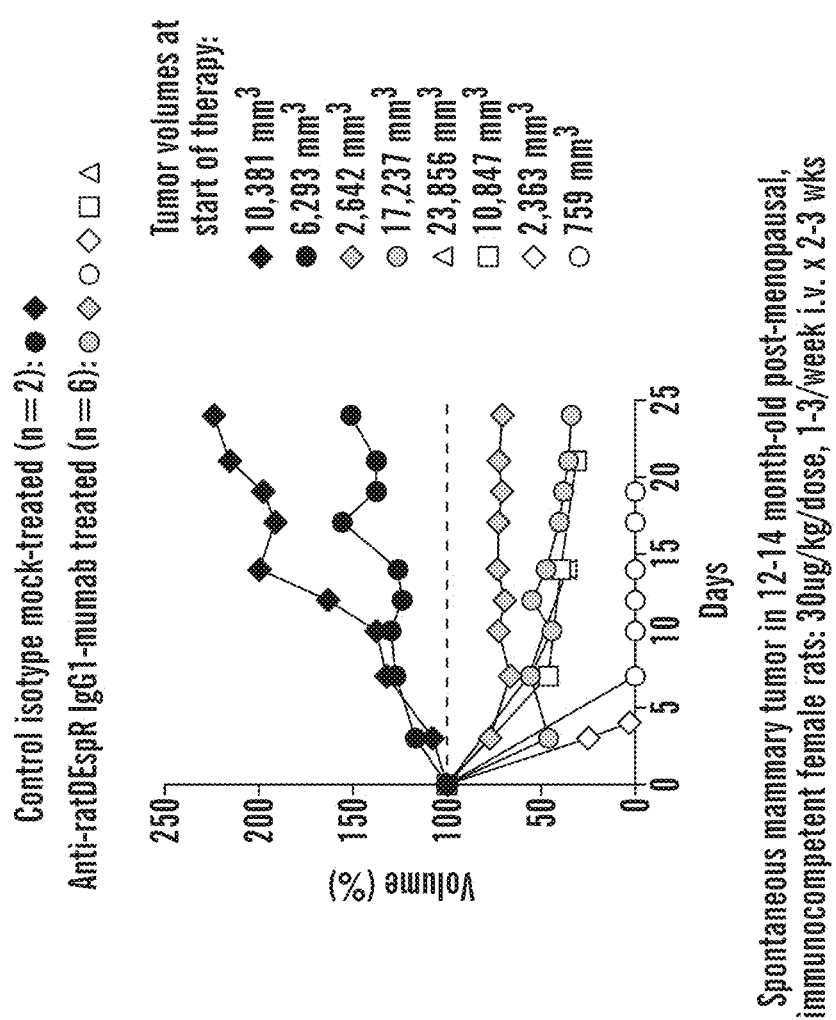
FIG. 16 demonstrates greater tumor regression of spontaneous mammary tumor model in immune competent rats. Anti-DEspR induced greater tumor regression from baseline tumor volumes—ranging from 759 to 23,856 mm$^3$ in volume—in a spontaneous mammary tumor model in immune competent rats. This is consistent with reports that greater tumor regression in immune competent models than in xenograft immune-comprised models is concordant with the anti-tumor roles of the intact immune system in immune-competent tumor models. Consistent with this notion, while anti-DEspR slowed the rate of tumor growth rate significantly in xenograft tumor models in immune-compromised nude rats, anti-DEspR regressed tumor size markedly from baseline tumor volumes in immune competent CSC-derived rat models. These observations suggest that anti-DEspR's inhibitory effects on neutrophil survival eliminate neutrophil-mediated tumor immune-evasion, which then facilitates tumor regression—but only in an immune-competent tumor model. The anti-DEspR mAb had the murine IgG1/kappa Fc region, which has insignificant antibody-dependent cell-mediated cytotoxicity (ADCC) or complement dependent cytotoxicity (CDC), hence ADCC and CDC cannot account for the tumor regression.

Stabilized S228P IgG4 Backbone: Efficacy Based on Receptor Blocking and not on ADCC or CDC Rationale and Mode of Action Overview for Anti-DEspR Combination with Immunotherapy:

COMPLEMENTARY MODE OF ACTION: Anti-DEspR (hu-6g8, or ABT-468) inhibition of CSCs survival/self-renewal, tumor cell invasiveness, angiogenesis collectively lead to decrease in metastasis dissemination and progression cycles, which complements immunotherapy immune-surveillance to eliminate tumor cells. This is seen in the more robust tumor regression by anti-DEspR of spontaneous mammary tumors in immune-competent rats (FIG. 16) compared to inhibition of tumor growth rate but not regression in xenograft pancreatic and glioblastoma tumors.[74]

Anti-DEspR elimination of activated neutrophils (tumor associated neutrophils or TANs and circulating neutrophils) removes neutrophil-mediated inhibition of T-cell activation and proliferation, which continue even in the presence of PD1/PD-L1 inhibitors, hence key mechanisms of immunotherapy resistance. Moreover, activated neutrophils also express PD-L1, hence are capable of inducing apoptosis in T-cells while extending their own survival.

INDUCTION OF CSC AND TUMOR CELL APOPTOSIS ENHANCES EFFICACY OF T-CELL IMMUNE SURVEILLANCE. HU-6G8 decrease of pro-survival proteins (Mcl1, BIRC3) and increase in pro-apoptotic genes, thus inducing apoptosis of activated neutrophils, which then enhances efficacy of T-cell immune surveillance by eliminating neutrophil-mediated T-cell suppression.

STABILIZATION OF TUMOR VASCULATURE FACILITATES DELIVERY of immunotherapy to the tumor, as well as minimizes extravasation of metastatic tumor cells.

Data validate the following therapeutic hypotheses.

Therapeutic hypothesis: Hu-6g8 is a potential partner for PD1/PD-L1 inhibitor (or chemotherapy) combination therapy in advanced stage IV cancers, as anti-DEspR brings novel targeted efficacy and safety advantages that could enhance survival outcomes and potentially lower the dose needed for immunotherapies, so as to reduce the latter's side effects. Projected patient stratifiers: PD-L1+ tumors/DEspR+ tumor associated neutrophils (TANs), tumor cells, CSCs (cancer stem cells or metastasis initiating cells), and/or tumor microvessels.

| Efficacy Profile: in vitro and in vivo preclinical data Tested using anti-DEspR murine mAbs & hu-6g8 | Therapeutic Potential: Efficacy Advantages of hu-6g8 as partner for immunotherapy |
|---|---|
| 1 - targeted inhibition of DEspR+ CSCs inhibits CSC anoikis resistance, survival in adverse metabolic conditions, self-renewal and seeding inhibits self-renewal and seeding | Decreases apoptosis resistance of CSCs = induces apoptosis of CSCs Stops feed-forward dissemination-seeding-progression cycles as tested in pancreatic peritoneal carcinomatosis CSC-derived xenograft (CDX)-tumor model NOTE: tumor cell death obviates tumor cell mutations that lead to immunotherapy resistance |
| 2 - targeted inhibition of DEspR+ CSC-mediated vasculogenic mimicry and tumor angiogenesis Inhibits including VEGF-independent FGF2/EGF-mediated angiogenesis, stops neovessel fragility Stabilizes tumor vasculature | Stops tumor volume increase >1-2 mm in expansive tumor zones Stops tumor cell local invasion along blood vessels [* VEGF resistant tumors] Facilitate delivery of combination therapies |
| 3 - targeted inhibition of DEspR+/CD11b+ activated neutrophils majority of cd11b+ neutrophils are DEspR+ almost all NETs+ neutrophils are DEspR+ anti-DEspR inhibits activated neutrophil 'extended survival' ex vivo, thus obviating NETs+ neutrophils normalizes neutrophil-lymphocyte ratio in CDX-model of pancreatic peritoneal carcinomatosis greater tumor growth regression in spontaneous mammary tumor model in immunocompetent rats, consistent with neutrophil immune-suppression roles observed for chemotherapy | Induction of neutrophil apoptosis obviates: 1] neutrophil pro-metastasis roles (matrix degradation for invasiveness, pro-angiogenesis for microtumor outgrowth) 2] NETosis, hence NETs-mediated pro-metastasis and microthrombi 3] activated neutrophil's multiple roles in T-cell inhibition (such as: a) secretion of PDL-1 (induces T-cell apoptosis), b) release of arginase & ROS (inhibition of T-cell proliferation), c) release of elastase, cathepsin (breakdown of T-cell activating cytokines hence inhibition of T-cell activation]. hu-6g8 induction of neutrophil apoptosis reduces resistance to PD1/PD-L1 inhibitors in non-responsive tumors with high TANs by abrogating activated neutrophils as a source of arginase-1, ROS, elastase and cathepsin G - all of which reduce T-cell anti-tumor functions. |

| Efficacy Profile: in vitro and in vivo preclinical data Tested using anti-DEspR murine mAbs & hu-6g8 | Therapeutic Potential: Efficacy Advantages of hu-6g8 as partner for immunotherapy |
|---|---|
| 4 - targeted inhibition of non-CSC tumor cells inhibits non-CSC tumor cell migration Panc1, MB231 induces apoptosis Panc1 tumor cells | Decreases local invasiveness Induces tumor cell loss in expanding tumor zone NOTE: tumor cell death obviates tumor cell mutations that lead to immunotherapy resistance |
| 5 - DEspR+ expression in multiple cancer types inhibition of tumor growth of pancreatic cancer, glioblastoma, breast cancer, lung cancer, CSC-derived xenograft models increased median overall survival in CDX-pancreatic peritoneal carcinomatosis model with comorbidities better than gemcitabine, in CDX-lung cancer, CDX-colorectal peritoneal carcinomatosis model | Potential efficacy in multiple cancer types Potential to be better than gemcitabine standard of care for stage IV pancreatic cancer Potential to be synergistic with immunotherapy efficacy |

Therapeutic hypothesis. Hu-6g8 is a potential novel adjuvant mono-therapy after surgical resection of primary tumor (potential indications: PDAC, GBM, NSCL, TNBC) or as combination-therapy with PD1/PD-L1 inhibitors approved for adjuvant therapy

| Efficacy Profile: in vitro and in vivo preclinical data Tested using anti-DEspR murine mAbs & hu-6g8 | Therapeutic Potential: Efficacy Advantages of Hu-6g8 as monotherapy or partner for combination for adjuvant Rx |
|---|---|
| 1 - targeted inhibition of DEspR+ CSCs inhibits CSC anoikis resistance, survival in adverse conditions, self-renewal and seeding induces apoptosis | Stop distant dissemination Stop microtumor establishment |
| 2 - inhibits tumor vascularization inhibits CSC-vasculogenesis, inhibits VEGF-independent FGF2/EGF-mediated angiogenesis | Stop microtumor outgrowth > 1-2 mm * VEGF resistant tumors; |
| 3 - inhibits activated neutrophil 'extended survival from constitutive apoptosis' | Stop neutrophil pro-metastasis functions: a) priming for seeding b) pro-angiogenesis for microtumor outgrowth Eliminate neutrophil-mediated immune-evasion Eliminate NETosis-mediated stimulation of tumor cell invasiveness, migration |
| 4 - inhibits non-CSC tumor cell invasiveness induces tumor cell apoptosis, necroptosis | Stop extravasation, seeding Stop microtumor growth |
| 5 - inhibits multiple cancer tissue type seeding PDAC, glioblastoma, NSCLC, TNBC | Potential efficacy in multiple cancer types |

Cumulative safety profile of anti-DEspR mAbs in different preclinical models: safety advantages

| Safety Profile: preclinical observations at doses used (1-10 mg/kg) | Potential safety advantages as partner in combo therapy for advanced cancers or as mono/combo adjuvant therapy |
|---|---|
| 1 - normalizes neutrophil-lymphocyte ratio | NO neutropenia ~ no increased risk for infection |
| 2 - no delay in ulcerated tumor resolution while attaining ulcerated tumor regression in immunocompetent mammary tumor model | Does not impede open ulcer/wound healing |
| 3 - no worsening of co-morbidities in preclinical pancreatic peritoneal carcinomatosis & stroke models | NO side effects that accelerate cancer co-morbidities: ascites, cachexia, gut invasion, gut ischemia |

-continued

| Safety Profile: preclinical observations at doses used (1-10 mg/kg) | Potential safety advantages as partner in combo therapy for advanced cancers or as mono/combo adjuvant therapy |
|---|---|
| 4 - no effects on DEspR(+)kidney tubule epithelial cells | NO proteinuria, no worsening of hypertension |

Figure 9:
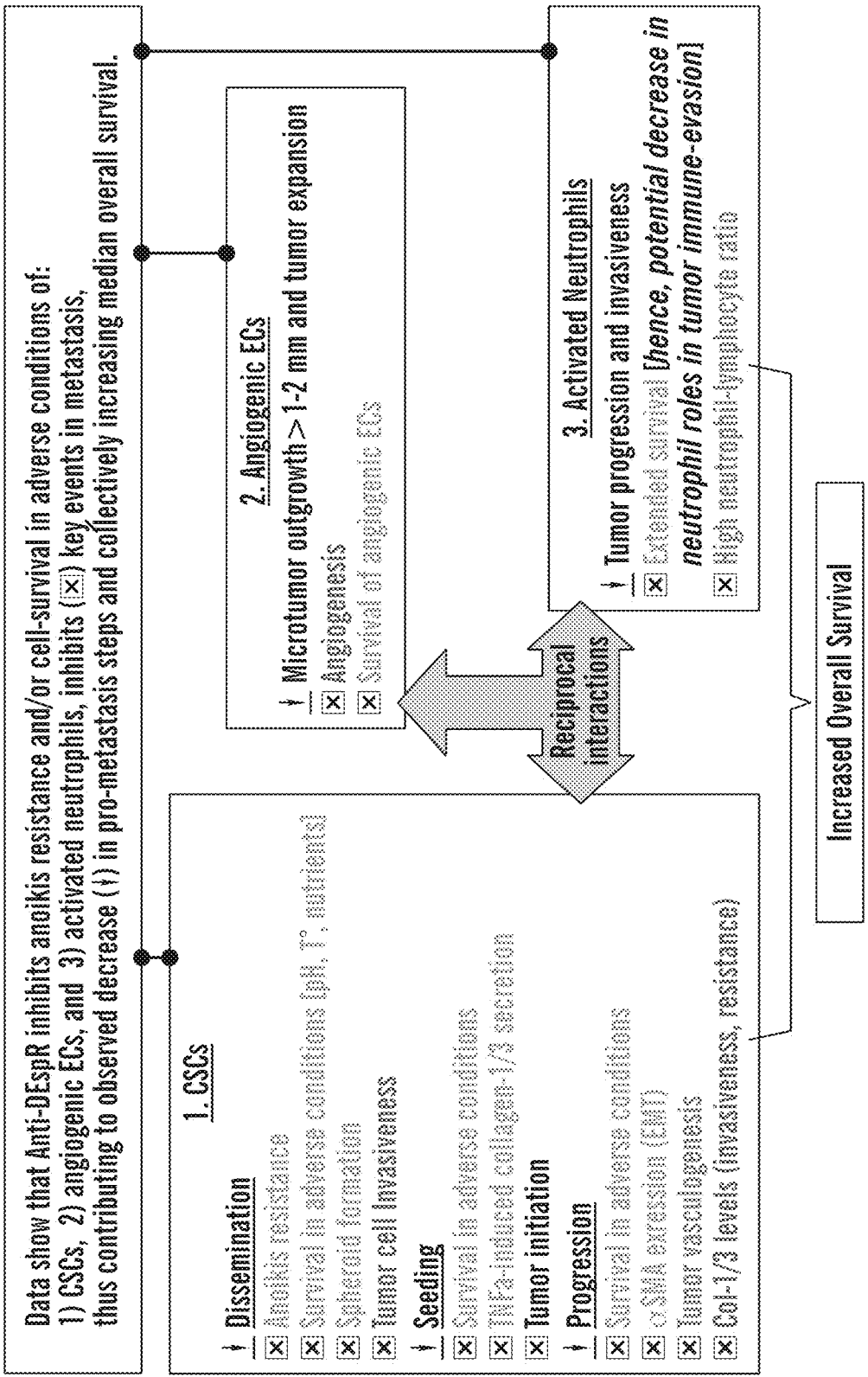
FIG. 9 depicts an overview of MoA in vitro and in vivo supportive data tested in multiple solid tumor experimental models. All in vivo testing were performed in CSC-derived xenograft (CDX) models representing pancreatic cancer, glioblastoma, breast cancer. Col1/3, collagen 1/3; CSCs, cancer stem cells; ECs, endothelial cells; TNFα, tumor necrosis alpha; ↓, decrease in . . . ; ⊠, inhibition by anti-DEspR mAb.

NO observations of life threatening side effects in preclinical models at doses used, as reported for:
a) Keytruda IgG4 (10 mg/kg q 2 wks): infusion reactions, immune-mediated pneumonitis, including fatal cases; immune-mediated hepatitis, nephritis, type-1 diabetes, diabetic ketoacidosis, colitis
b) Opdivo IgG4 (3 mg/kg q 2 wks): ): infusion reactions, immune-mediated pneumonitis and encephalitis - both including fatal cases, pulmonary embolism, pleural effusion, respiratory failure; immune-mediated hepatitis, nephritis, endocrinopathies, colitis; severe inflammatory syndrome, myocarditis
c) chemotherapy: severe neutropenia with risk of infection, impairment of wound healing, anemia
Note:
adjuvant chemotherapy is recommended to be given only after 2 wks past surgery
d) Avastin: stroke, bleeds, thrombosis, gut perforation, hypertensive crisis, hemolytic uremic syndrome, proteinuria
Note:
Avastin is recommended not to be given 28 days prior to surgery or after surgery Cohesive Framework of In Vitro and In Vivo Data Depicting Anti-DEspR's Multi-Faceted MoA—
inhibition of 1] cancer stem-like cells (CSCs), 2] angiogenesis and 3] activated neutrophils and the respective impact(s) on key cancer metastasis hallmarks: tumor dissemination, seeding or initiation, microtumor outgrowth/expansion, tumor progression and invasiveness (FIG. 9).

REFERENCES

Vanneman M, Dranoff G. 2012. Conventional cytotoxic therapies in conjunction with immunotherapies. Nat Rev Cancer 12:237-251.
Leliefeld P H C, Koenderman L, Pillay J. 2015. Frontiers Immunology 14 Sep. 2015. How neutrophils change adaptive immune responses.
Safa A R, 2016. Resistance to cell death and its modulation in cancer stem cells. Crit Rev Oncog 21:203-219.
Park J, et al. 2016. Cancer cells induce metastasis-supporting neutrophil extracellular DNA traps. Science Transl Med 8:361ra138. 19 Oct. 2016.

Example 3

It is demonstrated herein that DEspR is expressed on human activated neutrophils (actPMNs), and also on actPMNs that have undergone NETosis. Anti-DEspR mAb decreases survival of human actPMNs, and by decreasing actPMNs survival prevents actPMN NETosis, hence prevent or abrogate release of NETs.

Normal or quiescent or non-activated PMNs are constitutively apoptotic surviving only from 2-8 hrs (reports of time range vary) but nevertheless it is established that non-activated PMNs survive only for hours in the circulation. Activated neutrophils are able to delay this 'constitutive apoptosis'-hence have increased survival to be able to do their functions—'kill bacteria" via proteases, ROS, myeloperoxidase (MPO), and NETs (neutrophil extracellular traps). However, activated neutrophils functionality (release of proteases, elastases, MPO, NETs can become maladaptive, "the neutrophil paradox"—i.e., what kills bacteria can also cause tissue injury especially with increasing findings of NETs involved in various diseases: e.g., BBB disruption in stroke, matrix degradation and promotion of metastasis in cancer, delay wound healing in diabetes, as well as microthrombi in cancer, sepsis, stroke, systemic lupus erythematosus (SLE), acute respiratory distress syndrome (ARDS), deep vein thrombosis—to name a few.

Anti-DEspR mAb therapy is contemplated herein for diseases wherein activated neutrophils and NETs underlie or worsen pathogenic events. For example, therapies are needed for the following and anti-DEspR can provide that 'breakthrough' therapy that stops or slows actPMN-mediated or NET-mediated pathogenic events. For example, anti-DEspR has the potential to be first-in-class biotherapeutic to:
 a. improve wound healing in diabetics,
 b. reduce neutrophil-associated thrombosis and microthrombi formation and the multi-organ failure that ensues as seen in sepsis, cancer, ARDS, as well as in stroke and acute coronary syndromes.
 c. reduce infiltrating neutrophil burden in the lung in ARDS thus allowing greater success for respiratory support interventions, hence ARDS mortality
 d. reduce stroke (all types) mortality from neutrophil-mediated blood brain barrier disruption which leads to cerebral edema and micro- and macro-hemorrhages as seen in traumatic brain injury, and not just stroke
 e. reduce contribution of circulating neutrophils and tumor-associated neutrophils to immune suppression hence tumor immune-evasion Anti-DEspR mAb can be used as the targeting moiety for diagnostics to detect NET+ microthrombi.
The methods described herein can provide therapy where there is no effective therapy, or improve on current therapies:
 1. improve wound healing in diabetics which is delayed by NETs
 2. reduce BBB disruption hence cerebral edema and microhemorrhages in traumatic brain injury, stroke, anoxic brain injury, brain tumors
 3. attenuate acute lung injury or ARDS and its progression to multi-organ failure 4 attenuate systemic microthrombi and ensuing multi-organ failure in sepsis, end-stage cancer patients (dying from multi-organ failure rather than from the tumor mass per se)
 5. serve as targeting moiety for NETs to deliver nanoparticles with DNAses or histone inhibitors (found to eliminate NETs made up of extruded DNA and histones)
 6. decrease tissue injury mediated by neutrophils in: rheumatoid arthritis, decrease NETs as source of autoantigens from neo-epitopes from citrullinated histones in the NETs Anti-DEspR therapy can reduce the maladaptive activated neutrophil-mediated and/or NETs-mediated pathogenic contributions to different diseases where neutrophils have long-been implicated. Advantages over current therapies can include:

1. safer: Decreasing survival of activated neutrophils without ablating or depleting normal quiescent neutrophils or affecting other leukocytes could provide a safer therapeutic profile.
2. more effective:
   a. Rather than blocking the adhesion of neutrophils (e.g., anti-ICAM mAbs) which will have no effect on neutrophils already transmigrated, and which also further activates neutrophils, anti-DEspR will decrease survival of actPMNs in the circulation and infiltrated PMNs in tissue. Transmigration through the vascular endothelium or epithelium (in the lung) activates neutrophils.
   b. Given the emerging prominence of NETs being implicated in several pathogenic events in different diseases without effective therapy, rather than trying to dismantle NETs which might be "too late" approach, and/or difficult since NETs formation and composition are complex, it is better to decrease the survival of actPMNs so they don't form NETs.
   c. Anti-DEspR will block the effects of endothelin-1 (ET1) which is increased in and associated with poor prognosis in stroke, cancer, heart failure—given that classical ET1 type-a and type-b receptor antagonists have failed in clinical trials for cancer, stroke, heart failure.
3. development of anti-DEspR mAb as a multi-pronged therapy for cancer will also target neutrophil-mediated immune evasion and T-cell suppression underlying therapy resistance, neutrophil-mediated matrix degradation contributing to tumor local invasion and metastasis, as well as, neutrophil-mediated thrombosis in cancer—and hence effectuate increased overall survival, not just from the attenuation of metastasis in a safer way than current chemotherapeutics, but also reduce the cancer-associated thrombosis and systemic microthrombi which lead to multi-organ failure in end-stage cancers. In fact, microthrombi could contribute to the severe pain associated with some cancers, gut ischemia as observed in pancreatic peritoneal metastasis.

Activated neutrophils, and now also NETs, are increasingly being implicated in different pathogenic events wherein tissue injury and multi-organ microthrombi occur. ActPMNs and NETs involvement take a rather 'fulminant' course—i.e., nothing seems to be able to dampen or attenuate once initiated. Anti-adhesion mAb therapies have not worked effectively—which in retrospect might be "too little, too late" scenario. In animal models, neutrophil roles are demonstrated by neutrophil depletion studies. As described herein, we have discovered that DEspR is expressed on activated neutrophils and its inhibition decreases survival of activated neutrophils, which are known to have delayed apoptosis (hence increased survival) in contrast to normal quiescent neutrophils which are DEspR-negative and constitutively apoptotic with lifespan in hours. In particular it is demonstrated herein that anti-DEspR fully humanized antibody on an IgG4/kappa Fc region binds to and inhibits survival of activated neutrophils, hence preventing formation of neutrophil-mediated tissue injury, blood brain barrier (BBB) disruption, angiogenesis and NET formation.

Example 4

Acute lung injury (ALI) and its progression to acute respiratory distress syndrome (ARDS) and multi-organ failure (MOF) occur in 5-10% of ICU admissions globally,[1] with about 200,000 cases per year in the US, 3 and ~175,000 cases in the EU. Regardless of underlying cause,[4] and despite all interventions in intensive care medicine, mortality remains high at ~40%. 2, 5 ARDS-survivors have chronic sequelae and disabilities, even among young survivors.[2,6] Despite extensive research and multiple clinical trials[7], no new therapies have passed Phase 3 trials for ALI/ARDS/MOF, reiterating the high unmet need for novel treatments that can improve survival and/or decrease sequelae[2,8].

Lessons from failed or equivocal results in clinical trials for ARDS teach that pleiotropic endothelial effects of statins (rosuvastatin,[9] simvastatin[10]), bronchodilation by β-agonists (salbutamol),[11] pulmonary vasodilator and improved oxygenation by nitric oxide,[12] non-specific inflammatory gene expression inhibition by glucocorticosteroids,[13,14] have non-effective efficacy/safety profiles as therapy for ALI/ARDS. Mechanistically, regardless of underlying cause, activated neutrophils are central to ALI/ARDS' pathogenesis and progression to MOF.[15] In fact, ARDS in neutropenic patients is also neutrophil-driven since ALI/ARDS is associated with neutrophil recovery[16] or with granulocyte-colony stimulating factor (G-CSF) induction of neutrophil recovery in said neutropenic patients. 17 Knowing that therapeutic efficacy in ALI/ARDS/MOF requires the direct inhibition of the self-amplifying maladaptive neutrophil-mediated tissue injury 18 in ALI/ARDS 19, 20, 21 but with a safety profile that will not worsen underlying sepsis or multiple organ dysfunctions in critically ill patients. A neutrophil-centered approach is supported by preclinical efficacy of total neutrophil depletion in reducing ALI/ARDS in animal models, 22 and can be expected to also attenuate progression to MOF, the major cause of death in ARDS, 23 since activated neutrophils play key roles in MOF 24 through neutrophil-mediated microvascular endothelial injury, capillary permeability, 25 and neutrophil-extracellular trap (NET)-associated microthrombi, 26, 27 endothelial and lung epithelial injury. Not unexpectedly, inhibition of neutrophil elastase was ineffective 28 or at best controversial 29 indicating the importance of eliminating all neutrophil roles in ARDS, and not just one specific protease. On the other hand, a global anti-inflammatory approach is also not effective, since functional macrophages are required for efferocytosis of apoptotic cells towards resolution of the hyper-inflammatory state in ARDS, 30 as supported by in vivo preclinical studies showing that inhibition of macrophage recruitment by anti-MCP1 mAb, 31 and macrophage-depletion 32 worsen ARDS.

As described herein, we have discovered that anti-DEspR inhibits survival of LPS-activated neutrophils ex vivo and increased survival from LPS-induced hemorrhagic encephalopathy in rats. We also found that DEspR is expressed on human activated-neutrophils and NETosing activated-neutrophils. These data support the therapeutic hypothesis that anti-DEspR provides a translatable equivalent to neutrophil depletion, hence abrogating the central pathogenic driver in ALI/ARDS/MOF.

Figure 10:
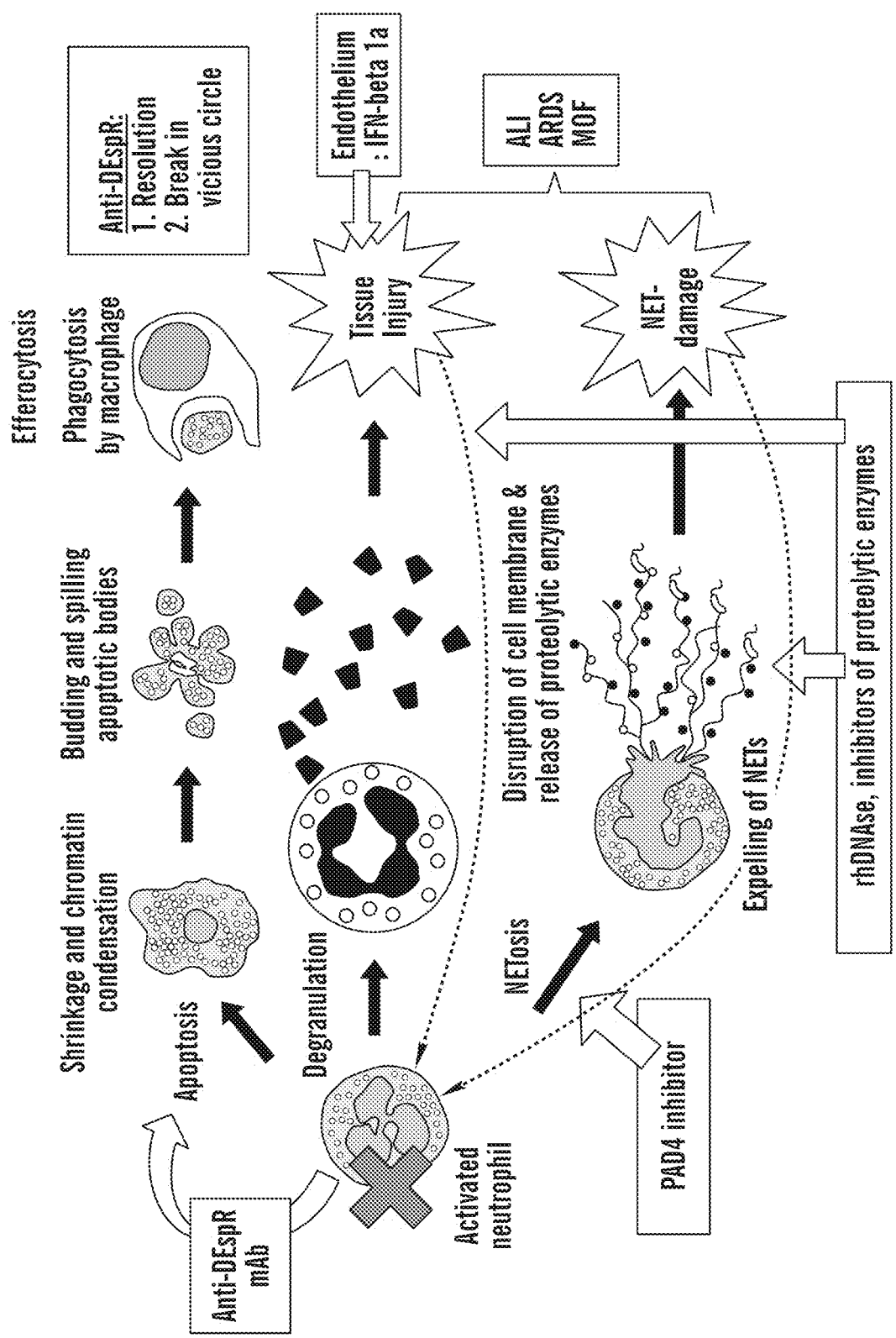
FIG. 10 depicts a diagram. Anti-DEspR mAb breaks the vicious cycles mediated by maladaptive, excessive activated neutrophil activity that lead to tissue injury and NET-damage, and collectively contribute to ALI/ARDS and MOF. Anti-DEspR targets activated neutrophils inducing apoptosis for subsequent efferocytosis towards resolution of the injury cascades and vicious circles in ALI/ARDS. In contrast, other approaches target downstream events or endpoints but do not target the central driver-activated neutrophils.

To translate the therapeutic paradigm of 'neutrophil-depletion' without safety concerns from neutropenia in ARDS patients, described herein is a novel target-specific biotherapeutic, a humanized/deimmunized anti-DEspR monoclonal antibody (mAb) with a hinge-stabilized S228P IgG4 backbone, hu-6g8, that will:

1] abrogate DEspR(+) activated neutrophils and NETs as drivers of ALI-ARDS-MOF progression, thus breaking the vicious circle of neutrophil-mediated injury cascades, but will 2] spare DEspR(−) quiescent neutrophils, monocytes, endothelial cells, and lung epithelial cells, thus attaining an optimal safety profile that tips the balance towards efferocytosis and resolution of the hyper-inflammatory state in ALI/ARDS, once DEspR+ activated neutrophils are inhibited (FIG. 10).

The estimate is 200,000 cases/year of ARDS in the US, 37, 38 and about 175,000 in the EU. ALI/ARDS occurs in multiple disease entities: sepsis, pneumonia, trauma, direct lung injury, and ventilator-induced injury. In a 5-continent 50-center study, the 2014 period prevalence of ARDS was 10.4% of ICU admissions; with hospital mortality of 34.9% (mild), 40.3% (moderate), and 46.1% (severe ARDS). 39

The therapies described herein can be used to treat, e.g.:
1. ALI/ARDS patients in the ICU
2. Neutrophil-exacerbated pulmonary diseases: a) chronic obstructive pulmonary disease (COPD) 40 and b) cystic fibrosis 41 wherein activated neutrophils and NETS are directly involved in bouts of exacerbation. 42
3. Neutrophil-mediated injury cascades: blood brain barrier (BBB) disruption with ensuing vasogenic edema and hemorrhagic complications in a) post-ischemic stroke secondary injury, b) sepsis, c) traumatic brain injury.
4. Neutrophil cell-cell crosstalk that promotes metastasis, therapy resistance, and immune-evasions in cancer patients with: a) pancreatic ductal adenocarcinoma, b) glioblastoma, c) triple negative breast cancer, d) non-small cell lung cancer, e) colorectal cancer, f) melanoma. Preclinical studies support hu-6g8 as potential novel adjuvant or neo-adjuvant therapy to prevent metastasis and microtumor outgrowth, and/or slow tumor progression.

anti-DEspR mAb therapy vs current and predicted standard of care. Current standard of care for ALI/ARDS is limited to lung-protective ventilation and fluid-conservative strategies, and treatment of the underlying cause, but no effective pharmacotherapeutic is available. 43 There is no therapy for ALI/ARDS other than lung-protective ventilation strategy and supportive care. "Despite earlier encouraging preclinical evidence, Phase 3 trials have not supported the use of exogenous surfactant, inhaled nitric oxide, intravenous prostaglandin E1, glucocorticoids, ketoconazole, lisofylline, N-acetylcysteine, and activated protein C as treatments for ALI." 52 More recently, rosuvastatin therapy also did not improve clinical outcomes in patients with sepsis-associated ARDS and may have contributed to hepatic and renal organ dysfunction. 53 Additionally, over a 1-year follow-up of ARDS survivors, rosuvastatin had no effect on chronic sequelae from ARDS/ALI. 54 Similarly, β-blockers did not attenuate ARDS, and instead may have contributed to worse outcomes.[55] These cumulative failures highlight the need for novel therapies.

Patients with ALI or ARDS require intensive critical care, mechanical ventilation and are at high risk for MOF and death. They have substantial health care costs, and those that survive have persistent, profound disability[45] and lower health-related quality of life.[46] There is no effective therapy for ALI/ARDS, nor the other diseases (stroke, traumatic brain injury, acute kidney injury, etc) that are exacerbated by neutrophil-driven secondary tissue injury.

In one embodiment, described herein is a pan-species reactive humanized-deimmunized anti-DEspR IgG4 mAb, hu-6g8, which exhibits a balanced efficacy-safety-temporal activity profiles required for critical care setting pharmacotherapy. FIG. 10 illustrates the hu-6g8 mode of action: it eliminates activated neutrophils by inducing apoptosis for subsequent efferocytosis and resolution. This MoA decreases multiple mechanisms of neutrophil-mediated tissue injury in ARDS/multi-organ failure (MOF) or multi-organ dysfunction syndrome: neutrophil release of proteases that disrupt endothelial and alveolar cell membranes, and NETosis-mediated alveolar and endothelial damage, and microthrombo-angiopathy seen in ARDS progression to MOF.

Briefly, this anti-DEspR approach is supported by experimental data as outlined below:
1. Validation of DEspR as target. DEspR is expressed on activated human neutrophils (FIG. 1A,1C,1D). Anti-DEspR immunostaining specificity is shown by no signal in isotype control neutrophils (FIG. 1B). Most human neutrophils undergoing NETosis are DEspR+ (FIG. 1C-1D). NETs (neutrophil extracellular traps) are associated with organ microthrombi in MOF and directly induce endothelial and epithelial cell death,[56] all of which are pathogenic events in ARDS.
2. In non-survivor ARDS patients and in LPS-induced human neutrophils, the majority of CD11b+ activated neutrophils are DEspR+, in contrast to CD11b(−) neutrophils which are predominantly DEspR(−) (FIG. 2A). Treatment with two anti-DEspR mabs [anti-ratDEspR-10a3, and pan-species reactive anti-DEspRHuman/Rat/Monkey mAb, 6g8, decreased survival of LPS-activated neutrophils in contrast to control non-treated human and rat neutrophils (P<0.0001) (FIG. 2B).

Figure 11:
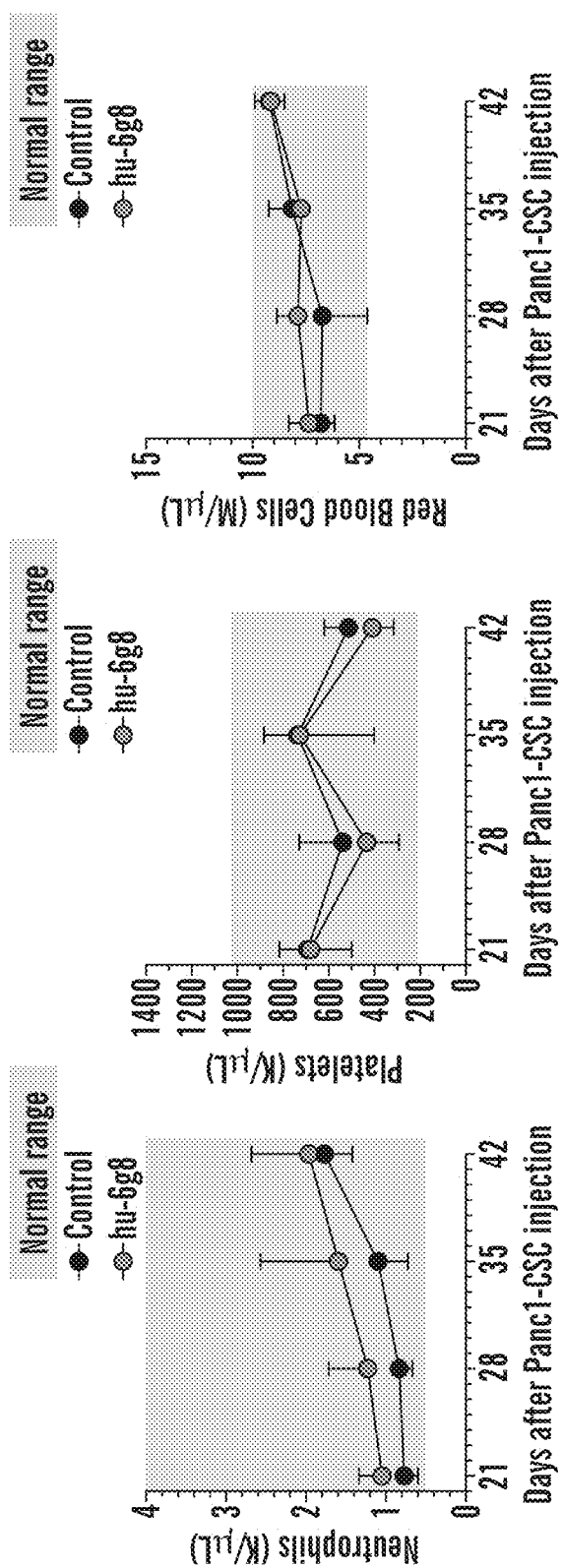
FIG. 11 depicts graphs demonstrating that humanized anti-DEspR mAb, hu-6g8 does not cause decreased numbers of quiescent neutrophils as they are DEspR(−), i.e., no neutropenia side effect. Anti-DEspR hu-6g8 also does not cause decreased platelet counts or red blood cell counts compared to non-treated controls. Complete blood counts (CBC) were measured weekly starting day 21-1 week after treatment onset on day 14 (14 days after Panc1-CSC xenograft (CDX) tumor establishment).

These data support the mechanism of action deduced from several independent experimental systems: neutrophils, kidney and endothelial cells, cancer stem cells. Quiescent neutrophils (majority DEspR-negative) are constitutively apoptotic with short circulating lifespans (e.g., 4-8 hours). Activated neutrophils (majority DEspR-positive) have extended lifespans—or increased survival and delayed apoptosis. Neutrophils that have infiltrated tissues or tumors are activated; neutrophil transmigration from the blood vessel into tissues activates neutrophils. The majority (98%) of CD11b(−) quiescent neutrophils (FIG. 2A, Q4) are DEspR(−), indicating that anti-DEspR treatment will not cause neutropenia. This is shown in vivo in multiple dose treatments in a tumor model (FIG. 11), as well as in a single-dose treated stroke model.

The murine precursor anti-DEspR antibody, 6g8-mumab, was studied in a rat model of LPS-induced hemorrhagic encephalopathy as a paradigm of multi-organ failure (MOF) in ARDS and sepsis (FIG. 3A-3F). Compared to a normal rat brain (FIG. 3A) or a LPS-treated brain not treated with 6g8-mumab (FIG. 3B), a single dose of anti-DEspR mAb (1 mg/kg/dose iv) attenuated the progression to life-threatening hemorrhagic encephalopathy (FIG. 3C). Target engagement is shown by detection of anti-DEspR murine IgG in the brain of treated rats (FIG. 3D).

Concordantly, decreased functional activity of activated neutrophils is shown by decreased myeloperoxidase levels in the 6g8 mumab-treated rat brains (FIG. 3E). To further confirm in vivo efficacy in abrogating neutrophils, a decrease in brain albumin content indicating a decrease in brain edema was analyzed and detected (FIG. 3F), indicating that the blood brain barrier was stabilized by the anti-DEspR treatment. Although vascular-tissue barriers are anatomically distinct, commonalties in neutrophil-mediated injury of the blood brain barrier and alveolar-capillary barrier—i.e., both exhibiting edema, tissue injury, hemorrhages—speak to the neutrophil's key driver role in 'vascular-tissue barrier injury' regardless of organ and cause.

It was also determined whether anti-DEspR can increase survival of rats in a LPS-induced hemorrhagic encephalopathy MOF rat model. Briefly, anti-DEspR mAb treatment increased survival in 5/8 rats treated, with 50% (4/8) of the treated rats regaining normal activity and health at end of study (median >30 d; study stopped on day-33, vs 16 hrs for untreated), Survival Analysis p=0.0007 (FIG. 4).

Figure 12:
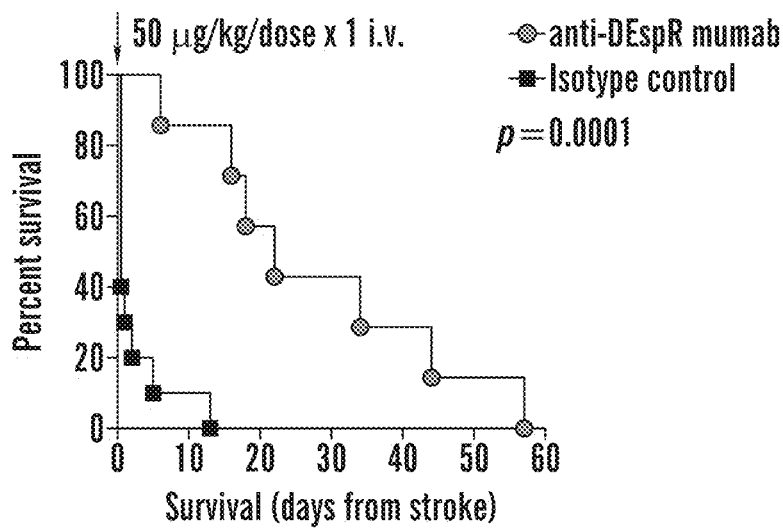
FIG. 12 depicts a graph demonstrating that a single dose of anti-DEspR mumab given at acute stroke onset increased survival in stroke prone transgenic hyperlipidemia/hypertensive (spTg25) rats. Anti-DEspR given intravenously (i.v.) via tail vein i.v., isotype control, murine IgG1 (with insignificant to no antibody-dependent cell-mediated cytotoxicity or ADCC, and complement-dependent cytotoxicity or CDC). Stroke symptoms were documented for at least 1 hour to rule out transient ischemia. Stroke onset was identified as done clinically, by the presence of neurologic signs of stroke: seizures, paresis, paralysis, decorticate posturing, athetoid movements. Rats were monitored for survival (death or a 2nd stroke followed by euthanasia). Kaplan Meier Survival Curve analysis, log rank Mantel-Cox P<0.0001, median survival: 0.5 days for non-treated, 22 days for anti-DEspR treated; hazard ratio for death was 17.8 for non-treated stroke rats with 95% CI 4.2 to 75.5.

Furthermore, these observations are corroborated by in vivo stroke model data showing that a single anti-DEspR mAb dose infused in the acute stroke stage increases survival from acute stroke-deaths and resolves neurologic deficits (seizures, paresis, loss of consciousness), most likely due to reduction of post-ischemic neutrophil-mediated blood brain barrier (BBB) disruption, vasogenic edema and hemorrhagic complications (FIG. 12). Given that neutrophil-mediated BBB disruption, edema and hemorrhagic complications parallel neutrophil-mediated alveolar-capillary barrier breakdown, edema and hemorrhages in ALI/ARDS,[63] anti-DEspR mAb efficacy in decreasing neutrophil-mediated injury in the post-ischemic stroke period supports the effectiveness of anti-DEsprR therapies in neutrophil-mediated ALI/ARDS.

Described herein is the development, characterization, and validation of a fully humanized anti-DEspR mAb with a S228P hinge-stabilized IgG4/kappa FC region, designated herein as hu-6g8 or ABT-468. The hu-6g8 was designed for high binding affinity to DEspR+ human cells and inhibition of activated neutrophil survival. hu-6g8 is reactive in all species, having identical epitopes in human, primates and rodents, which facilitates preclinical and clinical studies using the therapeutic lead. Compared to its murine precursor 6g8-mumab, in vitro analysis demonstrates greater binding affinity of hu-6g8 [EC50<5 nM] and dose-dependent inhibition of neutrophil survival [IC50<8 nM] (FIG. 6). Through recombinant DNA technology, hu-6g8 was designed with optimal biophysical properties via: a) avoidance of T-cell epitopes for low immunogenicity—'deimmunized', b) optimization of heavy and light chain interactions for stability of variable domains, and c) exclusion of destabilizing post-translational modification sites [deamidation, oxidation, acid-lability, inappropriate N-glycosylation, isomerization and pyroglutamate formation].

While there is no FDA-approved pharmacotherapeutic for ALI/ARDS/MOF, hu-6g8 has inherent advantages compared to therapies that failed in Phase 3 or currently in Phase 3 (FP-1201).

1] Efficacy advantages:
  a) In contrast to FP-1201 in Phase 3, and past candidates that failed in Phase 3 trials, hu-6g8 targets the central driver in ALI/ARDS/MOF, the activated neutrophil, by dually decreasing survival and increasing apoptosis of activated neutrophils, but without inhibiting DEspR(−) monocytes/macrophages, which are required for efferocytosis (or clearance) of apoptotic neutrophils without release of harmful neutrophil proteases. Anti-DEspR hu-6g8 translates the therapeutic paradigm of neutrophil-depletion that prevented ARDS, and abides by the lesson taught by macrophage depletion which worsened ARDS.
  b) Additionally, in contrast to FP-1201 and failed candidates, elimination of activated neutrophils by hu6g8 can decrease NETs a priori (as NETs derive from actPMNs), which then attenuates NET-mediated alveolar and capillary injury in ARDS, and micro-thrombi formation directly relevant to ARDS-MOF.

Figure 13:
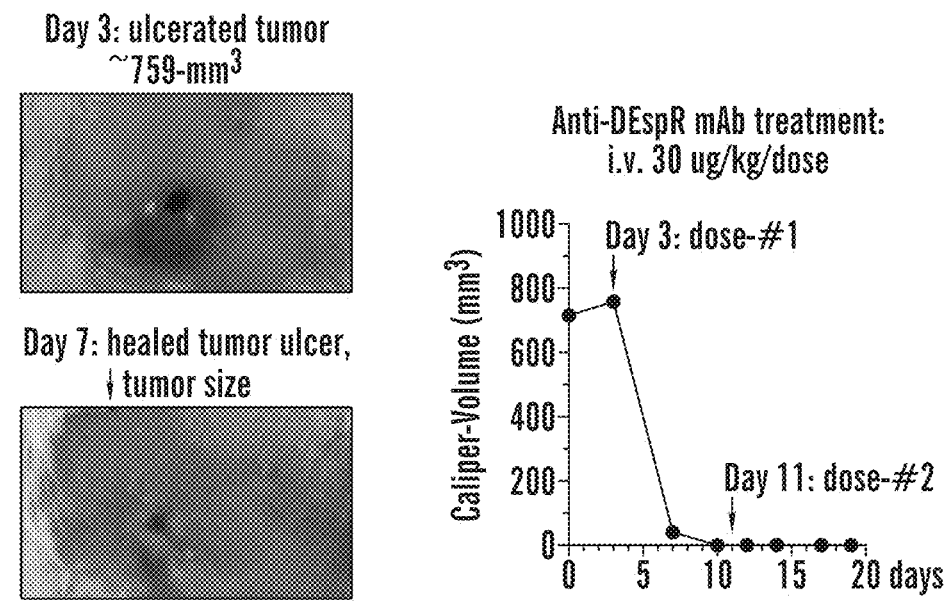
FIG. 13 demonstrates that when tested in an immune-competent spontaneous mammary tumor model, anti-DEspR regressed tumor size without impairing wound healing of an ulcerated tumor. The ulcerated tumor documented for 3 days as non-healing prior to treatment, showed significant improvement 4 days after treatment on day 7. The red indurated tumor area surrounding the central eroded ulcer is due to neutrophil inflammatory infiltrates. Quick resolution by day 7 is concordant with anti-DEspR induction of apoptosis in activated neutrophils for phagocytosis by macrophages and eventual resolution of inflammatory redness and swelling.
Figure 14:
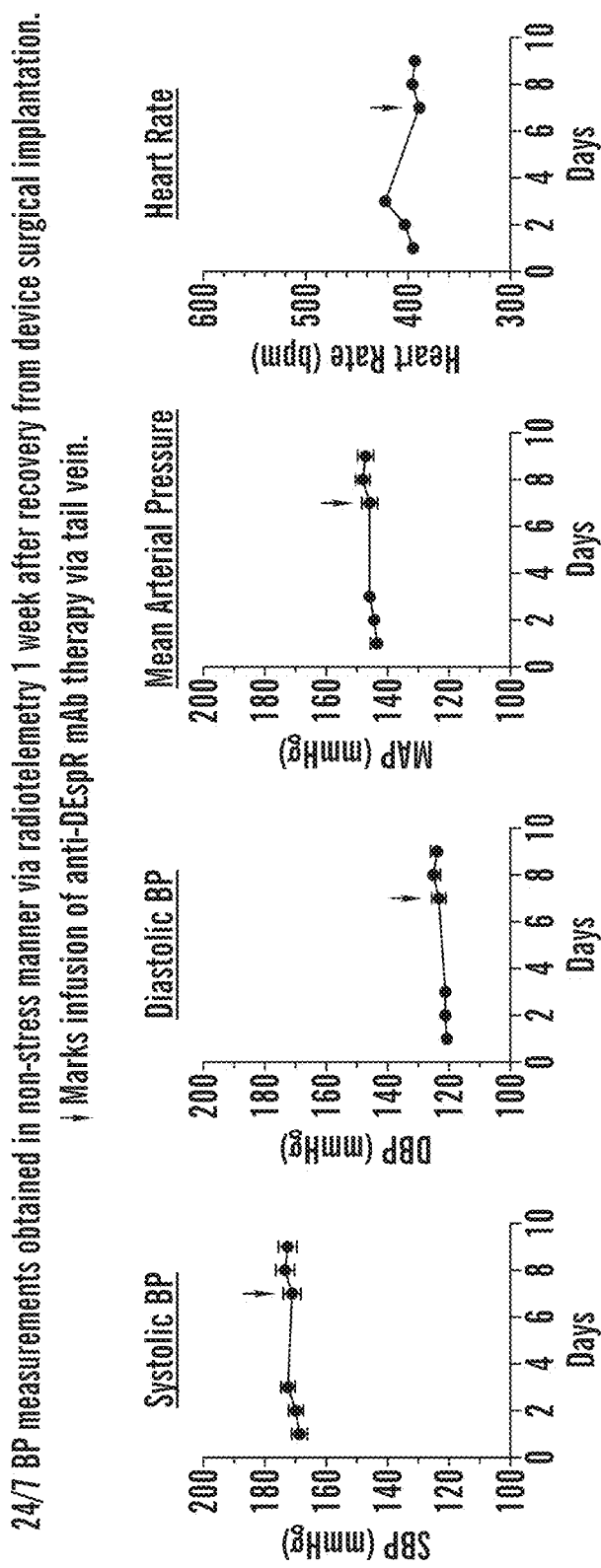
FIG. 14 demonstrates that anti-DEspR mAb does not worsen hypertension or induce hypertensive crisis in salt-sensitive hypertensive rats. Blood pressure (BP) measurements were done using radiotelemetry in order to be able to measure in a non-stress manner, 24/7. After 3 days of baseline recording, anti-DEspR was infused via tail vein, and BP measurements obtained.

2] Safety advantages: In the critical care setting, safety profiles take on equal importance to efficacy. Based on our observation of >65 rats with different xenograft or spontaneous tumors, and >20 stroke-prone hypertensive rats, the following speak to a promising safety profile of anti-DEspR therapy.
  a) Anti-DEspR mAb therapy does not increase risk for infections or impair wound healing at doses used (FIG. 13), in contrast to glucocorticoids which increase risk for infections[68] and impair wound healing.
  b) Anti-DEspR does not cause neutropenia, anemia or thrombocytopenia (FIG. 11).
  c) Anti-DEspR does not aggravate compromised kidney function (FIG. 5) or worsen hypertension (FIG. 14).

It is described herein that hu-6g8 reduces survival and increases apoptosis of DEspR-positive (+) activated neutrophils from ALI and ARDS patients, and that elimination of DEspR+ neutrophils significantly decreases NETosis since most NET+ neutrophils are DEspR+.

Due to the lack of a "gold standard" animal model of ARDS that recapitulates human ARDS in totality with progression to MOF, and due to failure in Phase III trials despite earlier Phase II successful indicators, described herein is ex vivo analysis of anti-DEspR treatment effects on human neutrophils obtained from ARDS-patient blood samples pegged to patient-specific levels of biomarkers associated with ARDS progression or severity.

Characterization of patient sample responders by ARDS biomarkers and DEspR-mechanism relevant biomarkers provides key insight into optimal stratification of ALI/ARDS patients for clinical trials. Moreover, due to the rapidly progressing course of ALI/ARDS/MOF, and likely different stages of progression upon patient sampling, baseline patient characteristics at point of sampling comprised of: clinical parameters of ARDS severity (PaO2/FiO2 or 02 saturation), key ARDS biomarker that modulates neutrophils (IL-6), potential biomarker of NET-mediated MOF (citH3), and DEspR mechanism-relevant biomarker (neutrophil-lymphocyte ratio or NLR, DEspR+/CD11b+ neutrophils) can be characterized.

Optimization of ex vivo assays can maximize the multi-testing of a) hu-6g8 efficacy ex vivo in patient samples, b) ARDS biomarkers associated with hu-6g8 responders, and c) DEspR expression on activated neutrophils with ARDS clinical outcomes. Optimization tests 1) hu-6g8 dose, either 3× or 10× IC50 for inhibiting activated neutrophil survival, and 2) treatment duration—either 6 hrs (validated in rat neutrophil assays (FIG. 2B), or 3 hrs based on hu-6g8 effect on Panc1-tumor cells by 2 hours (FIG. 15).

Normal human volunteer neutrophils can be activated by high dose 10 µg/ml LPS×30 minutes in whole blood, then treated with hu-6g8 (3× or 10×IC50 for neutrophil survival inhibition) or vehicle for 3 hrs or 6 hrs at 37° C. in CO2 incubator. Analysis of efficacy can be done by FACS parameters for live/dead cells and NETosis. Study of potential toxicity—hemolysis will be done by analysis of plasma free Hgb to assess.

% apoptotic (Annexin V-FITC) and % dead (propidium iodide) CD11b+ activated neutrophils can be measured by triple-stained FACs analysis. hu-6g8 efficacy is defined as greater % apoptotic and/or dead neutrophils among CD11b+ activated neutrophils vs non-treated NHV CD11b+ neutrophils.

The % decrease in NETosis in hu-6g8 treated, LPS-activated NHV neutrophils compared to vehicle-treated person-matched controls can be performed via validated FACS measurement of NETs in whole blood as described: DAPI to detect extruded DNA, citH3 to stain extruded citrullinated histone-3, and CD11b to label activated neutrophils. Optimal assay conditions can be defined as the conditions that give the greatest % difference in both parameters [% survival, % NET+] of hu-6g8 efficacy.

In a pilot group of 30 ALI/ARDs patients, the cohort-size of ALI/ARDS patients that have DEspR+/CD11b+ neutrophils and the clinical significance of DEspR+/CD11b+ neutrophils to quantitative measures of ARDS severity: hypoxemia, degree of NETosis, number of ventilator days, and survival (in days) up to 28 days can be determined. The clinical impact of targeting DEspR in ARDS can be reflected in the % of ALI/ARDS patients with DEspR+ activated neutrophils, and the correlation of DEspR+ expression with measures of ARDS severity.

24-30 ARDS patients can be identified according to the Berlin ARDS algorithm, obtain fresh blood sample [7 mls in two tubes (1st 2 ml+2nd: 5 ml), EDTA-anti-coagulant, and collect pertinent clinical demographics and course 3a-1: Criteria for identification of ARDS patients: a) Acute illness; b) Mechanically ventilated with PEEP=5 cm H2O or more; c) bilateral infiltrates on chest film; d) If arterial blood gas (ABG) determined, PaO2/FiO2<300 or if no ABG, and 02 saturation <97%, then Sat %/FiO2<315; e) No heart failure. f) age >18 yrs. Exclusion criteria can include [matched to ongoing phase III trials for FP-1201 or recombinant human IFNβ1a]:
- a) Infections requiring BL-3 or BL-4 biosafety levels. b) Patients with prior liver, kidney, heart failure. c) underlying disease wherein patient will likely not come off ventilator (motor neuron disease, muscular dystrophy, etc), d) COPD with long term home oxygen or ventilator therapy; e) pregnant woman, f) patient is part of another pharmacotherapy protocol.

Patient characteristics of ALI/ARDS patients that correlate with % DEspR+/CD11b+ neutrophils can be assessed. Clinical information obtained can include: a) PaO2/FiO2 or oxygen saturation at diagnosis and on day of blood sample (<48 hrs from diagnosis), b) number of ventilator days, c) underlying diagnosis, d) age, e) sex, f) CBC at diagnosis and day of blood sampling; g) survival within 28 days from ALI/ARDS diagnosis. Biomarker information obtained can include: a) neutrophil-lymphocyte ratio (from CBC), b) % DEspR+ activated CD11b+ neutrophils, % DEspR(−) CD14 monocytes (FACS analysis: DEspR, CD11b, CD14), c) plasma levels of ARDS biomarker IL-6, and NETosis biomarker: citH3.

Analysis of clinical significance of DESPR IN ALI/ARDS can be assessed by determining:
  How many ALI/ARDS patients have elevated DEspR+ activated neutrophils?
  Does % DEspR+ activated neutrophils correlate with baseline NETosis marker, citH3 levels in ARDS patients, and/or ARDS-severity biomarker IL-6 and/or NLR?
  Does % DEspR+/CD11b+ neutrophils correlate with ARDS clinical severity measured as level of hypoxemia (PaO2/FiO2), severity (number of survival days and ventilator days from blood sampling.)
Spearman rank correlation (n=30) can be performed comparing % DEspR+CD11b+ neutrophils vs the different biomarkers associated with worse prognosis (IL-6, NET citH3, NLR) and vs ARDS patient characteristics obtained on day of sampling (PaO2/FiO2; number of ventilator days and survival days. Studying 30 patients provides sufficient power 0.8 for Spearman correlation coefficient r=0.5 with significance 0.05. A correlation coefficient of 0.5 indicates a large effect, 0.3 medium, 0.1 small.

Ex vivo efficacy of hu-6g8 in decreasing activated neutrophil survival and NET formation can be tested using the optimal test dose and duration of treatment described above herein, while also characterizing hu-6g8 responders for ARDS biomarkers and clinical features of severity, and risk for hemolysis. Testing of 10 ARDS patient samples for hu-6g8 efficacy in reducing survival of DEspR+/CD11b+ neutrophils can corroborate anti-DEspR efficacy observed in rat model experiments.

Efficacy in reducing survival Triple immunostaining FACS analysis can be performed (CD11b to mark activated neutrophils), Annexin-V to mark apoptosis, propidium iodide to mark dead cells) to assess whether hu-6g8 decreases survival of CD11b+ neutrophils and inducing apoptosis (Annexin V) or necroptosis (Propidium iodide). Efficacy in reducing netosis: Triple staining FACS analysis can be performed to detect NET+ neutrophils by triple-stained NET components: extruded DNA (DAPI) with bound citrullinated histone 3 (hitC3) and neutrophil-myeloperoxidase (MPO). Neutrophils can be gated by forward scatter or FSC (size) and side scatter or SSC (granularity), distinguishing them from monocytes, thus permitting concomitant analysis of circulating monocytes. Analysis of efficacy can be done by testing whether differences in CD11b+ neutrophils live/dead cell counts and NETs levels between treated vs non-treated samples (n=10/group) are significant by two-tailed t-test, P<0.05. Power calculation delineates sufficient power 0.85, alpha=0.05, for n=10/group with mean-1 at 20 and mean-2 at 40, ~common sd 15. A difference in NETosis, and not just a difference in decreased survival of activated neutrophils indicates efficacy of hu-6g8 as ARDS therapy and prevention of MOF.

To rule-out potential hemolysis side effect of hu-6g8 induced increased neutrophil apoptosis ex vivo given the hyper-inflammatory state in ARDS, the potential toxicity in the context of ARDS hyperinflammatory states can be assessed by determining if any hemolysis inadvertently occurs from complement activation triggered by increased apoptotic cells. Neutrophil apoptosis triggers complement activation without lysis and which markedly increases efficiency of macrophage efferocytosis of apoptotic neutrophils towards resolution of inflammation. Analysis of hemolysis can be done quantitatively by ELISA detection of plasma free hemoglobin (PFHgb) which normally is not present in plasma, PFHgb>50 μg/dl as described and validated.

Analysis of hu-6g8 responder profiles—aside from DESpR+/cd11b+ neutrophils. The potential clinical impact of hu-6g8 can be supported by ex vivo demonstration of hu-6g8 efficacy without hemolysis in neutrophils obtained from ARDS patients that progressed to MOF and/or death. It can also be tested whether there are potential inhibitors of DEspR responsiveness. This will be tested by Spearman rank correlation of % DEspR response (either surviva or NETosis) and % DEspR+cd11b+ neutrophils. A strong correlation indicates no confounders of response—i.e., if DEspR+, then expect a response commensurate to the % DEspR expression. The non-correlation indicates that there are potential confounders in the blood that inhibit efficacy of hu-6g8 despite DEspR+cd11b+ neutrophils.

To strengthen the rationale for anti-DEspR therapy in ALI/ARDS/MOF, hu-6g8 efficacy in reducing activated neutrophil survival in BAL fluid can be tested, e.g., in preparation for testing efficacy of aerosolized delivery of hu-6g8, which can increase effectiveness and/or expand potential applications. These studies can also elucidate the optimal route of administration or basis for dual administration routes—intravenously and aerosolized. Additionally, testing hu-6g8 at different stages of ALI/ARDS using the patient as his/her own control can strengthen the rationale for hu-6g8 therapy in ARDS, and give insight into the therapeutic window.

In can be determined whether hu-6g8 internalizes into neutrophils (as it does in cancer cells) and induces apoptosis, and that hu-6g8-bound circulating neutrophils do not cause endothelial injury or alveolar epithelial cell injury. Additionally, to affirm the hypothesis, the impact of hu-6g8 treatment on activated neutrophil levels of pro-survival proteins (e.g., Mcl1, BIRC3) and pro-apoptotic proteins (e.g., Apaf1) can be tested by comparing treated and untreated neutrophils. Anti-DEspR decreased Mcl1, BIRC3, and increased Apaf1 in pancreatic cancer stem cells.[74]

REFERENCES

1 Bellani G, et al. 2016. Epidemiology, patterns of care, and mortality for patients with acute respiratory distress syndrome in intensive care units in 50 countries. JAMA 315:788-800.

2 Walkey A J, et al., 2012. Acute respiratory distress syndrome: epidemiology and management approaches.

3 Johnson E R, Matthay M A. 2010. Acute lung injury: epidemiology, pathogenesis, and treatment. J Aerosol Med Pulm Drug Delivery 23:243-252.

4 Ware L B. 2006. Pathophysiology of acute lung injury and the acute respiratory distress syndrome. Semin Respir Crit Care Med 27:337-349.

5 Ware L B, Matthay M A. 2000. The acute respiratory distress syndrome. N Engl J Med 342:1334-1349.

6 Walkey A J, et al., 2012. Acute respiratory distress syndrome: epidemiology and management approaches.

7 Johnson E R, Matthay M A. 2010. J Aerosol Med Pulm Drug Delivery 23:243-252.

8 Gattinoni L, et al. 2010. Ventilator-induced lung injury: the anatomical and physiological framework. Crit Care Med 38:S539-548.

9 NHLBI ARDS clinical trials network, et al. 2014. Rosuvastatin for sepsis-ssociated acute respiratory distress syndrome. N Engl J Med 370:2191-2200.

10 McAuley D E, et al. 2014. Simvastatin in the acute respiratory distress syndrome. N Engl J Med 371:1695-1703.

11 Gates S, et al. 2013. Beta-agonist lung injury trial-2 (PALtI-2): a multicenter, randomized, double-blind, placebo-controlled trial and economic evaluation of intravenous infusion of salbutamol versus placebo in patients with acute respiratory distress syndrome. Health Technol Assess 17:v-vi, 1-87.

12 Taylor R W, et al. 2004. Low-dose inhaled nitric oxide inpatients with acute lung injury: a randomized controlled trial. JAMA 291:1603-1609.

13 Steinberg K P, et al 2006. Efficacy and safety of corticosteroids for persistent acute respiratory distress syndrome. N Engl J Med 354:1671-1684.

14 Tongyoo S, et al 2016. Hydrocortisone treatment in early sepsis-associated acute respiratory distress syndrome: results of a randomized controlled trial. Crit Care 20:329.

15 Grommes J, Soehnlein O. 2011. Contribution of neutrophils to acute lung injury. Mol Med 17:293-307.

16 Azoula E, Darmon M. 2010. Acute respiratory distress syndrome during neutropenia recovery. Crit Care 14:114.

17 Karlin L et a. 2005. Respiratory status deterioration during G-CSF-induced neutropenia recovery. Bone Marrow Transplant 36:245-250.

18 Gompertz, S., and R. A. Stockley. 2000. Inflammation-role of the neutrophil and the eosinophil. Semin. Respir. Infect. 15:14-23.

19 Grommes J, Soehnlein O. 2011. Contribution of neutrophils to acute lung injury. Mol Med 17:293-307.

20 Cheng O Z, Paaniyar N. 2013. NET balancing: a problem in inflammatory lung diseases. Front Immunol 4:1.

21 Mitsios A et al. 2017. NETopathies? Unraveling the dark side of old ideas through neutrophils. Front Immunol 7: Article 678.

22 Abraham E, et al. Neutrophils as early immunologic effectors in hemorrhage- or endotoxemia-induced acute lung injury. Am J Physiol Lung Cell Mol Physiol. 2000 December; 279(6):L1137-45.

23 Del Sorbo L, Slutsky A S. 2011. ARDS and multi-organ failure. Curr Opin Crit Care 17:1-6.

24 Brown K A, et al. 2006. Neutrophils in development of multiple organ failure in sepsis. Lancet 368:157-169.

25 Opal S M. 2011. Immunologic alterations and the pathogenesis of organ failure in the ICU. Semin Resp Crit Care Med 32:569-580.

26 Xu J et al. 2009. Extracellular histones are major mediators of death in sepsis. Nat Med 15:1318-1321.

27 Yang H, et al. 2016. New insights into neutrophil extracellular traps: mechanisms of formation and role in inflammation. Front Immunol 7:302.

28 Zeiher B G, et al. 2004. Neutrophil elastase inhibition in acute lung injury: results of the STRIVE study. Crit Care Med 32:1696-1702.

29 Iwata K, et al. 2010. Effect of neutrophil elastase inhibitor (sivelestat sodium) in the treatment of acute lung injury (ALI) and acute respiratory distress syndrome (ARDS): a systematic review and meta-analysis. Intern Med. 2010; 49(22):2423-32.

30 El Kebir, Filep J G. 2013. Targeting neutrophil apoptosis for enhancing the resolution of inflammation. Cells 3:330-348.

31 Nasaraju T, et al. 2010. MCP-1 antibody treatment enhances damage and impedes repair of the alveolar epithelium in influenza. Am J Respir Mol Biol 42:732-743.

32 Nasaraju T, et al. 2011. Excessive neutrophils and neutrophil extracellular traps contribute to acute lung injury in influenza pneumonitis. Am J Pathol 179: 199-210.

33 Ruiz-Opazo N, et al. 1998. Molecular characterization of a dual Endothelin-1/Angiotensin II Receptor. *Molecular Medicine* 4:96-108.

34 Herrera V L, et al. 2005. Embryonic lethality in Dear gene deficient mice: new player in angiogenesis. *Physiol Genomics* 23: 257-268. 15

35 Herrera V L, et al. 2014. DEspR roles in tumor vasculo-angiogenesis, invasiveness, CSC-survival and anoikis resistance: a ‘common receptor coordinator’ paradigm. PLoS ONE 9(1): e85821.

36 Herrera V L, et al. 2016. Confirmation of translatability functionality certifies the dual endothelin1/VEGFsp receptor (DEspR) protein. BMC Molecular Biology 201617:15. DOI: 10.1186/s12867-016-0066-8.

37 Johnson E R, Matthay M A. 2010. Acute lung injury: epidemiology, pathogenesis, and treatment. J Aerosol Med Pulm Drug Delivery 23:243-252.

38 Rubenfeld G D et al. 2005. Incidence and outcomes of acute lung injury. N Engl J Med 20:1685-1690.

39 Bellani G, et al. 2016. Epidemiology, patterns of care, and mortality for patients with acute respiratory distress syndrome in intensive care units in 50 countries. JAMA 315:788-800.

40 Hoenderdos K, Condliffe A. 2013. The neutrophil in chronic obstructive pulmonary disease. Am J Respir Cell Mol Biol 48:531-539.

41 Mitsios A, et al. 2017. NETopathies? Unraveling the dark side of old ideas through neutrophils. Front Immunol 7: Article 678.

41 Abraham E, et al. Neutrophils as early immunologic effectors in hemorrhage- or endotoxemia-induced acute lung injury. Am J Physiol Lung Cell Mol Physiol. 2000 December; 279(6):L1137-45.

42 Yang H, et al. 2016. New insights into neutrophil extracellular traps: mechanisms of formation and role in inflammation. Front Immunol 7:302.

43 Yamashita C M, Lewis J F. 2012. Emerging therapies for treatment of acute lung injury and acute respiratory distress syndrome. Expert Opin Emerging Drugs 2012: 17(1).

44 Bellingan G, et al. 2014. The effect of intravenous interferon beta 1a (FP-1201) on lung CD73 expression and on acute respiratory distress syndrome mortality: an open-label study. The Lancet 2:98-107.

45 Unroe M, et al. 2010. One year trajectories of care and resource utilization for recipients of prolonged mechanical ventilation: a cohort study. Ann Intern Med 153: 167-175.

46 Gattinoni L, et al. 2010. Ventilator-induced lung injury: the anatomical and physiological framework. Crit Care Med 38:S539-548.

47 Gattinoni L, et al. 2010. Ibid.

48 Michaud G, Cardinal P. 2003. Mechanisms of ventilator-induced lung injury: the clinician's perspective. Critical Care 7:209-210.

49 Yamashita C M, Lewis J F. 2012.

50 Gattinoni L, et al. 2010. Ventilator-induced lung injury: the anatomical and physiological framework. Crit Care Med 38:S539-548.

51 Unroe M, et al. 2010. One year trajectories of care and resource utilization for recipients of prolonged mechanical ventilation: a cohort study. Ann Intern Med 153: 167-175.

52 Johnson E R, Matthay M A. 2010. Acute lung injury: epidemiology, pathogenesis, and treatment. J Aerosol Med Pulm Drug Delivery 23:243-252.

53 ClinicalTrials.gov number, NCT00979121.

54 ClinicalTrials.gov number NCT00979121 and NCT00719446.

55 Coppola S, et al., 2015. β-blockers in critically ill patients: from physiology to clinical evidence. Crit Care 19(1):119.

56 Saffarzadeh, M., Juenemann, C., Queisser, M. A., Lochnit, G., Barreto, G., Galuska, S. P., et al. (2012). Neutrophil extracellular traps directly induce epithelial and endothelial cell death: a predominant role of histones. PLoS ONE 7:e32366.

57 Michael J. Hickey & Paul Kubes. 2009. Nature Reviews Immunology 9, 364-375.

58 Herrera et al. 2014. DEspR roles in tumor vasculoangiogenesis, invasiveness, CSC-survival and anoikis resistance: a 'common receptor coordinator' paradigm. PLoS ONE 9(1): e85821.

59 Thomas L W, et al. 2010. Mcl-1: the molecular regulation of protein function. FEBS Letters 584:2981-2989.

60 Herrera V L, et al. 2010.

61 Edwards S W, et al. 2004. Regulation of neutrophil apoptosis by Mcl-1. Biochem Soc Trans 32:489-492.

62 El Kebir D, Filep J G. 2013.

63 Boyle A J, Sweeney R M, McAuley D F. 2013. Pharmacological treatments in ARDS: a state of the art update. BMC Medicine 11:166.

64 Erwig L P, Henson P M. 2008. Clearance of apoptotic cells by phagocytes. Cell Death and Differentiation 15: 243-250.

65 Mevorach D, et al. 1998. Complement-dependent clearance of apoptotic cells by human macrophages. J Exp Med 188:2313-2320.

66 Nasaraju T, et al. 2011. Excessive neutrophils and neutrophil extracellular traps contribute to acute lung injury in influenza pneumonitis. Am J Pathol 179: 199-210.

67 Nasaraju T, et al. 2011. Ibid.

68 Cutolo M, et al. 2008. Use of glucocorticoids and risk of infections. Autoimmun Rev 8:153-155.

69 Slminski A T, Smijewski M A. 2017. Glucocorticoids inhibit wound healing: novel mechanism of action. J Invest Dermatol 137:1012-1014, 70 Douda, D. N., Jackson, R., Grasemann, H., and Palaniyar, N. (2011). Innate immune collectin surfactant protein D simultaneously binds both neutrophil extracellular traps and carbohydrate ligands and promotes bacterial trapping. J. Immunol. 187, 1856-1865.

71 Gavillet M, et al. 2015. Flow cytometric assay for direct quantification of neutrophil extracellular traps (NETS) in blood samples. Am J Hematol 90:1155-1158.

72 Mevorach D, et al. 1998. Complement-dependent clearance of apoptotic cells by human macrophages. J Exp Med 188:2313-2320.

73 Gaggar A, Patel R P. 2016. There is blood in the water: hemolysis, hemoglobin, and heme in acute lung injury. Am J Physio Lung Cell Mol Physiol 311:L714-718.

74 Herrera V L, et al. 2014. DEspR roles in tumor vasculoangiogenesis, invasiveness, CSC-survival and anoikis resistance: a 'common receptor coordinator' paradigm. PLoS ONE 9(1): e85821.

75 Donahoe M. 2011. Acute respiratory distress syndrome: a clinical review. Pulm Circ 1:192-211.

76 Donahoe M. 2011. Ibid.

77 Donahoe M. 2011. ibid

Example 5

Just like activated PMNs, the antimicrobial killing properties of NETs can backfire and cause direct tissue injury and linger at the injury sites due to attachment of NETs to said injury sites. Cumulative research show that NETs contribute to secondary tissue injury in many major diseases—acute respiratory distress syndromes (ARDS), acute coronary syndromes (ACS), multi-organ failure (MOF) in ARDS, diabetes, COPD crisis, sickle cell crisis, acute kidney injury, traumatic brain injury, and sepsis—all of which remain unmet needs despite significant research, thus speaking to the importance of targeted inhibition of NETosing PMNs and NETs.

Described herein is the successful neutralization of activated PMN survival by humanized anti-DEspR IgG4S$^{228P}$ antibody (anti-DEspR humab), thus a priori preventing the progression to NETosis in ARDS patient blood samples, and successful anti-DEspR mAb targeting of human NETosing neutrophils, which then promote apoptosis hence facilitating clearance of the NETosing neutrophil, parallel to the induction of apoptosis of actPMNs for macrophage clearance or efferocytosis.

Described herein is a composite design of a targeted antibody-enzyme conjugate (AEC) with prevalidated components to attain target-specific efficacy needed to overcome the biophysical "mesh-scaffold" of NETs that entrap bacteria, platelets, as well as attach to the endothelium causing damage. Since there are no FDA-approved anti-NETs therapies, the anti-DEspR-DNAse-1 AEC provides a novel bioconjugate of 1) a NETs-targeting moiety and inhibitor: the highly specific, humanized hinge-stabilized S228P IgG4 anti-DEspR antibody NETs and NETosing neutrophils, and 2) a NETs structural-neutralizer and pre-processor: such as DNase1. As DNAse-I alone cannot completely degrade NETs in vitro and in vivo, (Farrera C, Fadeel B. 2013. Macrophage clearance of neutrophil extracellular traps is a silent process. J Immunol 191:2647-2656), conjugation of the anti-DEspR antibody with DNAse-I, targets DNAse-I to NETs, resulting in DNAse-1 pre-processing of NETs, and hence therapeutically enhance the clearance of NETs by monocyte-derived macrophages. This will provide targeted inhibition and biophysical neutralization and clearance of NETs. Just as lysis of neutrophils can be toxic, degradation of NETs is not enough, but rather the targeted inhibition and preprocessing of NETs for clearance and resolution.

Described herein is the preparation of the antiDEspR-humab-DNase1 therapeutic prototype with three components: the antibody targeting moiety, the connector moiety, and the payload moiety. Via recombinant DNA technology, the anti-DEspR-humab is produced with a linker at the C-terminal end of the Fc region. Suitable linkers, e.g., cleavable linkers are known in the art, e.g., a human neutrophil-elastase (HNE)-cleavable peptide linker. While all three are established components availing of established methodologies, the combination AEC-prototype is unique. Notably, neutrophil elastase is an active component on NETs, thus releasing DNAse 1 upon anti-DEspR targeted-binding of the AEC on NETs. Release DNAse 1 will then digest the DNA in NETs which has been shown to not be sufficient but attains "processed" NETs which then facililtates macrophage clearance. (Farrera C, Fadeel B. 2013. Macrophage clearance of neutrophil extracellular traps is a silent process. J Immunol 191:2647-2656), Need for the anti-DEspR targeted AEC. Regardless of the disease, the fact that NETs are the common culprit in diverse and pathogenically disparate diseases argues the importance and high-value priority of targeting NETs. As there are no FDA-approved drugs that can effectively neutralize NET-driven tissue injury and lower mortality in ARDS, hemorrhagic stroke, etc, an AEC therapeutic is needed. Studies show that deoxyribonuclease I (DNase1) can dismantle NETs, but "DNase1 alone" therapies are insufficient to resolve NETs-mediated pathologies or tissue injury in patients[5,6] and animal models,[7,8] indicating the need for an AEC. While PAD4 inhibitors or deficiency prevent NEToscis,[7] they cannot block already ongoing active NETs-driven tissue injury.

Described herein is the development of an anti-DEspR-mab targeted AEC that can promote macrophage clearance of NETs—thus breaking the vicious cycle of NET-induced endothelial injury-NETosis in ARDS, and opens the door for therapeutic applications for ACS, as well as prevent NETs-mediated thrombosis in multi-organ failure in ARDS, sepsis, and trauma. Cumulative data in multiple diseases in different organ systems implicate neutrophil extracellular traps (NETs) in the progression of disease, as well as in the feed forward mechanisms of end-stage life-threatening pathogenesis in acute respiratory distress syndrome (ARDS), acute coronary syndromes (ACS), multi-organ failure (MOF) in ARDS, sepsis, cancer, trauma.[1-3] Despite significant preclinical research[8,10,11] and clinical trials,[5,12,13] there is no FDA-approved curative-intent therapeutic for NETs-driven pathology or tissue injury.

Figures 18A, 18B:
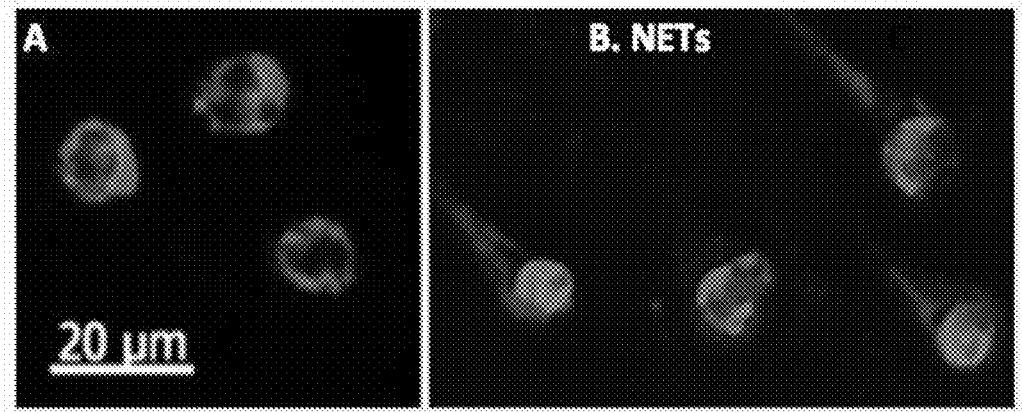
FIGS. 18A-18B depict immunofluorescence analysis of (FIG. 18A) human activated neutrophils, and (FIG. 18B) NETs.
Figure 18C:
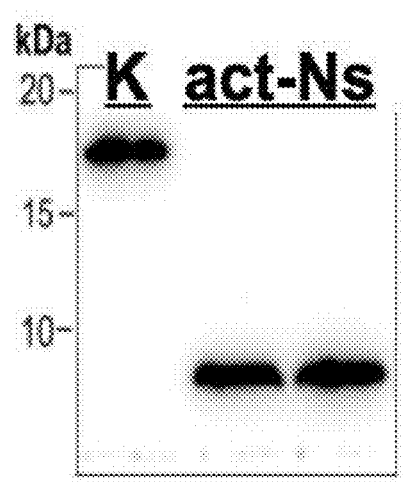
FIG. 18C depicts Western blot analysis of human kidney (K) and human activated neutrophils (act-Ns) probed with hu6g8-mab. Kidney DEspR is glycosylated ~17.5 kDa; DEspR in activated neutrophils is not glycosylated and exhibits the expected size, 9.8 kDa MW.

Described herein are the advantages of anti-DEspR mAb targeted AECs. DEspR, the dual endothelin1/signal peptide receptor,[9] is a validated target on human activated neutrophils and NETs. Hu6g8 binds human activated neutrophils (FIG. 18A) and NETs (FIG. 18B), as confirmed by Western Blot analysis of DEspR protein in human kidney (K), and activated neutrophil samples, act-Ns (FIG. 18C). Humanized anti-DEspR-mab (hu6g8 mab) is an ideal targeting moiety. Hu6g8 is the multi-species Human/NHPrimate/Rat reactive humanized-deimmunized anti-DEspR-mab with a hinge-stabilized IgG4S228P/kappa Fc region (FIG. 17A) to avoid (ADCC-antibody dependent cell-mediated cytotoxicity, CDC-complement dependent cytotoxicity), and to eliminate loss of targeting upon Fab arm exchange typical of native IgG4 isotype. Selected from multiple candidates, hu6g8 exhibits improved binding affinity to DEspR on intact cells compared to its murine precursor mab (FIG. 17B), and improved functionality in targeting activated neutrophils with survival decreasing after 6-hours of ex vivo treatment (FIG. 17C). Through recombinant DNA technology, the antibody design incorporates: a) avoidance of T-cell epitopes for low immunogenicity; b) optimization of heavy and light chain interactions for stability of variable domains; and, c) exclusion of destabilizing post-translational modification sites [e.g., deamidation, oxidation]. The targeting of DEspR+ NETs, but sparing of DEspR(−) quiescent neutrophils via the anti-DEspR mAb is also novel. The use of DNAse 1 (30.1 kDa) is advantageous as this is a circulating protein in the plasma hence will not induce a foreign substance response, is FDA-approved for cystic fibrosis,[17] and has been shown to be multi-site fluorophore conjugatable without losing enzymatic activity. The use of human neutrophil-elastase cleavable linker is advantageous as this connector-peptide can be added by recombinant technology and HNE is enriched on NETs and actually a reason for the injurious properties of NETs. HNE is desirable for local therapeutic delivery [Owen C A, Campbell E J. J Leukocyte Biol 1999, 65 (2) 137-150], has specificity for small uncharged amino acids particularly alanine (A) and valine (V) [Meers P. Adv Drug Delivery Rev. 2001. 53 (3) 265-272]. The synthetic peptide Ala-Ala-Pro-Val has been shown to be HEN-specific [Wiesner O, Litwiller R D, Hummel A M, Viss M A, McDonald C J, Jenne D E, Fass D N, Specks U. FEBS Lett 2005, 579 (24)5305-5312] and successful for drug delivery [Pak C C, Erukulla R K, Ahl P L, Janoff A S eers P. Biochim Biophys Acta 1999, 1419 (2) 111-126] The advantages of all three in an AEC is novel and robust as the targeted delivery and release of DNAse 1 on NETs can attain in vivo efficacy of what has been shown in vitro, the induction of macrophage uptake-and-clearance of NETs upon DNAse 1 digest of NETs DNA. In summary, targeting the intravascular NETs sites. The humanized anti-DEspR-mab with a hinge-stabilized IgG4/kappa Fc region to avoid Fab arm exchange in vivo and ensuing loss of targeting was selected. Additionally, this avoids immune effector functions of IgG1 mAbs (ADCC, CDC), which would worsen endothelial injury. Importantly, the antibody binds to activated neutrophils and NETs (FIG. 18A-18C), and inhibits the extended survival of activated neutrophils. Thus, inhibition of activated neutrophils to pre-empt NETosis is accomplished, in addition to the targeting moiety function. The DNAse will digest the 'naked' DNA in between nucleosomes (DNase1 hypersensitive sites), as well as the DNA wrapped around histones in the nucleosomes at DARNS (DNase1 annotated regions of nucleosome stability) sites.[16]

REFERENCES

1. Papayannopoulos, V. Neutrophil extracellular traps in immunity and disease. Nat. Rev. Immunol. (2017). doi: 10.1038/nri.2017.105
2. Mitsios, A., Arampatzioglou, A., Arelaki, S., Mitroulis, I. & Ritis, K. NETopathies? Unraveling the Dark Side of Old Diseases through Neutrophils. Front. Immunol. 7, 678 (2016).
3. Jorch, S. K. & Kubes, P. An emerging role for neutrophil extracellular traps in noninfectious disease. Nat. Med. 23, 279-287 (2017).
4. Brinkmann, V. et al. Neutrophil Extracellular Traps Kill Bacteria. Science (80-). 303, 1532-1535 (2004).
5. Davis, J. C. et al. Recombinant human Dnase I (rhDNase) in patients with lupus nephritis. Lupus 8, 68-76 (1999).
6. Shah, P. L. et al. In vivo effects of recombinant human DNase I on sputum in patients with cystic fibrosis. Thorax 51, 119-25 (1996).
7. Kolaczkowska, E. et al. Molecular mechanisms of NET formation and degradation revealed by intravital imaging in the liver vasculature. Nat. Commun. 6, 6673 (2015).
8. Verthelyi, D., Dybdal, N., Elias, K. A. & Klinman, D. M. DNAse treatment does not improve the survival of lupus prone (NZB6NZW)F1 mice. Lupus 7, 223-230 (1998).
9. Herrera, V. L. M. et al. Confirmation of translatability and functionality certifies the dual endothelin1/VEGFsp receptor (DEspR) protein. BMC Mol. Biol. 17, 15 (2016).
10. Macanovic, M. et al. The treatment of systemic lupus erythematosus (SLE) in NZB/W F1 hybrid mice; studies with recombinant murine DNase and with dexamethasone. Clin. Exp. Immunol. 106, 243-52 (1996).
11. Knight, J. S. et al. Peptidylarginine deiminase inhibition disrupts NET formation and protects against kidney, skin and vascular disease in lupus-prone MRL/lpr mice. Ann. Rheum. Dis. 74, 2199-2206 (2015).
12. van Bijnen, S., Wouters, D., van Mierlo, G. J. & Muus, P. Neutrophil Extracellular Trap Formation In PNH Patients With and Without a History Of Thrombosis—Effects Of Eculizumab. Blood 122, (2013).
13. Patel, S. et al. Nitric oxide donors release extracellular traps from human neutrophils by augmenting free radical generation. Nitric Oxide 22, 226-234 (2010).
14. Harbury, P. B., Zhang, T., Kim, P. S. & Alber, T. A switch between two-, three-, and four-stranded coiled coils in GCN4 leucine zipper mutants. Science 262, 1401-7 (1993).
15. Hu, J. C., O'Shea, E. K., Kim, P. S. & Sauer, R. T. Sequence requirements for coiled-coils: analysis with lambda repressor-GCN4 leucine zipper fusions. Science 250, 1400-3 (1990).
16. Winter, D. R., Song, L., Mukherjee, S., Furey, T. S. & Crawford, G. E. DNase-seq predicts regions of rotational nucleosome stability across diverse human cell types. Genome Res. 23, 1118-1129 (2013).
17. Shah, P. L., Scott, S. F., Geddes, D. M. & Hodson, M. E. Two years experience with recombinant Human DNase I in the treatment of pulmonary disease in cystic fibrosis. Respir. Med. 89, 499-502 (1995).
18. Price, P. A., Stein, W. H. & Moore, S. Effect of divalent cations on the reduction and re-formation of the disulfide bonds of deoxyribonuclease. J. Biol. Chem. 244, 929-32 (1969).
19. Ragaller, M. & Richter, T. Acute lung injury and acute respiratory distress syndrome. J. Emerg. Trauma. Shock 3, 43-51 (2010).
20. Liang, J. & Liu, B. ROS-responsive drug delivery systems. Bioeng. Transl. Med. 1, 239-251 (2016).
21. Liao, T. H., Ting, R. S. & Yeung, J. E. Reactivity of tyrosine in bovine pancreatic deoxyribonuclease with p-nitrobenzenesulfonyl fluoride. J. Biol. Chem. 257, 5637-44 (1982).
22. Owen, C. A., Campbell, M. A., Sannes, P. L., Boukedes, S. S. & Campbell, E. J. Cell surface-bound elastase and cathepsin G on human neutrophils: a novel, non-oxidative mechanism by which neutrophils focus and preserve catalytic activity of serine proteinases. J. Cell Biol. 131, 775-89 (1995).

Example 6

DEspR+CD11b+'Rogue' Neutrophils or NETosis-Prone Neutrophils

Immuno-cytostaining of human stress-activated neutrophils with characteristic polylobulated nuclei detects DEspR+ expression in varying stages of neutrophil extracellular trap (NET) formation (NETosis) marked by different degrees of DNA marginalization to subsequent extrusion (FIG. 21A-21B).

The presence of DEspR on activated neutrophils and in early vital NETosis (ie, intact cell membrane) supports anti-DEspR blocking antibody as targeted therapy to inhibit DEspR+ activated neutrophils and activated neutrophils undergoing vital NETosis.

The detection of DEspR+/CD11b+ neutrophils and DEspR+/CD11b+ neutrophils in early vital NETosis in some but not all CD11b+ neutrophils identifies a subset of CD11b+ activated neutrophils that are NETosis-prone or early NETosing neutrophils. Since NETs are also implicated in neutrophil-driven secondary tissue injury, an increase in DEspR+ expression in neutrophils provides a biomarker for NETs and NETosing neutrophils, and an accessible membrane-receptor target for targeted therapies that blocks activated neutrophils and NETosis via anti-DEspR mAb. Inhibition of activated neutrophil survival by DEspR's downstream effect of decreasing Mcl1, a tightly-regulated survival protein required for neutrophil survival, results in neutrophil apoptosis which is the endogenous mechanism to effectively shutdown neutrophil function without release of harmful proteases and reactive oxygen species (ROS). Induction of apoptosis also promotes clearance by monocyte/macrophage efferocytosis, thus facilitating active resolution of the hyper-inflammatory state.

Notably, not all activated neutrophils are DEspR+ (FIG. 24). This elucidates a mechanism for safety of anti-DEspR therapy—ie, not all CD11b+ activated neutrophils are inhibited, thus allowing normal regulated neutrophil functions to proceed.

The presence of DEspR on human activated stress-activated neutrophils and bacterial lipopolysaccharide (LPS)-activated neutrophils is confirmed on western blot analysis of human neutrophils. Human kidney tissue serves as positive control (FIG. 25). The smaller DEspR size in neutrophil samples N1 and N2 is consistent with non-glycosylated DEspR (~9.5 kDa), in contrast to glycosylated DEspR (~17 kDa). The non-glycosylated DEspR in neutrophils reflects an 'open-access' to phosphorylation sites, since intracellular O-glycosylation is a mechanism to modulate, if not impede, phosphorylation sites. Detection of glycosylated and non-glycosylated DEspR protein indicates a mechanism of modulation of DEspR phosphorylation as O-glycosylation is associated with modulation of phosphorylation, and N-glycosylation allows for intracellular interactions with galectin 1 and galectin 3, both of which can serve as shuttling mechanism for observed DEspR-nuclear transport.

In silico analysis demonstrates that DEspR has multiple serine and threonine phosphorylation sites (FIG. 30) mapping to DEspR S72, and T76, 77, 84 with predictive scores 3.7- to 4.3-fold greater than cutoff values. DEspR phosphorylation, internalization, and DEspR nuclear localization in neutrophils would facilitate DEspR promoting and maintaining neutrophil survival in hypoxic or cytotoxic microenvironments, thus demonstrating how DEspR inhibition via anti-DEspR mAb binding decreases neutrophil survival. These serine and threonine phosphorylation sites are consistent with the detection of activated signaling phosphoproteins from ligand-specific activation of transfected human DEspR in permanent Cos1 DEspR-transfectants. (Herrera et al 2014).

In silico analysis detected several putative serine (S) and threonine (T) putative O-glycosylation motifs or 'O-sequons' (FIG. 27). These are consistent with detection of glycosylated DEspR pulldown protein on Western blot analysis that were incompletely digested by PNGase-F, thus indicating both non-N-glycosylation and O-glycosylation [Herrera et al 2016]. DEspR O-glycosylation sites primarily in the transmembrane domain are exposed to intracellular O-glycosylation upon internalization of DEspR on ligand or antibody binding.

FACs analysis of patient blood sample from patients with acute respiratory distress syndrome (ARDS) detected DEspR+/CD11b+ activated neutrophils as a subset of CD11b+ activated neutrophils that is low in ARDS-patient survivors (FIG. 27), but elevated in ARDS-patient non-survivors (FIGS. 28 and 29). In contrast to the detection of low levels of DEspR+/CD11b+ activated neutrophils in ARDS survivors, a high level of DEspR+/CD11b+ activated neutrophils is detected in ARDS-patient non-survivor (FIG. 29). This observation of differential levels indicates that DEspR+CD11b+ subset of activated neutrophils could be involved in the progression of ARDS to multi-organ failure (MOF), the cause of death and long term sequelae from ARDS.

Additionally, DEspR+/CD11b+ monocytes are also detected in non-surviving ARDS patient (FIG. 27), thus identifying a monocyte subset that crosstalks with DEspR+/CD11b+ neutrophils to propagate neutrophil-driven vicious cycles of {tissue injury-neutrophil response-tissue injury. Both neutrophils and monocytes are implicated in ARDS pathogenesis.

A new subset of activated neutrophils, DEspR+/CD11b+, are associated with ARDS mortality. Aside from an increased number of DEspR+/CD11b+ neutrophils, these DEspR+ neutrophils also exhibit increased DEspR-receptor expression (intensity) per neutrophil, as seen in A02-ARDS patient non-survivor, in contrast to age-, sex-, sampling time-matched ARDS-patient survivor (FIG. 30). This corroborates the DEspR+/CD11b+ subset of neutrophils that is associated with worse outcomes in ARDS, indicating that DEspR+/CD11b+"rogue" neutrophils underlie ARDS progression and neutrophil-mediated pathogenic mechanisms that increase mortality. Inhibition of this subset is therefore key to attenuating ARDS, secondary edema expansion in stroke and brain trauma, and to stopping neutrophil-mediated immune-evasion in order to enhance checkpoint inhibitors in cancer. Inhibition of this subset was detected using anti-DEspR mAb treatment DEspR+/CD11b+ neutrophil levels were associated with non-survival outcome better than other known ARDS clinical parameters—PaO2/FiO2, serum creatinine, neutrophil lymphocyte ratio (FIG. 31). This indicates that DEspR+/CD11b+ expression identifies a dysregulated subset of "rogue" activated neutrophils which when elevated >50% lead to vicious cycles of neutrophil-driven injury, in contrast to low levels <20% and CD11b+ but DEspR(−) neutrophils. DEspR immunophenotyping provides a biomarker for impending progression of neutrophil-driven secondary injury in the lung or systemically in ARDS as well as in other pathologies where activated neutrophils are also excessive and dysregulated such as, secondary brain injury in stroke, anoxic and traumatic brain injury, multi-organ failure from trauma or infection, etc.

The association of DEspR+/CD11b+ with worsened outcomes in ARDS patients better than current clinical parameters (PaO2/FiO2 ratio, serum creatinine, and neutrophil-lymphocyte ratio (NLR) is also seen on trend analysis of said clinical parameters (FIG. 32). Treatment with anti-DEspR humanized IgG4S228P antibody decreased survival of DEspR+/CD11b+ neutrophils when elevated (as seen in patient A02 with average 59% DEspR+/CD11b+ neutrophils), in contrast to no effect when DEspR+ expression is minimally elevated in cd11b+ neutrophils (as seen in patient A04 1%, A05 3%) (FIG. 33). Some efficacy is observed but variable (as seen in A06) with levels around 16% DEspR+/CD11+ neutrophils. These observations demonstrate that anti-DEspR mAb therapy can stop DEspR+/CD11b+ activated neutrophils which underlie tissue injury pathogenesis. These data are summarized in Table 4.

TABLE 4

Summary of ABTM-468 treatment (10 µg/ml) effects on DEspR$^+$/CD11b$^+$ neutrophil survival in ARDS patient whole blood samples.

| ID | Survival | Time from ARDS-Diagnosis (hrs) | ABTM-468 (µg/ml) | Incubation time (hrs) | Mean (SD) DEspR$^+$/CD11b$^+$ Neutrophils (%)$^a$ | Expected (%)$^b$ | Observed (%)$^c$ | P$^d$ |
|---|---|---|---|---|---|---|---|---|
| A02 | Died | 79 | 10 | 24 | 59.2 (5.1) | 59.2 | 33.5 | 0.029 |
| A03 | DNR, D. | 96 | 10 | 24 | 1.5 (0.5) | 1.5 | No effect | |
| A04 | Surv | 96 | 10 | 6 | 0.9 (0.3) | 0.9 | No effect | |

TABLE 4-continued

Summary of ABTM-468 treatment (10 µg/ml) effects on DEspR+/
CD11b+ neutrophil survival in ARDS patient whole blood samples.

| ID | Survival | Time from ARDS-Diagnosis (hrs) | ABTM-468 (µg/ml) | Incubation time (hrs) | Mean (SD) DEspR+/CD11b+ Neutrophils (%)[a] | Expected (%)[b] | Observed (%)[c] | P[d] |
|---|---|---|---|---|---|---|---|---|
| A05 | Surv | 72 | 10 | 6 | 3 (0.6) | 3 | No effect | |
| A06 | Surv | 48 | 10 | 6 | 16.1 (4.1) | 16.1 | 14.5 | n.s. |

Note:
ex vivo analysis in whole blood to simulate patient circulating milieu.
[a]Mean DEspR+/CD11b+ neutrophils as % at baseline (incubation time = 0 hrs);
[b]Expected decrease in neutrophil survival as %;
[c]Observed decrease in neutrophil survival as %;
[d]Mann-Whitney Rank Sum Test.
Experiments were performed in 4-5 replicates.

The association of increased number and intensity of DEspR+/CD11b+ neutrophils with non-survival in ARDS patients indicate that DEspR+/CD11b+ neutrophils are 'rogue' neutrophils that are dysregulated leading to excessive neutrophil bacterial-killing functions. Dysregulated excess occurs when normal activation-resolution mechanisms are uncoupled, hence drive tissue injury rather than effect the normal neutrophil response that defends the host against bacteria or promotes wound healing with inherent triggering of active resolution upon activation.

To further test the impact of anti-DEspR treatment on DEspR+/CD11b+ activated neutrophils, neutrophil-lymphocyte ratios were tracked in a nude rat xenograft tumor model of pancreatic cancer peritoneal metastasis established by injection of Panc1-cancer stem cells (CSCs) into the peritoneal space, Panc1-CDX PPM rat model. Neutrophils also contribute to the aggressiveness of cancers, including pancreatic cancer, and increased NLR is associated with worse outcomes and poor response to treatment. This ratio was elevated in untreated advanced Panc1-CDX PPM (FIG. 34). Concordantly, the NLR was not elevated with anti-DEspR treatment beginning on day 21 and which also resulted in increasing overall survival of tumor+ rats.

To confirm DEspR role in decreasing survival in stress conditions and increasing apoptosis in neutrophils, DEspR roles in the regulation of survival of, and apoptosis in tumor cells were tested. It is known that induction of apoptosis in tumor cells enhances the efficacy of chemotherapy. So the combination of anti-DEspR mAb treatment and gemcitabine, the standard of care for pancreatic cancer were tested (FIG. 35A-35B). In vitro treatment of pancreatic tumor cells (2 cell lines, Panel 1 and MiaPaCa2) with combination therapy, Gemcitabine standard of care and hu-6g8 anti-DEspR mAb (ABTM-468) resulted in synergistic effects, ie, greater chemotherapy efficacy.

The observations of anti-DEspR/gemcitabine synergy supports the potential of anti-DEspR mAb therapy to be a compelling partner for combination with checkpoint inhibitors. Notably, other combination therapies of gemcitabine and targeted therapies have not had compelling clinical benefit in pancreatic cancer patients (e.g., GEM+Erlotinib, or GEM+Avastin, or GEM+checkpoint inhibitors in pancreatic cancer). The paradigm of unique combinatorial synergy was further tested in vivo. As shown in FIG. 36, in vivo treatment of rats with low-dose (1 mg/kg i.v.) anti-DEspR humanized IgG4S228P and gemcitabine exhibited greater efficacy than gemcitabine alone. The combination [anti-DEspR+gemcitabine] therapy regressed pancreatic peritoneal metastatic tumors, as some tumor+ rats treated with combination therapy (ComboTx) had no tumors after documented tumor burden at start of therapy. Moreover, there was no ascites in ComboTx-rats. Gut distention from gut-dysfunction is also evident in saline mock-treated (Tx) control. (FIG. 36).

Quantitation of tumor burden showed that comboTx rats also exhibited less tumor burden in the greater and lesser omental apron compared with mock-treated control (saline) and standard of care gemcitabine (GEM) treated rats (Table 5). Importantly, metastasis to the liver and retroperitoneal space, and ascites were all prevented/inhibited by ComboTx.

TABLE 5

| Rat ID | Group | Ascites | Tumor weight (g) Greater Omentum | Tumor L × W Lesser Omentum | Tumors over Large Intestine: dimension L × W (ellipsoid) in cm | | | |
|---|---|---|---|---|---|---|---|---|
| 8282 | Como | none | No tumors | — | — | | | |
| 8283 | Combo | none | No tumors | — | — | | | |
| 8304 | Combo | none | 1.5064 | 1 cm × .4 cm × 0.6 cm  0.2 cm | .8 cm × .5 cm | | | |
| 8305 | Combo | none | 1.26 | — | .1 × .1 cm | .3 cm × .1 cm | .3 cm × .2 cm | .1 cm × .1 cm | .3 cm × .1 cm |
| 8307 | Combo | none | 1.4334 | 3 cm × .2 cm | .9 cm × .2 cm | | | |
| 8308 | Combo | none | 2.2264 | — | — | | | |
| 8299 | Saline | Bloody (9 mls) | 3.1299 | 1.7 cm × 1.1 cm | 1.1 cm × .6 cm | 1.1 cm × .7 cm | | |
| 8269 | GEM | Bloody 1.5 mls | 1.6351 | 0.2 cm × 0.2 cm | .9 cm × .6 cm | .8 cm × .4 cm | | |

TABLE 5-continued

| Rat ID | Tumors over Large Intestine: dimension L x W (ellipsoid) in cm | | | | Tumors on Liver | Retro-peritoneal tumors |
|---|---|---|---|---|---|---|
| 8282 | — | | | | — | — |
| 8283 | — | | | | — | — |
| 8304 | .6 cm x .6 cm | | | | — | — |
| 8305 | .3 cm x .1 cm | .6 cm x .6 cm | .4 cm x .4 cm | .3 cm x .2 cm | .1 cm x .1 cm | .1 cm x .1 cm | — | — |
| 8307 | .9 cm x .2 cm | | | | — | — |
| 8308 | — | | | | — | — |
| 8299 | 1.1 cm x .7 cm | 2 cm x .5 cm | .4 cm x .4 cm | | 2.5 cm x 1.5 cm | 2 cm x 1 cm | 3.2 cm x 2 cm |
| 8269 | .8 cm x .4 cm | 1.6 cm x .4 cm | .2 cm x .6 cm | | 1.7 cm x .7 cm | — |

Tumor regression is consistent with observations in the rat spontaneous mammary tumor model in an immunocompetent rat host. Tumor regression in both immune-compromised and immune-competent xenograft tumor host shows the role of neutrophils in tumor progression, metastatic aggressiveness, therapy resistance—all of which contribute to decreased host overall survival. These observations collectively support hu-6g8 as a novel therapeutic for new combination therapies with chemotherapy or checkpoint inhibitors wherein neutrophils have been implicated in therapy resistances—inherent and acquired—respectively.

DEspR+ expression in NET-prone neutrophils are detected in in pancreatic cancer stroma (FIG. 37A-37D), along with DEspR+ tumor cells, tumor blood vessels (FIG. 19A-19F), which is corroborated in vitro by FACs analysis (FIG. 19G-19J) and in vitro tissue culture studies (FIG. 20A-20F) of two pancreatic cell lines. This niche-colocalization provides a crosstalk mechanism for neutrophil roles in facilitating tumor invasion, metastasis, therapy resistance and immune evasion. This is supported by in vivo studies showing efficacy of DEspR inhibition (FIG. 21) and documenting presence of anti-DEspR antibody in the blood stream after bolus infusion (FIG. 22).

DEspR+ activated neutrophils and/or activated vital NETosis-prone neutrophils are also detected in metastatic PDAC tumors in pancreatic peritoneal metastasis or carcinomatosis (FIG. 38A-38B). The presence of DEspR+ NET-prone activated neutrophils and/or NETs in the tumor stroma of metastatic pancreatic cancer patient tumor along with direct-cell-to-cell contact with invasive tumor cells in the stroma (FIG. 38A-38B) indicate that DEspR+ neutrophils comprise a pro-tumorigenic neutrophil subset that promotes micro-to-macro switch of microtumors spanning an angiogenic switch and immune evasion switch for microtumors beyond 1-2 mm—both of which have to occur for successful metastasis or successful conversion of pre-cancerous lesions to cancer. Notably, not all dormant metastatic tumors become metastatic cancer, and in parallel, all pre-cancerous lesions progress to cancer, as some precancerous lesions do regress.

In a CSC-derived pancreatic carcinomatosis xenograft tumor model in nude rats, anti-DEspR mAb ABTM-468 treatment reduced gut ischemia, serous or hemorrhagic ascites, distended gut, and ischemic-hemorrhagic gut (black gut) and gut dysfunction (FIG. 39). These data indicate that anti-DEspR treatment reduced DEspR+ NET-prone neutrophil- and/or NETs-mediated roles in cancer comorbidities.

In pancreatic peritoneal carcinomatosis, neutrophil-mediated or NETs-mediated tissue injury, vaso-occlusion and/or microthromboses induce comorbid complications such as: a) gut hemorrhage and microthromboses ('black gut') from activated neutrophil- and NETs-driven secondary tissue injury as seen in ARDS, stroke, b) hemorrhagic ascites, c) gut ileus or dysfunction (distended dysfunctional gut) from microthromboses or micro-bleeds. The reduction of these comorbid-complications in vivo by anti-DEspR mAb treatment in vivo (using humanized anti-DEspR mAb or ABTM-468) demonstrates that anti-DEspR mAb therapy is able to stop activated NETosis-prone neutrophil- and NETs-induced comorbid complications in pancreatic cancer.

DEspR+ inflammatory cells, NETosis-prone activated neutrophils, are detected in the tumor stroma in all stages of pancreatic cancer (PDAC) (FIG. 40), similar to metastatic tumors with an increasing trend towards Stage IV-PDAC. The presence of DEspR+'rogue' neutrophils in all stages including metastatic tumors indicates the importance of neutrophil-tumor cell interactions towards tumor progression towards highest stage, as well as importance in the progression of pre-cancer lesions to malignancy at the other end of the PDAC continuum. Anti-DEspR mAb therapy inhibition of NETosis-prone neutrophils is a novel approach to averting precancer-lesions progressing towards malignancy.

Anti-DEspR mAb treatment reduced albuminuria in a hypertensive chronic kidney disease rat mode with moderate severe glomerulonephrosclerosis (FIGS. 41A-41C). As the response was observed within 1 week, data indicate a quick-turnaround mechanism of improvement based on elimination of neutrophil-mediated secondary tissue injury via inhibition of DEspR+ NETs-prone activated neutrophils by ABTM-468 treatment. These data demonstrate ABTM-468 efficacy in inhibiting activated neutrophils and NETosis-prone neutrophils in chronic kidney disease resulting in improved kidney function measured as decreased albuminuria and UACR.

Anti-DEspR effectively decreases survival of a key subset of human activated CD11b+ neutrophils associated with neutrophil driven secondary tissue injury as seen specifically in ARDS patient neutrophil and applicable to all other diseases with neutrophil-mediated tissue injury. ARDS is representative of one of the worst extremes of neutrophil-driven secondary tissue injury.

Anti-DEspR therapy increased sensitivity to gemcitabine by eliminating therapy-resistance mechanisms derived from DEspR+ activated neutrophils and tumor associated neutrophils, and from DEspR+ therapy resistant, anoikis resistant tumor cells. The greater efficacy of the combination anti-DEspR+chemotherapy in a nude rat xenograft tumor model demonstrates the inhibition of neutrophil-driven mechanisms that contribute to inherent or acquired therapy resistance to anticancer cytotoxic therapies, and checkpoint inhibitors, thus supporting the combination therapies with chemotherapies and/or checkpoint inhibitors.

Detection of DEspR+/CD11b+ neutrophils and NETs in human blood samples comprise a robust diagnostic or prognostic indicator, strengthened by the fact that DEspR inhibition is effective therapy to counter pathogenic mechanisms in complex life-threatening diseases exacerbated by neutrophil-driven secondary tissue injury.

Example 7

DEspR protein is co-localized with adenosine deaminase acting on RNA-1 [ADAR-1] in the cell nucleus of pancreatic tumor cells. Because neutrophils are known to change phenotype when cultured, even if freshly isolated, the co-localization of DEspR and ADAR-1 was done in pancreatic tumor cells, Panc1 following standard methods described below. Confocal microscopy analysis of Immunofluorescence staining demonstrates that DEspR and ADAR1 are present in the nucleus, and colocalize in some but not all areas of the nucleus (FIG. 42). These data support bi-specific anti-DEspR/anti-ADAR1 bibodies.

Permeabilization: 1 ml of 0.5% Triton X-100 in PBS was added to plate and incubated at room temperature for 15 minutes. Triton X-100 was removed, and plate was washed 3× with PBS (added to side of plate, removed from side to not disturb glass cover slip)

Blocking: 2 ml of 5% BSA in PBS solution was added, plate was blocked for 2 hrs at 4° C.

Staining (Primary): After removal of blocking media, anti-DEspR AF568 (HEK) antibody (10 ug/ml) and ADAR1 (0.73 ug/ml) in 1% BSA incubated for 4 hrs at 4° C. Removed primary staining solution and washed 3× with 1 ml 1% BSA in PBS Staining (Secondary): Secondary anti-Rabbit IgG AF-488 (0.5 ug/ml) in 1% BSA incubated for 2 hrs at 4° C. Removed primary staining solution and washed 3× with 1 ml 1% BSA in PBS; maintained in 1 ml PBS. Imaging performed with Leica SP5 confocal microscope.

What is claimed herein is:

1. A method of preventing or decreasing neutrophil extracellular trap (NET) levels or release in a subject determined to have increased levels of NETs as indicated by the presence of DEspR+ neutrophils, as compared to a healthy subject, the method comprising administering a therapeutically effective amount of an anti-DEspR antibody reagent to the subject determined to have DEspR+ neutrophils.

2. The method of claim 1, wherein the DEspR antibody reagent is an antigen-binding fragment of an anti-DEspR antibody.

3. The method of claim 1, wherein the anti-DEspR antibody reagent is a monoclonal antibody.

4. The method of claim 1, wherein the anti-DEspR antibody reagent comprises complementary determining regions selected from SEQ ID Nos: 9-11, 5-7, 21-23, and 25-27.

5. The method of claim 1, wherein the subject has a condition or disease wherein NETs; or NETosing or NETting neutrophils contribute to pathogenesis, chronicity, or worsening of disease.

6. The method of claim 5, wherein the condition or disease is selected from the group consisting of:
systemic inflammatory response syndrome (SIRS); acute lung injury (ALI); acute respiratory distress syndrome (ARDS); multi-organ failure or multi-organ dysfunction syndrome (MODS); multi-organ failure or multi-organ dysfunction syndrome (MODS) from ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections; cytokine storms induced by drugs or any agent; ischemic or hemorrhagic stroke; secondary brain injury in stroke; myocardial ischemia/infarction; atherosclerotic vulnerable plaques; atherosclerotic thrombosis; coronary artery disease; acute coronary syndrome; heart failure; reperfusion injury; comorbidities in kidney dialysis patients; thrombosis in kidney dialysis patients; endothelial dysfunction in kidney dialysis patients; complement activation; ischemic or drug-induced hemorrhagic transformation in the brain; hemorrhagic encephalopathy; traumatic brain injury; anoxic brain injury; chronic kidney disease; cancer; an actPMN-dependent cancer; diabetes; type 1 diabetes; type 2 diabetes; angiopathies; vasculopathies; vasculitis; end-organ complications; retinopathy; diabetic kidney disease; poor wound healing of diabetic ulcers; deep vein thrombosis; cancer metastasis; cancer therapy resistance; immune evasion; systemic microthrombosis; chemotherapy-induced microthrombosis; atherosclerotic thrombosis; systemic lupus erythematosus (SLE); lupus nephritis; SLE-accelerated atherosclerosis; rheumatoid arthritis; COPD; cystic fibrosis; pulmonary disease; Alzheimer's Disease; cognitive decline; sickle cell disease; inflammatory bowel disease (IBD); Crohn's disease; ulcerative colitis; and indeterminate colitis.

7. The method of claim 1, wherein the activity of neutrophils in the subject is decreased by administration of the anti-DEspR antibody reagent.

8. The method of claim 7, wherein the neutrophils are activated neutrophils (actPMNs) or CD11b+ neutrophils.

9. A method of decreasing or treating tissue injury exacerbated or caused by neutrophil extracellular trap (NET) levels or release, in a subject in need thereof, the method comprising administering a therapeutically effective amount of an anti-DEspR antibody to a subject determined to have circulating CD11b+ DEspR+ neutrophils or DEspR+ NETosing neutrophils; whereby the NET levels or release are reduced.

10. The method of claim 9, wherein the tissue injury comprises organ-specific or multi-organ dysfunction or failure.

11. The method of claim 10, wherein the subject has or is diagnosed as having a condition selected from the group consisting:
systemic inflammatory response syndrome (SIRS); acute lung injury (ALI); acute respiratory distress syndrome (ARDS); and multi-organ failure or multi-organ dysfunction syndrome (MODS).

12. The method of claim 9, wherein the subject has or is diagnosed as having a condition selected from the group consisting of:
systemic inflammatory response syndrome (SIRS); acute lung injury (ALI); acute respiratory distress syndrome (ARDS); multi-organ failure or multi-organ dysfunction syndrome (MODS); multi-organ failure or multi-organ dysfunction syndrome (MODS) from ARDS, hemorrhagic shock, surgery, burns, or sepsis; sepsis; sepsis-induced coagulopathy; trauma; multiple sclerosis; acute kidney injury (AKI); AKI-associated tubular necrosis and distant organ injury; post-trauma surgery; hemorrhagic shock; infections; cytokine storms induced by drugs or any agent; myocardial ischemia/infarction; atherosclerotic vulnerable plaques; atherosclerotic thrombosis; coronary artery disease; acute coronary syndrome; heart failure; reperfusion injury; comorbidities in kidney dialysis patients; thrombosis in kidney dialysis patients; endothelial dysfunction in kidney dialysis patients; complement activation; ischemic or drug-induced hemorrhagic transformation in the brain; hemorrhagic encephalopathy; traumatic brain injury; anoxic brain injury; chronic kidney disease; diabetes; type 1 diabetes; type 2 diabetes; angiopathies; vasculopathies; vasculitis; end-organ complications; diabetic kidney disease; poor wound healing of diabetic ulcers; deep vein thrombosis; immune evasion; systemic microthrombosis; chemotherapy-induced microthrombosissystemic lupus erythematosus (SLE); lupus nephritis; SLE-accelerated atherosclerosis; COPD; cystic fibrosis; pulmonary disease; cognitive decline; sickle cell disease; inflammatory bowel disease (IBD); Crohn's disease; ulcerative colitis; and indeterminate colitis.

13. The method of claim 4, wherein the anti-DEspR antibody reagent comprises the following complementary determining regions (CDRs):
(a) a light chain CDR1 having the amino acid sequence of SEQ ID NO: 9;
(b) a light chain CDR2 having the amino acid sequence of SEQ ID NO: 10;
(c) a light chain CDR3 having the amino acid sequence of SEQ ID NO: 11;
(d) a heavy chain CDR1 having the amino acid sequence of SEQ ID NO: 5;
(e) a heavy chain CDR2 having the amino acid sequence of SEQ ID NO: 6; and
(f) a heavy chain CDR3 having the amino acid sequence of SEQ ID NO: 7.

14. The method of claim 4, wherein the anti-DEspR antibody reagent comprises the following complementary determining regions (CDRs):
(a) a light chain CDR1 having the amino acid sequence of SEQ ID NO: 25;
(b) a light chain CDR2 having the amino acid sequence of SEQ ID NO: 26;
(c) a light chain CDR3 having the amino acid sequence of SEQ ID NO: 27;
(d) a heavy chain CDR1 having the amino acid sequence of SEQ ID NO: 21;
(e) a heavy chain CDR2 having the amino acid sequence of SEQ ID NO: 22; and
(f) a heavy chain CDR3 having the amino acid sequence of SEQ ID NO: 23.

\* \* \* \* \*

UNITED STATES PATENT AND TRADEMARK OFFICE
CERTIFICATE OF CORRECTION

PATENT NO. : 10,849,966 B2
APPLICATION NO. : 16/134070
DATED : December 1, 2020
INVENTOR(S) : Ruiz-Opazo et al.

It is certified that error appears in the above-identified patent and that said Letters Patent is hereby corrected as shown below:

In the Specification

Column 1, Lines 13-18, delete the following paragraph:
"GOVERNMENT SUPPORT
This invention was made with government support under Grant No. T32EB006359 awarded by the National Institutes of Health. The government has certain rights in the invention."

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Gly Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Trp Asp Asp Gly Ser Thr Asp Tyr Asn Ser Ala Leu Lys Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Pro Val Val His Phe Tyr Ala Met Asp Tyr
1               5                   10

<210> SEQ ID NO 4
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 4

Gly Ser Gln Val Gln Leu Gln Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Gly Tyr Gly Val Asn Trp Val Arg Gln Pro Pro Gly Lys Gly Leu Glu
        35                  40                  45

Trp Leu Gly Met Ile Trp Asp Asp Gly Ser Thr Asp Tyr Asn Ser Ala
    50                  55                  60

Leu Lys Ser Arg Leu Ile Ile Thr Lys Asp Asn Ser Arg Ser Gln Val
65                  70                  75                  80

Phe Leu Lys Met Asn Ser Leu Gln Thr Asp Asp Thr Ala Arg Tyr Tyr
                85                  90                  95

Cys Ala Arg Asp Pro Val Val His Phe Tyr Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Gly Gly Gly Gly Ser
    130                 135

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Tyr Trp Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Asn Pro Asp Ser Ser Thr Ile Asn Tyr Thr Pro Ser Leu Lys
1               5                   10                  15

Asp

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gly Arg Gly Met Asp Tyr
1               5

<210> SEQ ID NO 8
<211> LENGTH: 132
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 8

```
Gly Ser Glu Val Gln Leu Gln Glu Ser Gly Gly Leu Val Gln Pro
1               5                   10                  15

Gly Gly Ser Leu Lys Leu Ser Cys Ala Ala Ser Gly Phe Asp Phe Ser
            20                  25                  30

Arg Tyr Trp Met Ser Trp Val Arg Gln Ala Pro Gly Lys Gly Leu Glu
        35                  40                  45

Trp Ile Gly Glu Ile Asn Pro Asp Ser Ser Thr Ile Asn Tyr Thr Pro
50                  55                  60

Ser Leu Lys Asp Lys Phe Ile Ile Ser Arg Asp Thr Ala Lys Thr
65                  70                  75                  80

Leu Tyr Leu Gln Met Ser Lys Val Arg Ser Glu Asp Thr Ala Leu Tyr
                85                  90                  95

Tyr Cys Ala Arg His Gly Arg Gly Met Asp Tyr Trp Ser Gln Gly Thr
            100                 105                 110

Ser Val Thr Val Ser Ser Ala Lys Thr Thr Pro Pro Ser Val Tyr Gly
        115                 120                 125

Gly Gly Ser
    130
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Lys Ala Ser Gln Asn Val Asp Ser Asn Val Ala
1               5                   10
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Ser Ala Ser Tyr Arg Tyr Ser
1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gln Gln Tyr His Ser Tyr Pro
1               5
```

```
<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Gly Gly Gly Ser Asp Ile Val Leu Thr Gln Thr Asn Gln Ile Met
1               5                   10                  15

Ser Ala Ser Val Gly Asp Arg Val Ser Val Thr Cys Lys Ala Ser Gln
            20                  25                  30

Asn Val Asp Ser Asn Val Ala Trp Tyr Gln Gln Lys Pro Gly His Ser
        35                  40                  45

Pro Lys Ala Leu Ile Tyr Ser Ala Ser Tyr Arg Tyr Ser Arg Val Pro
    50                  55                  60

Asp Arg Ile Thr Gly Ser Gly Ser Gly Thr Asp Phe Thr Leu Thr Ile
65                  70                  75                  80

Thr Asn Val Gln Ser Lys Asp Leu Ala Asp Tyr Phe Cys Gln Gln Tyr
                85                  90                  95

His Ser Tyr Pro Leu Leu Ala Phe Gly Ala Gly Thr Lys Leu Glu Leu
            100                 105                 110

Lys Arg Ala Asp Ala Ala Pro Thr Val Ser Leu Glu
        115                 120

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Gln Ser Val Ser Asn Asp Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ala Ser Asn Arg Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Asp Tyr Ser Ser Pro Phe Thr
1               5
```

```
<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Gly Ser Asp Ile Val Leu Thr Gln Thr His Lys Phe Leu Leu
1               5                   10                  15

Val Ser Ala Gly Asp Arg Ile Thr Ile Thr Cys Lys Ala Ser Gln Ser
            20                  25                  30

Val Ser Asn Asp Val Ala Trp Tyr Gln Gln Lys Pro Gly Gln Ser Pro
        35                  40                  45

Lys Leu Leu Ile Tyr Tyr Ala Ser Asn Arg Tyr Thr Gly Val Pro Asp
    50                  55                  60

Arg Phe Thr Gly Ser Gly Tyr Gly Thr Asp Phe Thr Phe Thr Ile Ser
65                  70                  75                  80

Thr Val Gln Ala Asp Asp Leu Ala Val Tyr Phe Cys Gln Gln Asp Tyr
                85                  90                  95

Ser Ser Pro Phe Thr Phe Gly Gly Gly Thr Lys Leu Glu Ile Lys Arg
            100                 105                 110

Ala Asp Ala Ala Pro Thr Val Ser Leu Glu
        115                 120

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ala Ser Ser Ser Val Ser Phe Met His
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Ser Asn Leu Ala Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Arg Ser Ser Tyr Pro
1               5
```

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gly Gly Gly Gly Ser Asp Ile Val Ile Thr Gln Ser Asn Ala Ile Met
1               5                   10                  15

Ser Ala Ser Pro Gly Glu Lys Val Thr Ile Thr Cys Ser Ala Ser Ser
            20                  25                  30

Ser Val Ser Phe Met His Trp Phe Gln Gln Lys Pro Gly Thr Ser Pro
        35                  40                  45

Lys Leu Trp Ile Tyr Ser Thr Ser Asn Leu Ala Ser Gly Val Pro Ala
    50                  55                  60

Arg Phe Ser Gly Ser Gly Ser Gly Thr Ser Tyr Ser Leu Thr Ile Ser
65                  70                  75                  80

Arg Met Glu Ala Glu Asp Ala Ala Thr Tyr Tyr Cys Gln Gln Arg Ser
                85                  90                  95

Ser Tyr Pro Leu Thr Phe Gly Ala Gly Thr Lys Leu Glu Leu Lys Arg
            100                 105                 110

Ala Asp Ala Ala Pro Thr Val Ser Leu Glu
        115                 120
```

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ser Tyr Ala Val Ser
1               5
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Val Ile Trp Gly Asp Gly Ser Thr Asp Tyr His Ser Ala Leu Ile Ser
1               5                   10                  15
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gly Thr Gly Thr Gly Phe Ala Tyr
1               5
```

```
<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Lys Ser Tyr
            20                  25                  30

Ala Val Ser Trp Val Arg Gln Pro Pro Gly Lys Gly Leu Glu Trp Leu
        35                  40                  45

Gly Val Ile Trp Gly Asp Gly Ser Thr Asp Tyr His Ser Ala Leu Ile
    50                  55                  60

Ser Arg Leu Ser Ile Ser Lys Asp Asn Ser Lys Ser Gln Phe Phe Leu
65                  70                  75                  80

Arg Leu Asn Ser Leu Gln Thr Asp Asp Thr Ala Thr Tyr Tyr Cys Ala
                85                  90                  95

Arg Gly Thr Gly Thr Gly Phe Ala Tyr Trp Gly Gln Gly Thr Leu Val
            100                 105                 110

Thr Val Ser Ala
        115

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Ser Gln Ser Leu Val His Ser Asn Gly Asn Thr Tyr Leu His
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gln Cys Thr His Ile Pro Trp Thr
1               5
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Cys
                85                  90                  95

Thr His Ile Pro Trp Thr Phe Gly Gly Gly Thr Asn Leu Glu Ile Lys
            100                 105                 110
```

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Gly Phe Ser Leu Thr Ser Tyr Asp Ile Ser
1               5                   10
```

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Val Ile Trp Thr Gly Gly Gly Thr Asn Tyr Asn Ser Ala Phe Met Ser
1               5                   10                  15
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Asp Arg Asp Tyr Asp Gly Trp Tyr Phe Asp Val
1               5                   10
```

<210> SEQ ID NO 32
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 32

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Asn Ser Lys Ser Gln Val Phe Leu
65              70                  75                  80

Lys Met Asn Ser Leu Gln Thr Asp Asp Thr Ala Ile Tyr Tyr Cys Val
                85                  90                  95

Arg Asp Arg Asp Tyr Asp Gly Tyr Phe Asp Val Trp Gly Ala Gly
            100                 105                 110

Thr Thr Val Thr Val Ser Ser
            115

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Ser Gln Ser Ile Val His Ser Asn Gly Asn Thr Tyr Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gln Gly Ser His Val Pro Tyr Thr
1               5

<210> SEQ ID NO 36
<211> LENGTH: 112
<212> TYPE: PRT
<213> ORGANISM: Artificial Sequence
```

<220> FEATURE:
<223> OTHER INFORMATION: Description of Artificial Sequence: Synthetic
    polypeptide

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 37
<211> LENGTH: 85
<212> TYPE: PRT
<213> ORGANISM: Homo sapiens

<400> SEQUENCE: 37

Met Thr Met Phe Lys Gly Ser Asn Glu Met Lys Ser Arg Trp Asn Trp
1               5                   10                  15

Gly Ser Ile Thr Cys Ile Ile Cys Phe Thr Cys Val Gly Ser Gln Leu
            20                  25                  30

Ser Met Ser Ser Ser Lys Ala Ser Asn Phe Ser Gly Pro Leu Gln Leu
        35                  40                  45

Tyr Gln Arg Glu Leu Glu Ile Phe Ile Val Leu Thr Asp Val Pro Asn
    50                  55                  60

Tyr Arg Leu Ile Lys Glu Asn Ser His Leu His Thr Thr Ile Val Asp
65                  70                  75                  80

Gln Gly Arg Thr Val
                85

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 38

Gly Gly Gly Gly Ser
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
    6xHis tag

```
<400> SEQUENCE: 39

His His His His His His
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ala Pro Val
1

<210> SEQ ID NO 41
<211> LENGTH: 13
<212> TYPE: PRT
<213> ORGANISM: Homo sapiens

<400> SEQUENCE: 41

Lys Ala Ser Asn Phe Ser Gly Pro Leu Gln Leu Tyr Gln
1               5                   10

<210> SEQ ID NO 42
<211> LENGTH: 15
<212> TYPE: PRT
<213> ORGANISM: Homo sapiens

<400> SEQUENCE: 42

Tyr Arg Leu Ile Lys Glu Asn Ser His Leu His Thr Thr Ile Val
1               5                   10                  15

<210> SEQ ID NO 43
<211> LENGTH: 15
<212> TYPE: PRT
<213> ORGANISM: Homo sapiens

<400> SEQUENCE: 43

Lys Glu Asn Ser His Leu His Thr Thr Ile Val Asp Gln Gly Arg
1               5                   10                  15

<210> SEQ ID NO 44
<211> LENGTH: 15
<212> TYPE: PRT
<213> ORGANISM: Homo sapiens

<400> SEQUENCE: 44

Glu Asn Ser His Leu His Thr Thr Ile Val Asp Gln Gly Arg Thr
1               5                   10                  15

<210> SEQ ID NO 45
<211> LENGTH: 9
<212> TYPE: PRT
<213> ORGANISM: Homo sapiens

<400> SEQUENCE: 45

Thr Ile Val Asp Gln Gly Arg Thr Val
1               5

<210> SEQ ID NO 46
<211> LENGTH: 15
<212> TYPE: PRT
<213> ORGANISM: Homo sapiens
```

```
<400> SEQUENCE: 46

Glu Asn Ser His Leu His Thr Thr Ile Val Asp Gln Gly Arg Thr
1               5                   10                  15

<210> SEQ ID NO 47
<211> LENGTH: 9
<212> TYPE: PRT
<213> ORGANISM: Homo sapiens

<400> SEQUENCE: 47

Thr Ile Val Asp Gln Gly Arg Thr Val
1               5

<210> SEQ ID NO 48
<211> LENGTH: 15
<212> TYPE: PRT
<213> ORGANISM: Homo sapiens

<400> SEQUENCE: 48

Tyr Arg Leu Ile Lys Glu Asn Ser His Leu His Thr Thr Ile Val
1               5                   10                  15

<210> SEQ ID NO 49
<211> LENGTH: 15
<212> TYPE: PRT
<213> ORGANISM: Homo sapiens

<400> SEQUENCE: 49

Glu Asn Ser His Leu His Thr Thr Ile Val Asp Gln Gly Arg Thr
1               5                   10                  15

<210> SEQ ID NO 50
<211> LENGTH: 9
<212> TYPE: PRT
<213> ORGANISM: Homo sapiens

<400> SEQUENCE: 50

Thr Ile Val Asp Gln Gly Arg Thr Val
1               5

<210> SEQ ID NO 51
<211> LENGTH: 10
<212> TYPE: PRT
<213> ORGANISM: Homo sapiens

<400> SEQUENCE: 51

Lys Ala Ser Asn Phe Ser Gly Pro Leu Gln
1               5                   10

<210> SEQ ID NO 52
<211> LENGTH: 15
<212> TYPE: PRT
<213> ORGANISM: Homo sapiens

<400> SEQUENCE: 52

Tyr Arg Leu Ile Lys Glu Asn Ser His Leu His Thr Thr Ile Val
1               5                   10                  15

<210> SEQ ID NO 53
<211> LENGTH: 9
<212> TYPE: PRT
<213> ORGANISM: Homo sapiens
```

```
<400> SEQUENCE: 53

Thr Ile Val Asp Gln Gly Arg Thr Val
1               5

<210> SEQ ID NO 54
<211> LENGTH: 15
<212> TYPE: PRT
<213> ORGANISM: Homo sapiens

<400> SEQUENCE: 54

Tyr Arg Leu Ile Lys Glu Asn Ser His Leu His Thr Thr Ile Val
1               5                   10                  15

<210> SEQ ID NO 55
<211> LENGTH: 10
<212> TYPE: PRT
<213> ORGANISM: Homo sapiens

<400> SEQUENCE: 55

Lys Ala Ser Asn Phe Ser Gly Pro Leu Gln
1               5                   10

<210> SEQ ID NO 56
<211> LENGTH: 13
<212> TYPE: PRT
<213> ORGANISM: Homo sapiens

<400> SEQUENCE: 56

Lys Ala Ser Asn Phe Ser Gly Pro Leu Gln Leu Tyr Gln
1               5                   10

<210> SEQ ID NO 57
<211> LENGTH: 10
<212> TYPE: PRT
<213> ORGANISM: Homo sapiens

<400> SEQUENCE: 57

Lys Ala Ser Asn Phe Ser Gly Pro Leu Gln
1               5                   10

<210> SEQ ID NO 58
<211> LENGTH: 13
<212> TYPE: PRT
<213> ORGANISM: Homo sapiens

<400> SEQUENCE: 58

Lys Ala Ser Asn Phe Ser Gly Pro Leu Gln Leu Tyr Gln
1               5                   10

<210> SEQ ID NO 59
<211> LENGTH: 13
<212> TYPE: PRT
<213> ORGANISM: Homo sapiens

<400> SEQUENCE: 59

Lys Ala Ser Asn Phe Ser Gly Pro Leu Gln Leu Tyr Gln
1               5                   10

<210> SEQ ID NO 60
<211> LENGTH: 9
<212> TYPE: PRT
<213> ORGANISM: Homo sapiens
```

```
<400> SEQUENCE: 60

Thr Ile Val Asp Gln Gly Arg Thr Val
1               5

<210> SEQ ID NO 61
<211> LENGTH: 48
<212> TYPE: PRT
<213> ORGANISM: Homo sapiens

<400> SEQUENCE: 61

Lys Ala Ser Asn Phe Ser Gly Pro Leu Gln Leu Tyr Gln Arg Glu Leu
1               5                   10                  15

Glu Ile Phe Ile Val Leu Thr Asp Val Pro Asn Tyr Arg Leu Ile Lys
            20                  25                  30

Glu Asn Ser His Leu His Thr Thr Ile Val Asp Gln Gly Arg Thr Val
        35                  40                  45

<210> SEQ ID NO 62
<211> LENGTH: 20
<212> TYPE: PRT
<213> ORGANISM: Homo sapiens

<400> SEQUENCE: 62

Ser Ile Thr Cys Ile Ile Cys Phe Thr Cys Val Gly Ser Gln Leu Ser
1               5                   10                  15

Met Ser Ser Ser
            20
```